US012577314B2

(12) United States Patent
Park et al.

(10) Patent No.: US 12,577,314 B2
(45) Date of Patent: Mar. 17, 2026

(54) ANTI-BCMA/ANTI-4-1BB BISPECIFIC ANTIBODIES AND USES THEREOF

(71) Applicant: ABL BIO INC., Gyeonggi-do (KR)

(72) Inventors: Kyung Jin Park, Gyeonggi-do (KR); Yang Soon Lee, Gyeonggi-do (KR); Sae Yi Lim, Gyeonggi-do (KR); Hye Jin Chung, Gyeonggi-do (KR); Kyeong Su Park, Gyeonggi-do (KR); Yong Gyu Son, Gyeonggi-do (KR); Seong Gyu Seon, Gyeonggi-do (KR); Won Jun Son, Gyeonggi-do (KR); Eun Jung Kim, Gyeonggi-do (KR); Jae Hyun Eom, Gyeonggi-do (KR); Ui Jung Jung, Gyeonggi-do (KR); Min Ji Park, Gyeonggi-do (KR); Jung Hyeon Hong, Gyeonggi-do (KR)

(73) Assignee: ABL BIO INC., Gyeonggi-do (KR)

( * ) Notice: Subject to any disclaimer, the term of this patent is extended or adjusted under 35 U.S.C. 154(b) by 902 days.

(21) Appl. No.: 17/783,344

(22) PCT Filed: Dec. 10, 2020

(86) PCT No.: PCT/KR2020/018029
§ 371 (c)(1),
(2) Date: Jun. 8, 2022

(87) PCT Pub. No.: WO2021/118246
PCT Pub. Date: Jun. 17, 2021

(65) Prior Publication Data
US 2023/0051266 A1 Feb. 16, 2023

Related U.S. Application Data

(60) Provisional application No. 62/945,965, filed on Dec. 10, 2019.

(51) Int. Cl.
*A61P 35/00* (2006.01)
*A61K 39/00* (2006.01)
*C07K 16/28* (2006.01)
*C07K 16/46* (2006.01)

(52) U.S. Cl.
CPC ...... *C07K 16/2878* (2013.01); *A61K 39/0011* (2013.01); *A61P 35/00* (2018.01); *C07K 16/468* (2013.01); *A61K 2039/505* (2013.01); *C07K 2317/21* (2013.01); *C07K 2317/31* (2013.01); *C07K 2317/33* (2013.01); *C07K 2317/526* (2013.01); *C07K 2317/565* (2013.01); *C07K 2317/622* (2013.01); *C07K 2317/732* (2013.01); *C07K 2317/75* (2013.01); *C07K 2317/92* (2013.01); *C07K 2317/94* (2013.01)

(58) Field of Classification Search
CPC .... C07K 16/468; C07K 16/2878; A61P 35/00
USPC ...................................... 424/136.1
See application file for complete search history.

(56) References Cited

U.S. PATENT DOCUMENTS

| | | | |
|---|---|---|---|
| 9,243,058 B2 | 1/2016 | Armitage et al. | |
| 9,334,331 B2 * | 5/2016 | Igawa | A61P 43/00 |
| 10,421,807 B2 * | 9/2019 | Gonzales | A61P 43/00 |
| 10,683,369 B2 | 6/2020 | Vu et al. | |
| 12,252,541 B2 * | 3/2025 | Park | C07K 16/30 |
| 2009/0162360 A1 | 6/2009 | Klein et al. | |
| 2017/0029518 A1 | 2/2017 | Kalled et al. | |
| 2017/0051068 A1 | 2/2017 | Pillarisetti et al. | |
| 2018/0051292 A1 | 2/2018 | Kochenderfer | |
| 2019/0071510 A1 | 3/2019 | Kwon et al. | |
| 2019/0194329 A1 | 6/2019 | Akamatsu et al. | |
| 2021/0079106 A1 * | 3/2021 | Beilhack | C07K 16/2878 |
| 2023/0114854 A1 * | 4/2023 | Song | C07K 14/705 424/144.1 |

FOREIGN PATENT DOCUMENTS

| | | |
|---|---|---|
| KR | 10-2018-0042271 A | 4/2018 |
| WO | WO-2015/158671 A1 | 10/2015 |
| WO | WO-2017/205745 A1 | 11/2017 |
| WO | 2021132746 * | 7/2021 |

OTHER PUBLICATIONS

Al Qaraghuli et al. (2020, Nature Scientific Reports 10:13969).*
Edwards et al. (2003, JMB 334:103-118).*
Lloyd et al. (2009, Protein Engineering, Eng. Design & Selection 22(3): 159-168).*
Goel et al. (2004, J. Immunol. 173: 7358-7367).*
Khan et al. (2014, J. Immunol. 192: 5398-5405).*
Poosarla et al. (2017, Biotechn. Bioeng. 114(6): 1331-1342).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Huang et al. (Appl Microbiol Biotechnol (2010) 87:401-410).*
Claus, C., et al.; "Tumor-targeted 4-1BB agonists for combination with T cell bispecific antibodies as off-the-shelf therapy", Sci. Transl. Med. 11, 2019, pp. 1-12.

(Continued)

*Primary Examiner* — Lynn A Bristol

(57) ABSTRACT

An anti-B-cell maturation antigen (BCMA)/anti-4-1BB bispecific antibody or an antigen-binding fragment thereof, and use thereof, are provided. The bispecific antibody or an antigen-binding fragment thereof may have high binding affinity to both of a BCMA protein and a 4-1BB protein and may be effectively used to prevent or treat a disease related to BCMA, 4-1BB, or both thereof.

11 Claims, 28 Drawing Sheets
Specification includes a Sequence Listing.

(56)　　　　　References Cited

OTHER PUBLICATIONS

Moreaux, J., et al.; "APRIL and TACI interact with syndecan-1 on the surface of multiple myeloma cells to form an essential survival loop", European Journal of Haematology 83 (119-129), 2009.

International Search Report from corresponding PCT Application No. PCT/KR2020/018029, dated Mar. 31, 2021.

Park Sunyoung et al. "The PD-L1 x 4-1BB bispecific antibody ABL503 shows potent anti-tumor effect through tumor-directed Tcell activation. PEGS Boston 2019." PEGS, Boston 2019, Apr. 12, 2019 pp. 1-1.

Makkouk Amani et al. "Rationale for anti-CD137 cancer immunotherapy", European Journal of Cancer, Elsevier, Amsterdam NL, vol. 54, Jan. 2, 2016, pp. 112-119.

Extended European Search Report from corresponding European Patent Application No. 20898646.3, dated Nov. 7, 2023.

Hidenori Wake, Antibody Medicine, Okayama medical society magazine, 2009, vol. 121, pp. 119-122.

Office Action from corresponding Japanese Patent Application No. 2022-535140, dated Jul. 4, 2025.

Office Action from corresponding Korean Patent Application No. 10-2022-7019355, dated Dec. 9, 2025.

* cited by examiner

WT BCMA Ab
B58,5A6,5D5 and 5B5

(NA)     G4S linker 4-1BB Ab
41B01, 41B02, and AB41

BCMA(NA)x41B01

BCMA(NA)x41B02

BCMA(NA)xAB41

FIG. 5c

DACE (BCMA−Fc tag coating)

Legend:

- 5D5(NA)x41B01 M12:WT
- 5D5M4(NA)x41B01 M12
- 5A6(NA)x41B01 M12:WT
- 5A6M6(NA)x41B01 M12

| | Sample Name | Mean: FL1-H |
|---|---|---|
| ☐ | 5A6M6(NA)x41B01 M12.007 | 102 |
| ☐ | 5A6(NA)x41B01 M12.005 | 101 |
| ☐ | 2nd Ab control.002 | 9.31 |
| ▨ | ONLY CELL.001 | 7.89 |

| | Sample Name | Mean: FL1-H |
|---|---|---|
| ☐ | 5D5M4(NA)x41B01 M12.004 | 64.8 |
| ☐ | 5D5(NA)x41B01 M12.003 | 37.5 |
| ☐ | 2nd Ab control.002 | 9.31 |
| ▨ | ONLY CELL.001 | 7.89 |

H929
BCMA-High cancer cell

5D5WT(NA)x41B01 M12
5D5M4(NA)x41B01 M12
5A6WT(NA)x41B01 M12
5A6M6(NA)x41B01 M12

MM1S
BCMA-Moderate cancer cell

○ 5D5WT(NA)x41B01 M12
● 5D5M4(NA)x41B01 M12
□ 5A6WT(NA)x41B01 M12
■ 5A6M6(NA)x41B01 M12

Jurkat
BCMA-Negative cancer cell

SEQUENCE LISTING

```
<160> NUMBER OF SEQ ID NOS: 130

<210> SEQ ID NO 1
<211> LENGTH: 184
<212> TYPE: PRT
<213> ORGANISM: Artificial Sequence
<220> FEATURE:
<223> OTHER INFORMATION: Human BCMA(NP_001183.2)

<400> SEQUENCE: 1

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
            115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
                180

<210> SEQ ID NO 2
<211> LENGTH: 121
<212> TYPE: PRT
<213> ORGANISM: Artificial Sequence
<220> FEATURE:
<223> OTHER INFORMATION: Heavy chain variable region of anti-BCMA
      antibody B58

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
        35                  40                  45

Ser Trp Ile Tyr Pro Ser Asp Ser Ser Ile Tyr Tyr Ala Asp Ser Val
```

-continued

```
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Phe Ala Asn Lys Tyr Arg Gln Phe Asp Tyr Trp Gly
            100                 105                 110

Gln Gly Thr Leu Val Thr Val Ser Ser
        115                 120

<210> SEQ ID NO 3
<211> LENGTH: 116
<212> TYPE: PRT
<213> ORGANISM: Artificial Sequence
<220> FEATURE:
<223> OTHER INFORMATION: Heavy chain variable region of anti-BCMA
      antibody 5B5

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly His
                20                  25                  30

Tyr Trp Ser Trp Val Arg Gln Ala Pro Gly Lys Gly Leu Glu Trp Val
            35                  40                  45

Ser Thr Val Ser Gly Ser Gly Gly Asp Thr Phe Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly His Ser Val Met Asp Val Trp Gly Gln Gly Thr Leu Val
            100                 105                 110

Thr Val Ser Ser
        115

<210> SEQ ID NO 4
<211> LENGTH: 116
<212> TYPE: PRT
<213> ORGANISM: Artificial Sequence
<220> FEATURE:
<223> OTHER INFORMATION: Heavy chain variable region of anti-BCMA
      antibody 5D5

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Gly Leu Ser Trp Val Arg Gln Ala Pro Gly Lys Gly Leu Glu Trp Val
            35                  40                  45

Ser Leu Ile Asp Ser Ser Gly Ser Ser Thr Phe Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu His Gly Leu Phe Asp Ser Trp Gly Gln Gly Thr Leu Val
```

-continued

```
                100                 105                 110

Thr Val Ser Ser
        115

<210> SEQ ID NO 5
<211> LENGTH: 117
<212> TYPE: PRT
<213> ORGANISM: Artificial Sequence
<220> FEATURE:
<223> OTHER INFORMATION: Heavy chain variable region of anti-BCMA
      antibody 5A6

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Val His Trp Val Arg Gln Ala Pro Gly Lys Gly Leu Glu Trp Val
        35                  40                  45

Ser Tyr Ile Ser Tyr Ser Gly Gly Thr Tyr Tyr Asn Pro Ser Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Ser Asp Asp Phe Gly Phe Asp Tyr Trp Gly Gln Gly Thr Leu
            100                 105                 110

Val Thr Val Ser Ser
        115

<210> SEQ ID NO 6
<211> LENGTH: 111
<212> TYPE: PRT
<213> ORGANISM: Artificial Sequence
<220> FEATURE:
<223> OTHER INFORMATION: Light chain variable region of anti-BCMA
      antibody B58

<400> SEQUENCE: 6

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Ser Val Ser Trp Tyr Gln Gln Leu Pro Gly Thr Ala Pro Lys Leu Leu
        35                  40                  45

Ile Tyr Ala Asp Ser Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Gly Tyr Val Phe Gly Gly Gly Thr Lys Leu Thr Val Leu Gly
            100                 105                 110

<210> SEQ ID NO 7
<211> LENGTH: 108
<212> TYPE: PRT
<213> ORGANISM: Artificial Sequence
<220> FEATURE:
<223> OTHER INFORMATION: Light chain variable region of anti-BCMA
``` antibody 5B5

<400> SEQUENCE: 7

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Ile Asp Ser Tyr
            20                  25                  30

Val Ala Trp Tyr Gln Gln Lys Pro Gly Gln Ala Pro Arg Leu Leu Ile
        35                  40                  45

Tyr Asp Ala Ser Leu Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asn Ser Trp Pro Ile
                85                  90                  95

Thr Phe Gly Gln Gly Thr Lys Leu Glu Ile Lys Arg
            100                 105

<210> SEQ ID NO 8
<211> LENGTH: 108
<212> TYPE: PRT
<213> ORGANISM: Artificial Sequence
<220> FEATURE:
<223> OTHER INFORMATION: Light chain variable region of anti-BCMA
      antibody 5D5

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Asp Ile Asp Asp Asp
            20                  25                  30

Ile Asn Trp Tyr Gln Gln Lys Pro Gly Gln Ala Pro Arg Leu Leu Ile
        35                  40                  45

Tyr Asp Ala Ser Leu Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Leu Arg Thr Pro Ile
                85                  90                  95

Thr Phe Gly Gln Gly Thr Lys Leu Glu Ile Lys Arg
            100                 105

<210> SEQ ID NO 9
<211> LENGTH: 107
<212> TYPE: PRT
<213> ORGANISM: Artificial Sequence
<220> FEATURE:
<223> OTHER INFORMATION: Light chain variable region of anti-BCMA
      antibody 5A6

<400> SEQUENCE: 9

Gln Ser Val Leu Thr Gln Pro Pro Ser Ala Ser Gly Thr Pro Gly Gln
1               5                   10                  15

Arg Val Thr Ile Ser Cys Gln Gly Asp Ser Leu Arg Ser Tyr Tyr Val
            20                  25                  30

Asn Trp Tyr Gln Gln Leu Pro Gly Thr Ala Pro Lys Leu Leu Ile Tyr
        35                  40                  45

Asp His Ser Lys Arg Pro Thr Gly Val Pro Asp Arg Phe Ser Gly Ser
    50                  55                  60

```
Lys Ser Gly Thr Ser Ala Ser Leu Ala Ile Ser Gly Leu Arg Ser Glu
65                  70                  75                  80

Asp Glu Ala Asp Tyr Tyr Cys Gln Ser Tyr Asp Ser Ser Thr Val Val
                85                  90                  95

Phe Gly Gly Gly Thr Lys Leu Thr Val Leu Gly
            100                 105

<210> SEQ ID NO 10
<211> LENGTH: 5
<212> TYPE: PRT
<213> ORGANISM: Artificial Sequence
<220> FEATURE:
<223> OTHER INFORMATION: Heavy chain CDR1 of anti-BCMA antibody

<400> SEQUENCE: 10

Asn Tyr Asp Met Ser
1               5

<210> SEQ ID NO 11
<211> LENGTH: 5
<212> TYPE: PRT
<213> ORGANISM: Artificial Sequence
<220> FEATURE:
<223> OTHER INFORMATION: Heavy chain CDR1 of anti-BCMA antibody

<400> SEQUENCE: 11

Gly His Tyr Trp Ser
1               5

<210> SEQ ID NO 12
<211> LENGTH: 5
<212> TYPE: PRT
<213> ORGANISM: Artificial Sequence
<220> FEATURE:
<223> OTHER INFORMATION: Heavy chain CDR1 of anti-BCMA antibody

<400> SEQUENCE: 12

Asp Tyr Gly Leu Ser
1               5

<210> SEQ ID NO 13
<211> LENGTH: 5
<212> TYPE: PRT
<213> ORGANISM: Artificial Sequence
<220> FEATURE:
<223> OTHER INFORMATION: Heavy chain CDR1 of anti-BCMA antibody

<400> SEQUENCE: 13

Asn Tyr Gly Val His
1               5

<210> SEQ ID NO 14
<211> LENGTH: 17
<212> TYPE: PRT
<213> ORGANISM: Artificial Sequence
<220> FEATURE:
<223> OTHER INFORMATION: Heavy chain CDR2 of anti-BCMA antibody

<400> SEQUENCE: 14

Trp Ile Tyr Pro Ser Asp Ser Ser Ile Tyr Tyr Ala Asp Ser Val Lys
1               5                   10                  15

Gly

<210> SEQ ID NO 15
```

```
<211> LENGTH: 17
<212> TYPE: PRT
<213> ORGANISM: Artificial Sequence
<220> FEATURE:
<223> OTHER INFORMATION: Heavy chain CDR3 of anti-BCMA antibody

<400> SEQUENCE: 15

Thr Val Ser Gly Ser Gly Gly Asp Thr Phe Tyr Ala Asp Ser Val Lys
1               5                   10                  15

Gly

<210> SEQ ID NO 16
<211> LENGTH: 17
<212> TYPE: PRT
<213> ORGANISM: Artificial Sequence
<220> FEATURE:
<223> OTHER INFORMATION: Heavy chain CDR4 of anti-BCMA antibody

<400> SEQUENCE: 16

Leu Ile Asp Ser Ser Gly Ser Ser Thr Phe Tyr Ala Asp Ser Val Lys
1               5                   10                  15

Gly

<210> SEQ ID NO 17
<211> LENGTH: 16
<212> TYPE: PRT
<213> ORGANISM: Artificial Sequence
<220> FEATURE:
<223> OTHER INFORMATION: Heavy chain CDR5 of anti-BCMA antibody

<400> SEQUENCE: 17

Tyr Ile Ser Tyr Ser Gly Gly Thr Tyr Tyr Asn Pro Ser Leu Lys Ser
1               5                   10                  15

<210> SEQ ID NO 18
<211> LENGTH: 13
<212> TYPE: PRT
<213> ORGANISM: Artificial Sequence
<220> FEATURE:
<223> OTHER INFORMATION: Heavy chain CDR3 of anti-BCMA antibody

<400> SEQUENCE: 18

Arg Gly Pro Phe Ala Asn Lys Tyr Arg Gln Phe Asp Tyr
1               5                   10

<210> SEQ ID NO 19
<211> LENGTH: 8
<212> TYPE: PRT
<213> ORGANISM: Artificial Sequence
<220> FEATURE:
<223> OTHER INFORMATION: Heavy chain CDR3 of anti-BCMA antibody

<400> SEQUENCE: 19

Arg Gly His Ser Val Met Asp Val
1               5

<210> SEQ ID NO 20
<211> LENGTH: 8
<212> TYPE: PRT
<213> ORGANISM: Artificial Sequence
<220> FEATURE:
<223> OTHER INFORMATION: Heavy chain CDR3 of anti-BCMA antibody

<400> SEQUENCE: 20

Lys Glu His Gly Leu Phe Asp Ser
1               5
```

```
<210> SEQ ID NO 21
<211> LENGTH: 10
<212> TYPE: PRT
<213> ORGANISM: Artificial Sequence
<220> FEATURE:
<223> OTHER INFORMATION: Heavy chain CDR3 of anti-BCMA antibody

<400> SEQUENCE: 21

Arg Asp Ser Asp Asp Phe Gly Phe Asp Tyr
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Light chain CDR1 of anti-BCMA antibody

<400> SEQUENCE: 22

Ser Gly Ser Ser Ser Asn Ile Gly Ser Asn Ser Val Ser
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Light chain CDR1 of anti-BCMA antibody

<400> SEQUENCE: 23

Arg Ala Ser Gln Gly Ile Asp Ser Tyr Val Ala
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Light chain CDR1 of anti-BCMA antibody

<400> SEQUENCE: 24

Lys Ala Ser Gln Asp Ile Asp Asp Asp Ile Asn
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Light chain CDR1 of anti-BCMA antibody

<400> SEQUENCE: 25

Gln Gly Asp Ser Leu Arg Ser Tyr Tyr Val Asn
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Light chain CDR2 of anti-BCMA antibody

<400> SEQUENCE: 26

Ala Asp Ser Lys Arg Pro Ser
1               5
```

```
<210> SEQ ID NO 27
<211> LENGTH: 7
<212> TYPE: PRT
<213> ORGANISM: Artificial Sequence
<220> FEATURE:
<223> OTHER INFORMATION: Light chain CDR2 of anti-BCMA antibody

<400> SEQUENCE: 27

Asp Ala Ser Leu Arg Ala Thr
1               5

<210> SEQ ID NO 28
<211> LENGTH: 7
<212> TYPE: PRT
<213> ORGANISM: Artificial Sequence
<220> FEATURE:
<223> OTHER INFORMATION: Light chain CDR2 of anti-BCMA antibody

<400> SEQUENCE: 28

Asp His Ser Lys Arg Pro Thr
1               5

<210> SEQ ID NO 29
<211> LENGTH: 11
<212> TYPE: PRT
<213> ORGANISM: Artificial Sequence
<220> FEATURE:
<223> OTHER INFORMATION: Light chain CDR3 of anti-BCMA antibody

<400> SEQUENCE: 29

Gly Ser Trp Asp Tyr Ser Leu Ser Gly Tyr Val
1               5                   10

<210> SEQ ID NO 30
<211> LENGTH: 8
<212> TYPE: PRT
<213> ORGANISM: Artificial Sequence
<220> FEATURE:
<223> OTHER INFORMATION: Light chain CDR3 of anti-BCMA antibody

<400> SEQUENCE: 30

Gln Gln Tyr Asn Ser Trp Pro Ile
1               5

<210> SEQ ID NO 31
<211> LENGTH: 8
<212> TYPE: PRT
<213> ORGANISM: Artificial Sequence
<220> FEATURE:
<223> OTHER INFORMATION: Light chain CDR3 of anti-BCMA antibody

<400> SEQUENCE: 31

Gln Gln Ser Leu Arg Thr Pro Ile
1               5

<210> SEQ ID NO 32
<211> LENGTH: 8
<212> TYPE: PRT
<213> ORGANISM: Artificial Sequence
<220> FEATURE:
<223> OTHER INFORMATION: Light chain CDR3 of anti-BCMA antibody

<400> SEQUENCE: 32

Gln Ser Tyr Asp Ser Ser Thr Val
1               5
```

-continued

```
<210> SEQ ID NO 33
<211> LENGTH: 363
<212> TYPE: DNA
<213> ORGANISM: Artificial Sequence
<220> FEATURE:
<223> OTHER INFORMATION: Polynucleotide encoding heavy chain variable
      region of anti-BCMA antibody B58

<400> SEQUENCE: 33
gaggtgcagc tgctggagtc cggcggcggc ctggtgcagc ccggcggctc cctgcggctg      60
tcctgcgccg cctccggctt caccttctcc aactacgaca tgtcctgggt gcggcaggcc     120
cccggcaagg gcctggagtg ggtgtcctgg atctacccct ccgactcctc catctactac     180
gccgactccg tgaagggccg gttcaccatc tcccgggaca actccaagaa caccctgtac     240
ctgcagatga actccctgcg ggccgaggac accgccgtgt actactgcgc ccggggcccc     300
ttcgccaaca gtaccggca gttcgactac tggggccagg gcaccctggt gaccgtgtcc     360
tcc                                                                 363

<210> SEQ ID NO 34
<211> LENGTH: 348
<212> TYPE: DNA
<213> ORGANISM: Artificial Sequence
<220> FEATURE:
<223> OTHER INFORMATION: Polynucleotide encoding heavy chain variable
      region of anti-BCMA antibody 5B5

<400> SEQUENCE: 34
gaggtccagt tgttggaaag cggtggtggt ttggttcaac caggcggtag cctcagactc      60
tcctgcgctg cctccgggtt tactttctca gggcactatt ggtcctgggt ccgtcaggca     120
cctggtaagg gacttgaatg ggtatctaca gtttccggct ccggtggaga cactttttat     180
gcagacagcg ttaagggggcg ctttactata agtcgtgata attccaaaaa tactctctat     240
ctccaaatga actccctccg tgctgaagat accgctgtgt actactgcgc tcgaggtcac     300
tcagtcatgg acgtatgggg gcagggcaca ctggtgaccg tatcttcc                 348

<210> SEQ ID NO 35
<211> LENGTH: 348
<212> TYPE: DNA
<213> ORGANISM: Artificial Sequence
<220> FEATURE:
<223> OTHER INFORMATION: Polynucleotide encoding heavy chain variable
      region of anti-BCMA antibody 5D5

<400> SEQUENCE: 35
gaggtccagt tgttggaaag cggtggtggt ttggttcaac caggcggtag cctcagactc      60
tcctgcgctg cctccgggtt tactttcagc gattatggac tgtcatgggt gcgtcaagct     120
cctggaaaag ggttggagtg ggtgagcctt atagacagca gtgggagtag cactttctac     180
gctgatagcg tgaaaggtag atttactatc tctcgtgata actccaagaa tacattgtat     240
cttcaaatga acagtctgag agctgaggac actgccgttt attattgtgc aaaggaacat     300
ggtcttttcg actcatgggg acagggaaca ctggtgaccg tatcttcc                 348

<210> SEQ ID NO 36
<211> LENGTH: 351
<212> TYPE: DNA
<213> ORGANISM: Artificial Sequence
<220> FEATURE:
<223> OTHER INFORMATION: Polynucleotide encoding heavy chain variable
      region of anti-BCMA antibody 5A6
```

-continued

```
<400> SEQUENCE: 36
gaggtccagt tgttggaaag cggtggtggt ttggttcaac caggcggtag cctcagactc      60
tcctgcgctg cctccgggtt tactttcagt aactatggag tacattgggt cagacaagcc     120
cccggcaaag gtcttgagtg ggtcagctac atttcctata gcggaggaac ttactataac     180
ccctcactta aaagccgctt cactatatca cgcgataata gcaagaacac cctctatctt     240
caaatgaact ctctgcgagc agaagacacc gccgtgtact attgcgctag agatagcgac     300
gacttcgggt tcgattattg gggacagggc acactggtga ccgtatcttc c              351

<210> SEQ ID NO 37
<211> LENGTH: 333
<212> TYPE: DNA
<213> ORGANISM: Artificial Sequence
<220> FEATURE:
<223> OTHER INFORMATION: Polynucleotide encoding light chain variable
      region of anti-BCMA antibody B58

<400> SEQUENCE: 37
cagtccgtgc tgacccagcc cccctccgcc tccggcaccc ccggccagcg ggtgaccatc      60
tcctgctccg gctcctcctc caacatcggc tccaactccg tgtcctggta ccagcagctg     120
cccggcaccg cccccaagct gctgatctac gccgactcca gcggccctc cggcgtgccc      180 gaccggttct ccggctccaa gtccggcacc tccgcctccc tggccatctc cggcctgcgg     240
tccgaggacg aggccgacta ctactgcggc tcctgggact actccctgtc cggctacgtg     300
ttcggcggcg gcaccaagct gaccgtgctg ggc                                   333

<210> SEQ ID NO 38
<211> LENGTH: 324
<212> TYPE: DNA
<213> ORGANISM: Artificial Sequence
<220> FEATURE:
<223> OTHER INFORMATION: Polynucleotide encoding light chain variable
      region of anti-BCMA antibody 5B5

<400> SEQUENCE: 38
gaaatagtac ttacacagtc ccctggaact ctgtcacttt cccctgggga gcgagctaca      60
ctgagctgtc gtgccagcca gggcattgat agttacgtgg catggtatca gcagaagccc     120
ggccaggctc caaggctgtt gatttacgat gcatcattgc gagccaccgg aatacctgac     180
cgtttctccg gcagtggctc cgggacagac tttaccctta ctatctcacg tctcgagcca     240
gaagactttg cagtgtatta ttgccaacaa tacaacagtt ggcctataac cttcggccag     300
gggacaaaac tggagataaa gcgt                                             324

<210> SEQ ID NO 39
<211> LENGTH: 324
<212> TYPE: DNA
<213> ORGANISM: Artificial Sequence
<220> FEATURE:
<223> OTHER INFORMATION: Polynucleotide encoding light chain variable
      region of anti-BCMA antibody 5D5

<400> SEQUENCE: 39
gaaatagtac ttacacagtc ccctggaact ctgtcacttt cccctgggga gcgagctaca      60
ctgagctgta aagcctcaca ggacatagac gatgacatca actggtatca gcaaaaacct     120
ggacaagctc acgtctcct gatttacgat gcatcactta gggccacagg aattcctgat      180
aggttctctg gtagcggcag tggaaccgat tttaccctca caatatctcg acttgaacca     240
```

-continued

```
gaagatttcg ccgtttatta ctgtcagcag tcccttagga cccccattac attcggccag      300
gggacaaaac tggagataaa gcgt                                             324
```

<210> SEQ ID NO 40
<211> LENGTH: 321
<212> TYPE: DNA
<213> ORGANISM: Artificial Sequence
<220> FEATURE:
<223> OTHER INFORMATION: Polynucleotide encoding light chain variable
      region of anti-BCMA antibody 5A6

<400> SEQUENCE: 40

```
caatctgtcc ttacacagcc tccaagcgca agcggcaccc ccggacaaag ggtaacaata       60
tcatgccagg gggattctct tcgcagctat tacgtgaatt ggtatcagca gttgcccggc      120 actgcccca aacttttgat atacgatcac tccaagcgcc ccacaggagt gcctgatagg       180
ttcagcggat ctaagtctgg aacatccgct tctttggcaa tctctgggct gcgaagtgag      240
gacgaggcag actactactg ccagtcttat gacagctcta ctgtagtctt cggaggcggt      300
acaaaactga cagtgctcgg t                                                321
```

<210> SEQ ID NO 41
<211> LENGTH: 108
<212> TYPE: PRT
<213> ORGANISM: Artificial Sequence
<220> FEATURE:
<223> OTHER INFORMATION: Light chain variable region of 5D5 M1

<400> SEQUENCE: 41

```
Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Asp Ile Asp Asn Asp
            20                  25                  30

Ile Asn Trp Tyr Gln Gln Lys Pro Gly Gln Ala Pro Arg Leu Leu Ile
        35                  40                  45

Tyr Asp Ala Ser Leu Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Leu Arg Thr Pro Ile
                85                  90                  95

Thr Phe Gly Gln Gly Thr Lys Leu Glu Ile Lys Arg
            100                 105
```

<210> SEQ ID NO 42
<211> LENGTH: 108
<212> TYPE: PRT
<213> ORGANISM: Artificial Sequence
<220> FEATURE:
<223> OTHER INFORMATION: Light chain variable region of 5D5 M2

<400> SEQUENCE: 42

```
Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Asp Ile Asp Glu Asp
            20                  25                  30

Ile Asn Trp Tyr Gln Gln Lys Pro Gly Gln Ala Pro Arg Leu Leu Ile
        35                  40                  45

Tyr Asp Ala Ser Leu Arg Ala Thr Gly Ile Pro Asp Arg Phe Ser Gly
    50                  55                  60
```

-continued

```
Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Leu Arg Thr Pro Ile
                85                  90                  95

Thr Phe Gly Gln Gly Thr Lys Leu Glu Ile Lys Arg
            100                 105

<210> SEQ ID NO 43
<211> LENGTH: 108
<212> TYPE: PRT
<213> ORGANISM: Artificial Sequence
<220> FEATURE:
<223> OTHER INFORMATION: Light chain variable region of 5D5 M3

<400> SEQUENCE: 43

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Asp Ile Asp Ala Asp
                20                  25                  30

Ile Asn Trp Tyr Gln Gln Lys Pro Gly Gln Ala Pro Arg Leu Leu Ile
            35                  40                  45

Tyr Asp Ala Ser Leu Arg Ala Thr Gly Ile Pro Asp Arg Phe Ser Gly
        50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Leu Arg Thr Pro Ile
                85                  90                  95

Thr Phe Gly Gln Gly Thr Lys Leu Glu Ile Lys Arg
            100                 105

<210> SEQ ID NO 44
<211> LENGTH: 108
<212> TYPE: PRT
<213> ORGANISM: Artificial Sequence
<220> FEATURE:
<223> OTHER INFORMATION: Light chain variable region of 5D5 M4

<400> SEQUENCE: 44

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Asp Ile Asp Asp Ala
                20                  25                  30

Ile Asn Trp Tyr Gln Gln Lys Pro Gly Gln Ala Pro Arg Leu Leu Ile
            35                  40                  45

Tyr Asp Ala Ser Leu Arg Ala Thr Gly Ile Pro Asp Arg Phe Ser Gly
        50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Leu Arg Thr Pro Ile
                85                  90                  95

Thr Phe Gly Gln Gly Thr Lys Leu Glu Ile Lys Arg
            100                 105

<210> SEQ ID NO 45
<211> LENGTH: 108
<212> TYPE: PRT
<213> ORGANISM: Artificial Sequence
<220> FEATURE:
<223> OTHER INFORMATION: Light chain variable region of 5D5 M5
```

<400> SEQUENCE: 45

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Asp Ile Asp Asp Glu
            20                  25                  30

Ile Asn Trp Tyr Gln Gln Lys Pro Gly Gln Ala Pro Arg Leu Leu Ile
        35                  40                  45

Tyr Asp Ala Ser Leu Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Leu Arg Thr Pro Ile
                85                  90                  95

Thr Phe Gly Gln Gly Thr Lys Leu Glu Ile Lys Arg
            100                 105

<210> SEQ ID NO 46
<211> LENGTH: 107
<212> TYPE: PRT
<213> ORGANISM: Artificial Sequence
<220> FEATURE:
<223> OTHER INFORMATION: Light chain variable region of 5A6 M1

<400> SEQUENCE: 46

Gln Ser Val Leu Thr Gln Pro Pro Ser Ala Ser Gly Thr Pro Gly Gln
1               5                   10                  15

Arg Val Thr Ile Ser Cys Gln Gly Glu Ser Leu Arg Ser Tyr Tyr Val
            20                  25                  30

Asn Trp Tyr Gln Gln Leu Pro Gly Thr Ala Pro Lys Leu Leu Ile Tyr
        35                  40                  45

Asp His Ser Lys Arg Pro Thr Gly Val Pro Asp Arg Phe Ser Gly Ser
    50                  55                  60

Lys Ser Gly Thr Ser Ala Ser Leu Ala Ile Ser Gly Leu Arg Ser Glu
65                  70                  75                  80

Asp Glu Ala Asp Tyr Tyr Cys Gln Ser Tyr Asp Ser Ser Thr Val Val
                85                  90                  95

Phe Gly Gly Gly Thr Lys Leu Thr Val Leu Gly
            100                 105

<210> SEQ ID NO 47
<211> LENGTH: 107
<212> TYPE: PRT
<213> ORGANISM: Artificial Sequence
<220> FEATURE:
<223> OTHER INFORMATION: Light chain variable region of 5A6 M2

<400> SEQUENCE: 47

Gln Ser Val Leu Thr Gln Pro Pro Ser Ala Ser Gly Thr Pro Gly Gln
1               5                   10                  15

Arg Val Thr Ile Ser Cys Gln Gly Asp Ala Leu Arg Ser Tyr Tyr Val
            20                  25                  30

Asn Trp Tyr Gln Gln Leu Pro Gly Thr Ala Pro Lys Leu Leu Ile Tyr
        35                  40                  45

Asp His Ser Lys Arg Pro Thr Gly Val Pro Asp Arg Phe Ser Gly Ser
    50                  55                  60

Lys Ser Gly Thr Ser Ala Ser Leu Ala Ile Ser Gly Leu Arg Ser Glu
65                  70                  75                  80

-continued

```
Asp Glu Ala Asp Tyr Tyr Cys Gln Ser Tyr Asp Ser Ser Thr Val Val
                85                  90                  95

Phe Gly Gly Gly Thr Lys Leu Thr Val Leu Gly
            100                 105

<210> SEQ ID NO 48
<211> LENGTH: 107
<212> TYPE: PRT
<213> ORGANISM: Artificial Sequence
<220> FEATURE:
<223> OTHER INFORMATION: Light chain variable region of 5A6 M3

<400> SEQUENCE: 48

Gln Ser Val Leu Thr Gln Pro Pro Ser Ala Ser Gly Thr Pro Gly Gln
1               5                   10                  15

Arg Val Thr Ile Ser Cys Gln Gly Asp Ser Leu Arg Ser Tyr Tyr Val
            20                  25                  30

Asn Trp Tyr Gln Gln Leu Pro Gly Thr Ala Pro Lys Leu Leu Ile Tyr
        35                  40                  45

Asp His Ser Lys Arg Pro Thr Gly Val Pro Asp Arg Phe Ser Gly Ser
    50                  55                  60

Lys Ser Gly Thr Ser Ala Ser Leu Ala Ile Ser Gly Leu Arg Ser Glu
65                  70                  75                  80

Asp Glu Ala Asp Tyr Tyr Cys Gln Ser Tyr Glu Ser Ser Thr Val Val
                85                  90                  95

Phe Gly Gly Gly Thr Lys Leu Thr Val Leu Gly
            100                 105

<210> SEQ ID NO 49
<211> LENGTH: 107
<212> TYPE: PRT
<213> ORGANISM: Artificial Sequence
<220> FEATURE:
<223> OTHER INFORMATION: Light chain variable region of 5A6 M4

<400> SEQUENCE: 49

Gln Ser Val Leu Thr Gln Pro Pro Ser Ala Ser Gly Thr Pro Gly Gln
1               5                   10                  15

Arg Val Thr Ile Ser Cys Gln Gly Asp Ser Leu Arg Ser Tyr Tyr Val
            20                  25                  30

Asn Trp Tyr Gln Gln Leu Pro Gly Thr Ala Pro Lys Leu Leu Ile Tyr
        35                  40                  45

Asp His Ser Lys Arg Pro Thr Gly Val Pro Asp Arg Phe Ser Gly Ser
    50                  55                  60

Lys Ser Gly Thr Ser Ala Ser Leu Ala Ile Ser Gly Leu Arg Ser Glu
65                  70                  75                  80

Asp Glu Ala Asp Tyr Tyr Cys Gln Ser Tyr Asp Ala Ser Thr Val Val
                85                  90                  95

Phe Gly Gly Gly Thr Lys Leu Thr Val Leu Gly
            100                 105

<210> SEQ ID NO 50
<211> LENGTH: 107
<212> TYPE: PRT
<213> ORGANISM: Artificial Sequence
<220> FEATURE:
<223> OTHER INFORMATION: Light chain variable region of 5A6 M5

<400> SEQUENCE: 50
```

-continued

```
Gln Ser Val Leu Thr Gln Pro Pro Ser Ala Ser Gly Thr Pro Gly Gln
1               5                   10                  15

Arg Val Thr Ile Ser Cys Gln Gly Glu Ser Leu Arg Ser Tyr Tyr Val
                20                  25                  30

Asn Trp Tyr Gln Gln Leu Pro Gly Thr Ala Pro Lys Leu Leu Ile Tyr
            35                  40                  45

Asp His Ser Lys Arg Pro Thr Gly Val Pro Asp Arg Phe Ser Gly Ser
        50                  55                  60

Lys Ser Gly Thr Ser Ala Ser Leu Ala Ile Ser Gly Leu Arg Ser Glu
65                  70                  75                  80

Asp Glu Ala Asp Tyr Tyr Cys Gln Ser Tyr Glu Ser Ser Thr Val Val
                85                  90                  95

Phe Gly Gly Gly Thr Lys Leu Thr Val Leu Gly
            100                 105
```

```
<210> SEQ ID NO 51
<211> LENGTH: 107
<212> TYPE: PRT
<213> ORGANISM: Artificial Sequence
<220> FEATURE:
<223> OTHER INFORMATION: Light chain variable region of 5A6 M6

<400> SEQUENCE: 51
```

```
Gln Ser Val Leu Thr Gln Pro Pro Ser Ala Ser Gly Thr Pro Gly Gln
1               5                   10                  15

Arg Val Thr Ile Ser Cys Gln Gly Glu Ser Leu Arg Ser Tyr Tyr Val
                20                  25                  30

Asn Trp Tyr Gln Gln Leu Pro Gly Thr Ala Pro Lys Leu Leu Ile Tyr
            35                  40                  45

Asp His Ser Lys Arg Pro Thr Gly Val Pro Asp Arg Phe Ser Gly Ser
        50                  55                  60

Lys Ser Gly Thr Ser Ala Ser Leu Ala Ile Ser Gly Leu Arg Ser Glu
65                  70                  75                  80

Asp Glu Ala Asp Tyr Tyr Cys Gln Ser Tyr Asp Ala Ser Thr Val Val
                85                  90                  95

Phe Gly Gly Gly Thr Lys Leu Thr Val Leu Gly
            100                 105
```

```
<210> SEQ ID NO 52
<211> LENGTH: 107
<212> TYPE: PRT
<213> ORGANISM: Artificial Sequence
<220> FEATURE:
<223> OTHER INFORMATION: Light chain variable region of 5A6 M7

<400> SEQUENCE: 52
```

```
Gln Ser Val Leu Thr Gln Pro Pro Ser Ala Ser Gly Thr Pro Gly Gln
1               5                   10                  15

Arg Val Thr Ile Ser Cys Gln Gly Asp Ala Leu Arg Ser Tyr Tyr Val
                20                  25                  30

Asn Trp Tyr Gln Gln Leu Pro Gly Thr Ala Pro Lys Leu Leu Ile Tyr
            35                  40                  45

Asp His Ser Lys Arg Pro Thr Gly Val Pro Asp Arg Phe Ser Gly Ser
        50                  55                  60

Lys Ser Gly Thr Ser Ala Ser Leu Ala Ile Ser Gly Leu Arg Ser Glu
65                  70                  75                  80

Asp Glu Ala Asp Tyr Tyr Cys Gln Ser Tyr Glu Ser Ser Thr Val Val
                85                  90                  95
```

-continued

```
Phe Gly Gly Gly Thr Lys Leu Thr Val Leu Gly
        100                 105

<210> SEQ ID NO 53
<211> LENGTH: 107
<212> TYPE: PRT
<213> ORGANISM: Artificial Sequence
<220> FEATURE:
<223> OTHER INFORMATION: Light chain variable region of 5A6 M8

<400> SEQUENCE: 53

Gln Ser Val Leu Thr Gln Pro Pro Ser Ala Ser Gly Thr Pro Gly Gln
1               5                   10                  15

Arg Val Thr Ile Ser Cys Gln Gly Asp Ala Leu Arg Ser Tyr Tyr Val
            20                  25                  30

Asn Trp Tyr Gln Gln Leu Pro Gly Thr Ala Pro Lys Leu Leu Ile Tyr
        35                  40                  45

Asp His Ser Lys Arg Pro Thr Gly Val Pro Asp Arg Phe Ser Gly Ser
    50                  55                  60

Lys Ser Gly Thr Ser Ala Ser Leu Ala Ile Ser Gly Leu Arg Ser Glu
65                  70                  75                  80

Asp Glu Ala Asp Tyr Tyr Cys Gln Ser Tyr Asp Ala Ser Thr Val Val
                85                  90                  95

Phe Gly Gly Gly Thr Lys Leu Thr Val Leu Gly
        100                 105

<210> SEQ ID NO 54
<211> LENGTH: 11
<212> TYPE: PRT
<213> ORGANISM: Artificial Sequence
<220> FEATURE:
<223> OTHER INFORMATION: Light chain CDR1 of 5D5 M1

<400> SEQUENCE: 54

Lys Ala Ser Gln Asp Ile Asp Asn Asp Ile Asn
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Light chain CDR1 of 5D5 M2

<400> SEQUENCE: 55

Lys Ala Ser Gln Asp Ile Asp Glu Asp Ile Asn
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Light chain CDR1 of 5D5 M3

<400> SEQUENCE: 56

Lys Ala Ser Gln Asp Ile Asp Ala Asp Ile Asn
1               5                   10

<210> SEQ ID NO 57
<211> LENGTH: 11
<212> TYPE: PRT
<213> ORGANISM: Artificial Sequence
```

<220> FEATURE:
<223> OTHER INFORMATION: Light chain CDR1 of 5D5 M4

<400> SEQUENCE: 57

Lys Ala Ser Gln Asp Ile Asp Asp Ala Ile Asn
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Light chain CDR1 of 5D5 M5

<400> SEQUENCE: 58

Lys Ala Ser Gln Asp Ile Asp Asp Glu Ile Asn
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Light chain CDR1 of 5A6 M1

<400> SEQUENCE: 59

Gln Gly Glu Ser Leu Arg Ser Tyr Tyr Val Asn
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Light chain CDR1 of 5A6 M2

<400> SEQUENCE: 60

Gln Gly Asp Ala Leu Arg Ser Tyr Tyr Val Asn
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Light chain CDR1 of 5A6 M5 and 5A6 M6

<400> SEQUENCE: 61

Gln Gly Glu Ser Leu Arg Ser Tyr Tyr Val Asn
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Light chain CDR1 of 5D5 M7 and 5D5 M8

<400> SEQUENCE: 62

Gln Gly Asp Ala Leu Arg Ser Tyr Tyr Val Asn
1               5                   10

<210> SEQ ID NO 63
<211> LENGTH: 8
<212> TYPE: PRT
<213> ORGANISM: Artificial Sequence
<220> FEATURE:

-continued

<223> OTHER INFORMATION: Light chain CDR3 of 5A6 M3, 5A6 M5, and 5A6 M7

<400> SEQUENCE: 63

Gln Ser Tyr Glu Ser Ser Thr Val
1               5

<210> SEQ ID NO 64
<211> LENGTH: 8
<212> TYPE: PRT
<213> ORGANISM: Artificial Sequence
<220> FEATURE:
<223> OTHER INFORMATION: Light chain CDR3 of 5A6 M4, 5A6 M6, and 5A6 M8

<400> SEQUENCE: 64

Gln Ser Tyr Asp Ala Ser Thr Val
1               5

<210> SEQ ID NO 65
<211> LENGTH: 121
<212> TYPE: PRT
<213> ORGANISM: Artificial Sequence
<220> FEATURE:
<223> OTHER INFORMATION: Heavy chain variable region of anti-4-1BB
      antibody 41B01

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
            35                  40                  45

Ser Trp Ile Ser Tyr Ser Gly Gly Ser Ile Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gln Arg Asn Ser Met Arg Glu Phe Asp Tyr Trp Gly
            100                 105                 110

Gln Gly Thr Leu Val Thr Val Ser Ser
        115                 120

<210> SEQ ID NO 66
<211> LENGTH: 121
<212> TYPE: PRT
<213> ORGANISM: Artificial Sequence
<220> FEATURE:
<223> OTHER INFORMATION: Heavy chain variable region of anti-4-1BB
      antibody 41B01 M4

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
            35                  40                  45

Ser Trp Ile Ser Tyr Ser Gly Gly Ser Ile Tyr Tyr Ala Asp Ser Val
        50                  55                  60

Lys Gly Arg Phe Thr Ile Ser Arg Asp Asn Ser Lys Asn Thr Leu Tyr

-continued

```
65                    70                    75                    80

Leu Gln Met Asn Ser Leu Arg Ala Glu Asp Thr Ala Val Tyr Tyr Cys
                    85                    90                    95

Ala Arg Asp Ala Gln Arg Asn Ser Met Arg Glu Phe Asp Tyr Trp Gly
                    100                   105                   110

Gln Gly Thr Leu Val Thr Val Ser Ser
        115                   120

<210> SEQ ID NO 67
<211> LENGTH: 121
<212> TYPE: PRT
<213> ORGANISM: Artificial Sequence
<220> FEATURE:
<223> OTHER INFORMATION: Heavy chain variable region of anti-4-1BB
      antibody 41B01 M11

<400> SEQUENCE: 67

Glu Val Gln Leu Leu Glu Ser Gly Gly Gly Leu Val Gln Pro Gly Gly
1                   5                     10                    15

Ser Leu Arg Leu Ser Cys Ala Ala Ser Gly Phe Thr Phe Ser Ser Tyr
                    20                    25                    30

Asp Met Ser Trp Val Arg Gln Ala Pro Gly Lys Gly Leu Glu Trp Val
                    35                    40                    45

Ser Trp Ile Ser Tyr Ser Gly Gly Ser Ile Tyr Tyr Ala Asp Ser Val
        50                    55                    60

Lys Gly Arg Phe Thr Ile Ser Arg Asp Asn Ser Lys Asn Thr Leu Tyr
65                  70                    75                    80

Leu Gln Met Asn Ser Leu Arg Ala Glu Asp Thr Ala Val Tyr Tyr Cys
                    85                    90                    95

Ala Arg Asp Ala Gln Gln Ser Met Arg Glu Phe Asp Tyr Trp Gly
                    100                   105                   110

Gln Gly Thr Leu Val Thr Val Ser Ser
        115                   120

<210> SEQ ID NO 68
<211> LENGTH: 121
<212> TYPE: PRT
<213> ORGANISM: Artificial Sequence
<220> FEATURE:
<223> OTHER INFORMATION: Heavy chain variable region of anti-4-1BB
      antibody 41B01 M12

<400> SEQUENCE: 68

Glu Val Gln Leu Leu Glu Ser Gly Gly Gly Leu Val Gln Pro Gly Gly
1                   5                     10                    15

Ser Leu Arg Leu Ser Cys Ala Ala Ser Gly Phe Thr Phe Ser Ser Tyr
                    20                    25                    30

Asp Met Ser Trp Val Arg Gln Ala Pro Gly Lys Gly Leu Glu Trp Val
                    35                    40                    45

Ser Trp Ile Ser Tyr Ser Gly Gly Ser Ile Tyr Tyr Ala Asp Ser Val
        50                    55                    60

Lys Gly Arg Phe Thr Ile Ser Arg Asp Asn Ser Lys Asn Thr Leu Tyr
65                  70                    75                    80

Leu Gln Met Asn Ser Leu Arg Ala Glu Asp Thr Ala Val Tyr Tyr Cys
                    85                    90                    95

Ala Arg Asp Ala Gln Arg Asn Ser Met Arg Glu Phe Asp Tyr Trp Gly
                    100                   105                   110

Gln Gly Thr Leu Val Thr Val Ser Ser
```

```
         115                          120
```

```
<210> SEQ ID NO 69
<211> LENGTH: 121
<212> TYPE: PRT
<213> ORGANISM: Artificial Sequence
<220> FEATURE:
<223> OTHER INFORMATION: Heavy chain variable region of anti-4-1BB
      antibody 41B01 M13

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Gln Ser Met Arg Glu Phe Asp Tyr Trp Gly
            100                 105                 110

Gln Gly Thr Leu Val Thr Val Ser Ser
        115                 120

<210> SEQ ID NO 70
<211> LENGTH: 127
<212> TYPE: PRT
<213> ORGANISM: Artificial Sequence
<220> FEATURE:
<223> OTHER INFORMATION: Heavy chain variable region of anti-4-1BB
      antibody 41B02

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Gly Leu Glu Trp Val
        35                  40                  45

Ser Val Ile Tyr Pro Asp Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys His Gly Gly Gln Lys Pro Thr Thr Lys Ser Ser Ser Ala Tyr
            100                 105                 110

Gly Met Asp Gly Trp Gly Gln Gly Thr Leu Val Thr Val Ser Ser
        115                 120                 125

<210> SEQ ID NO 71
<211> LENGTH: 127
<212> TYPE: PRT
<213> ORGANISM: Artificial Sequence
<220> FEATURE:
<223> OTHER INFORMATION: Heavy chain variable region of anti-4-1BB
```

-continued antibody 41B02 M1

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Gly Leu Glu Trp Val
        35                  40                  45

Ser Val Ile Tyr Pro Asp Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Gly Gly Gln Lys Pro Thr Thr Lys Ser Ser Ser Ala Tyr
            100                 105                 110

Gly Met Asp Gly Trp Gly Gln Gly Thr Leu Val Thr Val Ser Ser
        115                 120                 125

<210> SEQ ID NO 72
<211> LENGTH: 119
<212> TYPE: PRT
<213> ORGANISM: Artificial Sequence
<220> FEATURE:
<223> OTHER INFORMATION: Heavy chain variable region of anti-4-1BB
      antibody AB41

<400> SEQUENCE: 72

Gln Val Gln Leu Gln Gln Ser Gly Ala Glu Val Ile Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Arg Gln Ala Pro Gly Gln Gly Leu Glu Trp Ile
        35                  40                  45

Gly Glu Ile Asn Pro Gly Asn Gly His Thr Asn Tyr Asn Glu Lys Phe
    50                  55                  60

Lys Ser Arg Ala Thr Leu Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Phe Thr Thr Ala Arg Ala Phe Ala Tyr Trp Gly Gln Gly
            100                 105                 110

Thr Leu Val Thr Val Ser Ser
        115

<210> SEQ ID NO 73
<211> LENGTH: 111
<212> TYPE: PRT
<213> ORGANISM: Artificial Sequence
<220> FEATURE:
<223> OTHER INFORMATION: Light chain variable region of anti-4-1BB
      antibody 41B01

<400> SEQUENCE: 73

Gln Ser Val Leu Thr Gln Pro Pro Ser Ala Ser Gly Thr Pro Gly Arg
1               5                   10                  15

Arg Val Thr Ile Ser Cys Ser Gly Ser Ser Ser Asn Ile Gly Asn Asn
            20                  25                  30

-continued

```
Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu Gly
            100                 105                 110
```

```
<210> SEQ ID NO 74
<211> LENGTH: 111
<212> TYPE: PRT
<213> ORGANISM: Artificial Sequence
<220> FEATURE:
<223> OTHER INFORMATION: Light chain variable region of anti-4-1BB
      antibody 41B01 M4

<400> SEQUENCE: 74
```

```
Gln Ser Val Leu Thr Gln Pro Pro Ser Ala Ser Gly Thr Pro Gly Arg
1                   5                   10                  15

Arg Val Thr Ile Ser Cys Ser Gly Ser Ser Ser Asn Ile Gly Asn Asn
                20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu Gly
            100                 105                 110
```

```
<210> SEQ ID NO 75
<211> LENGTH: 111
<212> TYPE: PRT
<213> ORGANISM: Artificial Sequence
<220> FEATURE:
<223> OTHER INFORMATION: Light chain variable region of anti-4-1BB
      antibody 41B01 M11

<400> SEQUENCE: 75
```

```
Gln Ser Val Leu Thr Gln Pro Pro Ser Ala Ser Gly Thr Pro Gly Arg
1                   5                   10                  15

Arg Val Thr Ile Ser Cys Ser Gly Ser Ser Ser Asn Ile Gly Asn Asn
                20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu Gly
            100                 105                 110
```

-continued

```
<210> SEQ ID NO 76
<211> LENGTH: 111
<212> TYPE: PRT
<213> ORGANISM: Artificial Sequence
<220> FEATURE:
<223> OTHER INFORMATION: Light chain variable region of anti-4-1BB
      antibody 41B01 M12

<400> SEQUENCE: 76

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu Gly
            100                 105                 110

<210> SEQ ID NO 77
<211> LENGTH: 111
<212> TYPE: PRT
<213> ORGANISM: Artificial Sequence
<220> FEATURE:
<223> OTHER INFORMATION: Light chain variable region of anti-4-1BB
      antibody 41B01 M13

<400> SEQUENCE: 77

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu Gly
            100                 105                 110

<210> SEQ ID NO 78
<211> LENGTH: 111
<212> TYPE: PRT
<213> ORGANISM: Artificial Sequence
<220> FEATURE:
<223> OTHER INFORMATION: Light chain variable region of anti-4-1BB
      antibody 41B02

<400> SEQUENCE: 78

Gln Ser Val Leu Thr Gln Pro Pro Ser Ala Ser Gly Thr Pro Gly Arg
1               5                   10                  15
```

Arg Val Thr Ile Ser Cys Ser Gly Ser Ser Ser Asn Ile Gly Asn Asn
              20                  25                  30

Tyr Val Thr Trp Tyr Gln Gln Leu Pro Gly Thr Ala Pro Lys Leu Leu
              35                  40                  45

Ile Tyr Ala Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                  85                  90                  95

Ser Gly Tyr Val Phe Gly Gly Gly Thr Lys Leu Thr Val Leu Gly
              100                 105                 110

<210> SEQ ID NO 79
<211> LENGTH: 111
<212> TYPE: PRT
<213> ORGANISM: Artificial Sequence
<220> FEATURE:
<223> OTHER INFORMATION: Light chain variable region of anti-4-1BB
      antibody 41B02 M1

<400> SEQUENCE: 79

Gln Ser Val Leu Thr Gln Pro Pro Ser Ala Ser Gly Thr Pro Gly Gln
1                   5                   10                  15

Arg Val Thr Ile Ser Cys Ser Gly Ser Ser Ser Asn Ile Gly Asn Asn
              20                  25                  30

Tyr Val Thr Trp Tyr Gln Gln Leu Pro Gly Thr Ala Pro Lys Leu Leu
              35                  40                  45

Ile Tyr Ala Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                  85                  90                  95

Ser Gly Tyr Val Phe Gly Gly Gly Thr Lys Leu Thr Val Leu Gly
              100                 105                 110

<210> SEQ ID NO 80
<211> LENGTH: 108
<212> TYPE: PRT
<213> ORGANISM: Artificial Sequence
<220> FEATURE:
<223> OTHER INFORMATION: Light chain variable region of anti-4-1BB
      antibody AB41

<400> SEQUENCE: 80

Asp Ile Val Met Thr Gln Ser Pro Ala Phe Leu Ser Val Thr Pro Gly
1                   5                   10                  15

Glu Lys Val Thr Ile Thr Cys Arg Ala Ser Gln Thr Ile Ser Asp Tyr
              20                  25                  30

Leu His Trp Tyr Gln Gln Lys Pro Asp Gln Ala Pro Lys Leu Leu Ile
              35                  40                  45

Lys Tyr Ala Ser Gln Ser Ile Ser Gly Ile Pro Ser Arg Phe Ser Gly
        50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Asp Gly His Ser Phe Pro Pro
                  85                  90                  95

-continued

```
Thr Phe Gly Gln Gly Thr Lys Leu Glu Ile Lys Arg
            100                 105

<210> SEQ ID NO 81
<211> LENGTH: 5
<212> TYPE: PRT
<213> ORGANISM: Artificial Sequence
<220> FEATURE:
<223> OTHER INFORMATION: Heavy chain CDR1 of 41B01, 41B01 M4, 41B01 M11,
      41B01 M12, and 41B01 M13

<400> SEQUENCE: 81

Ser Tyr Asp Met Ser
1               5

<210> SEQ ID NO 82
<211> LENGTH: 5
<212> TYPE: PRT
<213> ORGANISM: Artificial Sequence
<220> FEATURE:
<223> OTHER INFORMATION: Heavy chain CDR1 of 41B02 and 41B02 M1

<400> SEQUENCE: 82

Gly Tyr Asp Met Ser
1               5

<210> SEQ ID NO 83
<211> LENGTH: 5
<212> TYPE: PRT
<213> ORGANISM: Artificial Sequence
<220> FEATURE:
<223> OTHER INFORMATION: Heavy chain CDR1 of AB41

<400> SEQUENCE: 83

Ser Tyr Trp Met His
1               5

<210> SEQ ID NO 84
<211> LENGTH: 17
<212> TYPE: PRT
<213> ORGANISM: Artificial Sequence
<220> FEATURE:
<223> OTHER INFORMATION: Heavy chain CDR2 of 41B01, 41B01 M4, 41B01 M11,
      41B01 M12, and 41B01 M13

<400> SEQUENCE: 84

Trp Ile Ser Tyr Ser Gly Gly Ser Ile Tyr Tyr Ala Asp Ser Val Lys
1               5                   10                  15

Gly

<210> SEQ ID NO 85
<211> LENGTH: 17
<212> TYPE: PRT
<213> ORGANISM: Artificial Sequence
<220> FEATURE:
<223> OTHER INFORMATION: Heavy chain CDR2 of 41B02 and 41B02 M1

<400> SEQUENCE: 85

Val Ile Tyr Pro Asp Asp Gly Asn Thr Tyr Tyr Ala Asp Ser Val Lys
1               5                   10                  15

Gly

<210> SEQ ID NO 86
<211> LENGTH: 17
<212> TYPE: PRT
<213> ORGANISM: Artificial Sequence
```

-continued

```
<220> FEATURE:
<223> OTHER INFORMATION: Heavy chain CDR2 of AB41

<400> SEQUENCE: 86

Glu Ile Asn Pro Gly Asn Gly His Thr Asn Tyr Asn Glu Lys Phe Lys
1               5                   10                  15

Ser

<210> SEQ ID NO 87
<211> LENGTH: 12
<212> TYPE: PRT
<213> ORGANISM: Artificial Sequence
<220> FEATURE:
<223> OTHER INFORMATION: Heavy chain CDR3 of 41B01

<400> SEQUENCE: 87

Asp Gly Gln Arg Asn Ser Met Arg Glu Phe Asp Tyr
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Heavy chain CDR3 of 41B01 M4 and 41B01 M12

<400> SEQUENCE: 88

Asp Ala Gln Arg Asn Ser Met Arg Glu Phe Asp Tyr
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Heavy chain CDR3 of 41B01 M11 and 41B01 M13

<400> SEQUENCE: 89

Asp Ala Gln Arg Gln Ser Met Arg Glu Phe Asp Tyr
1               5                   10

<210> SEQ ID NO 90
<211> LENGTH: 18
<212> TYPE: PRT
<213> ORGANISM: Artificial Sequence
<220> FEATURE:
<223> OTHER INFORMATION: Heavy chain CDR3 of 41B02 and 41B02 M1

<400> SEQUENCE: 90

His Gly Gly Gln Lys Pro Thr Thr Lys Ser Ser Ser Ala Tyr Gly Met
1               5                   10                  15

Asp Gly

<210> SEQ ID NO 91
<211> LENGTH: 10
<212> TYPE: PRT
<213> ORGANISM: Artificial Sequence
<220> FEATURE:
<223> OTHER INFORMATION: Heavy chain CDR3 of AB41

<400> SEQUENCE: 91

Ser Phe Thr Thr Ala Arg Ala Phe Ala Tyr
1               5                   10

<210> SEQ ID NO 92
```

-continued

```
<211> LENGTH: 13
<212> TYPE: PRT
<213> ORGANISM: Artificial Sequence
<220> FEATURE:
<223> OTHER INFORMATION: Light chain CDR1 of 41B01, 41B01 M4, 41B01 M11,
      41B01 M12, 41B01 M13, 41B02, and 41B02 M1

<400> SEQUENCE: 92

Ser Gly Ser Ser Ser Asn Ile Gly Asn Asn Tyr Val Thr
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Light chain CDR1 of AB41

<400> SEQUENCE: 93

Arg Ala Ser Gln Thr Ile Ser Asp Tyr Leu His
1               5                   10

<210> SEQ ID NO 94
<211> LENGTH: 7
<212> TYPE: PRT
<213> ORGANISM: Artificial Sequence
<220> FEATURE:
<223> OTHER INFORMATION: Light chain CDR2 of 41B01, 41B01 M4, 41B01 M11,
      41B01 M12, 41B01 M13, 41B02, and 41B02 M1

<400> SEQUENCE: 94

Ala Asp Ser His Arg Pro Ser
1               5

<210> SEQ ID NO 95
<211> LENGTH: 7
<212> TYPE: PRT
<213> ORGANISM: Artificial Sequence
<220> FEATURE:
<223> OTHER INFORMATION: Light chain CDR2 of AB41

<400> SEQUENCE: 95

Tyr Ala Ser Gln Ser Ile Ser
1               5

<210> SEQ ID NO 96
<211> LENGTH: 11
<212> TYPE: PRT
<213> ORGANISM: Artificial Sequence
<220> FEATURE:
<223> OTHER INFORMATION: Light chain CDR3 of 41B01, 41B01 M4, 41B01 M11,
      41B01 M12, 41B01 M13, 41B02, and 41B02 M1

<400> SEQUENCE: 96

Ala Thr Trp Asp Tyr Ser Leu Ser Gly Tyr Val
1               5                   10

<210> SEQ ID NO 97
<211> LENGTH: 9
<212> TYPE: PRT
<213> ORGANISM: Artificial Sequence
<220> FEATURE:
<223> OTHER INFORMATION: Light chain CDR3 of AB41

<400> SEQUENCE: 97

Gln Asp Gly His Ser Phe Pro Pro Thr
1               5
```

<210> SEQ ID NO 98
<211> LENGTH: 20
<212> TYPE: PRT
<213> ORGANISM: Artificial Sequence
<220> FEATURE:
<223> OTHER INFORMATION: Linker (GGGGS)4

<400> SEQUENCE: 98

Gly Gly Gly Gly Ser Gly Gly Gly Gly Ser Gly Gly Gly Gly Ser Gly
1               5                   10                  15

Gly Gly Gly Ser
            20

<210> SEQ ID NO 99
<211> LENGTH: 18
<212> TYPE: PRT
<213> ORGANISM: Artificial Sequence
<220> FEATURE:
<223> OTHER INFORMATION: Linker (GS)9

<400> SEQUENCE: 99

Gly Ser Gly Ser Gly Ser Gly Ser Gly Ser Gly Ser Gly Ser Gly Ser
1               5                   10                  15

Gly Ser

<210> SEQ ID NO 100
<211> LENGTH: 451
<212> TYPE: PRT
<213> ORGANISM: Artificial Sequence
<220> FEATURE:
<223> OTHER INFORMATION: BCMA-Heavy Chain of B58 antibody

<400> SEQUENCE: 100

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
        35                  40                  45

Ser Trp Ile Tyr Pro Ser Asp Ser Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Phe Ala Asn Lys Tyr Arg Gln Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

-continued

```
Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

```
<210> SEQ ID NO 101
<211> LENGTH: 216
<212> TYPE: PRT
<213> ORGANISM: Artificial Sequence
<220> FEATURE:
<223> OTHER INFORMATION: BCMA-Light Chain of B58 antibody

<400> SEQUENCE: 101
```

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Ser Val Ser Trp Tyr Gln Gln Leu Pro Gly Thr Ala Pro Lys Leu Leu
        35                  40                  45

Ile Tyr Ala Asp Ser Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Gly Tyr Val Phe Gly Gly Gly Thr Lys Leu Thr Val Leu Gly Gln
            100                 105                 110
```

-continued

```
Pro Lys Ala Ala Pro Ser Val Thr Leu Phe Pro Pro Ser Ser Glu Glu
        115             120             125

Leu Gln Ala Asn Lys Ala Thr Leu Val Cys Leu Ile Ser Asp Phe Tyr
        130             135             140

Pro Gly Ala Val Thr Val Ala Trp Lys Ala Asp Ser Ser Pro Val Lys
145             150             155             160

Ala Gly Val Glu Thr Thr Thr Pro Ser Lys Gln Ser Asn Asn Lys Tyr
                165             170             175

Ala Ala Ser Ser Tyr Leu Ser Leu Thr Pro Glu Gln Trp Lys Ser His
            180             185             190

Arg Ser Tyr Ser Cys Gln Val Thr His Glu Gly Ser Thr Val Glu Lys
        195             200             205

Thr Val Ala Pro Ala Glu Cys Ser
    210             215
```

```
<210> SEQ ID NO 102
<211> LENGTH: 446
<212> TYPE: PRT
<213> ORGANISM: Artificial Sequence
<220> FEATURE:
<223> OTHER INFORMATION: BCMA-Heavy Chain of 5B5 antibody

<400> SEQUENCE: 102
```

```
Glu Val Gln Leu Leu Glu Ser Gly Gly Gly Leu Val Gln Pro Gly Gly
1               5               10              15

Ser Leu Arg Leu Ser Cys Ala Ala Ser Gly Phe Thr Phe Ser Gly His
        20              25              30

Tyr Trp Ser Trp Val Arg Gln Ala Pro Gly Lys Gly Leu Glu Trp Val
        35              40              45

Ser Thr Val Ser Gly Ser Gly Gly Asp Thr Phe Tyr Ala Asp Ser Val
        50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Arg Gly His Ser Val Met Asp Val Trp Gly Gln Gly Thr Leu Val
            100             105             110

Thr Val Ser Ser Ala Ser Thr Lys Gly Pro Ser Val Phe Pro Leu Ala
        115             120             125

Pro Ser Ser Lys Ser Thr Ser Gly Gly Thr Ala Ala Leu Gly Cys Leu
        130             135             140

Val Lys Asp Tyr Phe Pro Glu Pro Val Thr Val Ser Trp Asn Ser Gly
145             150             155             160

Ala Leu Thr Ser Gly Val His Thr Phe Pro Ala Val Leu Gln Ser Ser
                165             170             175

Gly Leu Tyr Ser Leu Ser Ser Val Val Thr Val Pro Ser Ser Ser Leu
            180             185             190

Gly Thr Gln Thr Tyr Ile Cys Asn Val Asn His Lys Pro Ser Asn Thr
        195             200             205

Lys Val Asp Lys Lys Val Glu Pro Lys Ser Cys Asp Lys Thr His Thr
        210             215             220

Cys Pro Pro Cys Pro Ala Pro Glu Leu Leu Gly Gly Pro Ser Val Phe
225             230             235             240

Leu Phe Pro Pro Lys Pro Lys Asp Thr Leu Met Ile Ser Arg Thr Pro
                245             250             255
```

-continued

```
Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Ala Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445
```

```
<210> SEQ ID NO 103
<211> LENGTH: 214
<212> TYPE: PRT
<213> ORGANISM: Artificial Sequence
<220> FEATURE:
<223> OTHER INFORMATION: BCMA-Light Chain of 5B5 antibody

<400> SEQUENCE: 103
```

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Ile Asp Ser Tyr
            20                  25                  30

Val Ala Trp Tyr Gln Gln Lys Pro Gly Gln Ala Pro Arg Leu Leu Ile
            35                  40                  45

Tyr Asp Ala Ser Leu Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asn Ser Trp Pro Ile
            85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 104
<211> LENGTH: 446
<212> TYPE: PRT
<213> ORGANISM: Artificial Sequence
<220> FEATURE:
<223> OTHER INFORMATION: BCMA-Heavy Chain of 5D5, 5D5 M1, 5D5 M2, 5D5
      M3, and 5D5 M4

<400> SEQUENCE: 104

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Leu Ser Trp Val Arg Gln Ala Pro Gly Lys Gly Leu Glu Trp Val
        35                  40                  45

Ser Leu Ile Asp Ser Ser Gly Ser Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu His Gly Leu Phe Asp Ser Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Ala Ser Thr Tyr Arg Val Val Ser Val
    290                 295                 300

Leu Thr Val Leu His Gln Asp Trp Leu Asn Gly Lys Glu Tyr Lys Cys
```

```
305                 310                 315                 320
Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 105
<211> LENGTH: 214
<212> TYPE: PRT
<213> ORGANISM: Artificial Sequence
<220> FEATURE:
<223> OTHER INFORMATION: BCMA-Light Chain of 5D5 antibody

<400> SEQUENCE: 105

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Asp Ile Asp Asp Asp
                20                  25                  30

Ile Asn Trp Tyr Gln Gln Lys Pro Gly Gln Ala Pro Arg Leu Leu Ile
                35                  40                  45

Tyr Asp Ala Ser Leu Arg Ala Thr Gly Ile Pro Asp Arg Phe Ser Gly
                50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Leu Arg Thr Pro Ile
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210
```

-continued

```
<210> SEQ ID NO 106
<211> LENGTH: 214
<212> TYPE: PRT
<213> ORGANISM: Artificial Sequence
<220> FEATURE:
<223> OTHER INFORMATION: BCMA-Light Chain of 5D5 M1 antibody

<400> SEQUENCE: 106

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Asp Ile Asp Asn Asp
            20                  25                  30

Ile Asn Trp Tyr Gln Gln Lys Pro Gly Gln Ala Pro Arg Leu Leu Ile
        35                  40                  45

Tyr Asp Ala Ser Leu Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Leu Arg Thr Pro Ile
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 107
<211> LENGTH: 214
<212> TYPE: PRT
<213> ORGANISM: Artificial Sequence
<220> FEATURE:
<223> OTHER INFORMATION: BCMA-Light Chain of 5D5 M2 antibody

<400> SEQUENCE: 107

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Asp Ile Asp Glu Asp
            20                  25                  30

Ile Asn Trp Tyr Gln Gln Lys Pro Gly Gln Ala Pro Arg Leu Leu Ile
        35                  40                  45

Tyr Asp Ala Ser Leu Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Leu Arg Thr Pro Ile
                85                  90                  95
```

-continued

```
Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 108
<211> LENGTH: 214
<212> TYPE: PRT
<213> ORGANISM: Artificial Sequence
<220> FEATURE:
<223> OTHER INFORMATION: BCMA-Light Chain of 5D5 M3 antibody

<400> SEQUENCE: 108

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Asp Ile Asp Ala Asp
            20                  25                  30

Ile Asn Trp Tyr Gln Gln Lys Pro Gly Gln Ala Pro Arg Leu Leu Ile
            35                  40                  45

Tyr Asp Ala Ser Leu Arg Ala Thr Gly Ile Pro Asp Arg Phe Ser Gly
            50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Leu Arg Thr Pro Ile
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 109
<211> LENGTH: 214
```

```
<212> TYPE: PRT
<213> ORGANISM: Artificial Sequence
<220> FEATURE:
<223> OTHER INFORMATION: BCMA-Light Chain of 5D5 M4 antibody

<400> SEQUENCE: 109

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Asp Ile Asp Asp Ala
            20                  25                  30

Ile Asn Trp Tyr Gln Gln Lys Pro Gly Gln Ala Pro Arg Leu Leu Ile
        35                  40                  45

Tyr Asp Ala Ser Leu Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Leu Arg Thr Pro Ile
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 110
<211> LENGTH: 214
<212> TYPE: PRT
<213> ORGANISM: Artificial Sequence
<220> FEATURE:
<223> OTHER INFORMATION: BCMA-Light Chain of 5D5 M5 antibody

<400> SEQUENCE: 110

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Asp Ile Asp Asp Glu
            20                  25                  30

Ile Asn Trp Tyr Gln Gln Lys Pro Gly Gln Ala Pro Arg Leu Leu Ile
        35                  40                  45

Tyr Asp Ala Ser Leu Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Leu Arg Thr Pro Ile
                85                  90                  95

Thr Phe Gly Gln Gly Thr Lys Leu Glu Ile Lys Arg Thr Val Ala Ala
                100                 105                 110
```

-continued

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 111
<211> LENGTH: 447
<212> TYPE: PRT
<213> ORGANISM: Artificial Sequence
<220> FEATURE:
<223> OTHER INFORMATION: BCMA-Heavy Chain of 5A6, 5A6 M1, 5A6 M2, 5A6
      M3, 5A6 M4, 5A6 M5, 5A6 M6, 5A6 M7, and 5A6 M8

<400> SEQUENCE: 111
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
        20                  25                  30

Gly Val His Trp Val Arg Gln Ala Pro Gly Lys Gly Leu Glu Trp Val
        35                  40                  45

Ser Tyr Ile Ser Tyr Ser Gly Gly Thr Tyr Tyr Asn Pro Ser Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Ser Asp Asp Phe Gly Phe Asp Tyr Trp Gly Gln Gly Thr Leu
                100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
```

-continued

```
                  245                    250                    255
Pro Glu Val Thr Cys Val Val Val Asp Val Ser His Glu Asp Pro Glu
              260                    265                    270

Val Lys Phe Asn Trp Tyr Val Asp Gly Val Glu Val His Asn Ala Lys
              275                    280                    285

Thr Lys Pro Arg Glu Glu Gln Tyr Ala Ser Thr Tyr Arg Val Val Ser
              290                    295                    300

Val Leu Thr Val Leu His Gln Asp Trp Leu Asn Gly Lys Glu Tyr Lys
305                    310                    315                    320

Cys Lys Val Ser Asn Lys Ala Leu Pro Ala Pro Ile Glu Lys Thr Ile
                  325                    330                    335

Ser Lys Ala Lys Gly Gln Pro Arg Glu Pro Gln Val Tyr Thr Leu Pro
              340                    345                    350

Pro Ser Arg Glu Glu Met Thr Lys Asn Gln Val Ser Leu Thr Cys Leu
              355                    360                    365

Val Lys Gly Phe Tyr Pro Ser Asp Ile Ala Val Glu Trp Glu Ser Asn
              370                    375                    380

Gly Gln Pro Glu Asn Asn Tyr Lys Thr Thr Pro Pro Val Leu Asp Ser
385                    390                    395                    400

Asp Gly Ser Phe Phe Leu Tyr Ser Lys Leu Thr Val Asp Lys Ser Arg
                  405                    410                    415

Trp Gln Gln Gly Asn Val Phe Ser Cys Ser Val Met His Glu Ala Leu
              420                    425                    430

His Asn His Tyr Thr Gln Lys Ser Leu Ser Leu Ser Pro Gly Lys
              435                    440                    445

<210> SEQ ID NO 112
<211> LENGTH: 212
<212> TYPE: PRT
<213> ORGANISM: Artificial Sequence
<220> FEATURE:
<223> OTHER INFORMATION: BCMA-Light Chain of 5A6 antibody

<400> SEQUENCE: 112

Gln Ser Val Leu Thr Gln Pro Pro Ser Ala Ser Gly Thr Pro Gly Gln
1                  5                    10                    15

Arg Val Thr Ile Ser Cys Gln Gly Asp Ser Leu Arg Ser Tyr Tyr Val
              20                    25                    30

Asn Trp Tyr Gln Gln Leu Pro Gly Thr Ala Pro Lys Leu Leu Ile Tyr
              35                    40                    45

Asp His Ser Lys Arg Pro Thr Gly Val Pro Asp Arg Phe Ser Gly Ser
              50                    55                    60

Lys Ser Gly Thr Ser Ala Ser Leu Ala Ile Ser Gly Leu Arg Ser Glu
65                    70                    75                    80

Asp Glu Ala Asp Tyr Tyr Cys Gln Ser Tyr Asp Ser Ser Thr Val Val
                  85                    90                    95

Phe Gly Gly Gly Thr Lys Leu Thr Val Leu Gly Gln Pro Lys Ala Ala
              100                    105                    110

Pro Ser Val Thr Leu Phe Pro Pro Ser Ser Glu Glu Leu Gln Ala Asn
              115                    120                    125

Lys Ala Thr Leu Val Cys Leu Ile Ser Asp Phe Tyr Pro Gly Ala Val
              130                    135                    140

Thr Val Ala Trp Lys Ala Asp Ser Ser Pro Val Lys Ala Gly Val Glu
145                    150                    155                    160

Thr Thr Thr Pro Ser Lys Gln Ser Asn Asn Lys Tyr Ala Ala Ser Ser
```

-continued

```
                   165                 170                 175
Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Ala Glu Cys Ser
    210

<210> SEQ ID NO 113
<211> LENGTH: 212
<212> TYPE: PRT
<213> ORGANISM: Artificial Sequence
<220> FEATURE:
<223> OTHER INFORMATION: BCMA-Light Chain of 5A6 M1 antibody

<400> SEQUENCE: 113

Gln Ser Val Leu Thr Gln Pro Pro Ser Ala Ser Gly Thr Pro Gly Gln
1               5                   10                  15

Arg Val Thr Ile Ser Cys Gln Gly Glu Ser Leu Arg Ser Tyr Tyr Val
            20                  25                  30

Asn Trp Tyr Gln Gln Leu Pro Gly Thr Ala Pro Lys Leu Leu Ile Tyr
        35                  40                  45

Asp His Ser Lys Arg Pro Thr Gly Val Pro Asp Arg Phe Ser Gly Ser
    50                  55                  60

Lys Ser Gly Thr Ser Ala Ser Leu Ala Ile Ser Gly Leu Arg Ser Glu
65                  70                  75                  80

Asp Glu Ala Asp Tyr Tyr Cys Gln Ser Tyr Asp Ser Ser Thr Val Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Ala Glu Cys Ser
    210

<210> SEQ ID NO 114
<211> LENGTH: 212
<212> TYPE: PRT
<213> ORGANISM: Artificial Sequence
<220> FEATURE:
<223> OTHER INFORMATION: BCMA-Light Chain of 5A6 M2 antibody

<400> SEQUENCE: 114

Gln Ser Val Leu Thr Gln Pro Pro Ser Ala Ser Gly Thr Pro Gly Gln
1               5                   10                  15

Arg Val Thr Ile Ser Cys Gln Gly Asp Ala Leu Arg Ser Tyr Tyr Val
            20                  25                  30
```

-continued

```
Asn Trp Tyr Gln Gln Leu Pro Gly Thr Ala Pro Lys Leu Leu Ile Tyr
    35                  40              45

Asp His Ser Lys Arg Pro Thr Gly Val Pro Asp Arg Phe Ser Gly Ser
    50                  55              60

Lys Ser Gly Thr Ser Ala Ser Leu Ala Ile Ser Gly Leu Arg Ser Glu
65                  70              75                  80

Asp Glu Ala Asp Tyr Tyr Cys Gln Ser Tyr Asp Ser Ser Thr Val Val
                85              90                  95

Phe Gly Gly Gly Thr Lys Leu Thr Val Leu Gly Gln Pro Lys Ala Ala
            100             105             110

Pro Ser Val Thr Leu Phe Pro Pro Ser Ser Glu Glu Leu Gln Ala Asn
            115             120             125

Lys Ala Thr Leu Val Cys Leu Ile Ser Asp Phe Tyr Pro Gly Ala Val
    130             135             140

Thr Val Ala Trp Lys Ala Asp Ser Ser Pro Val Lys Ala Gly Val Glu
145             150             155             160

Thr Thr Thr Pro Ser Lys Gln Ser Asn Asn Lys Tyr Ala Ala Ser Ser
                165             170             175

Tyr Leu Ser Leu Thr Pro Glu Gln Trp Lys Ser His Arg Ser Tyr Ser
            180             185             190

Cys Gln Val Thr His Glu Gly Ser Thr Val Glu Lys Thr Val Ala Pro
            195             200             205

Ala Glu Cys Ser
    210

<210> SEQ ID NO 115
<211> LENGTH: 212
<212> TYPE: PRT
<213> ORGANISM: Artificial Sequence
<220> FEATURE:
<223> OTHER INFORMATION: BCMA-Light Chain of 5A6 M3 antibody

<400> SEQUENCE: 115

Gln Ser Val Leu Thr Gln Pro Pro Ser Ala Ser Gly Thr Pro Gly Gln
1               5               10              15

Arg Val Thr Ile Ser Cys Gln Gly Asp Ser Leu Arg Ser Tyr Tyr Val
            20              25              30

Asn Trp Tyr Gln Gln Leu Pro Gly Thr Ala Pro Lys Leu Leu Ile Tyr
    35                  40              45

Asp His Ser Lys Arg Pro Thr Gly Val Pro Asp Arg Phe Ser Gly Ser
    50                  55              60

Lys Ser Gly Thr Ser Ala Ser Leu Ala Ile Ser Gly Leu Arg Ser Glu
65                  70              75                  80

Asp Glu Ala Asp Tyr Tyr Cys Gln Ser Tyr Glu Ser Ser Thr Val Val
                85              90                  95

Phe Gly Gly Gly Thr Lys Leu Thr Val Leu Gly Gln Pro Lys Ala Ala
            100             105             110

Pro Ser Val Thr Leu Phe Pro Pro Ser Ser Glu Glu Leu Gln Ala Asn
            115             120             125

Lys Ala Thr Leu Val Cys Leu Ile Ser Asp Phe Tyr Pro Gly Ala Val
    130             135             140

Thr Val Ala Trp Lys Ala Asp Ser Ser Pro Val Lys Ala Gly Val Glu
145             150             155             160

Thr Thr Thr Pro Ser Lys Gln Ser Asn Asn Lys Tyr Ala Ala Ser Ser
                165             170             175
```

```
Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Ala Glu Cys Ser
    210

<210> SEQ ID NO 116
<211> LENGTH: 212
<212> TYPE: PRT
<213> ORGANISM: Artificial Sequence
<220> FEATURE:
<223> OTHER INFORMATION: BCMA-Light Chain of 5A6 M4 antibody

<400> SEQUENCE: 116

Gln Ser Val Leu Thr Gln Pro Pro Ser Ala Ser Gly Thr Pro Gly Gln
1               5                   10                  15

Arg Val Thr Ile Ser Cys Gln Gly Asp Ser Leu Arg Ser Tyr Tyr Val
            20                  25                  30

Asn Trp Tyr Gln Gln Leu Pro Gly Thr Ala Pro Lys Leu Leu Ile Tyr
        35                  40                  45

Asp His Ser Lys Arg Pro Thr Gly Val Pro Asp Arg Phe Ser Gly Ser
    50                  55                  60

Lys Ser Gly Thr Ser Ala Ser Leu Ala Ile Ser Gly Leu Arg Ser Glu
65                  70                  75                  80

Asp Glu Ala Asp Tyr Tyr Cys Gln Ser Tyr Asp Ala Ser Thr Val Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Ala Glu Cys Ser
    210

<210> SEQ ID NO 117
<211> LENGTH: 212
<212> TYPE: PRT
<213> ORGANISM: Artificial Sequence
<220> FEATURE:
<223> OTHER INFORMATION: BCMA-Light Chain of 5A6 M5 antibody

<400> SEQUENCE: 117

Gln Ser Val Leu Thr Gln Pro Pro Ser Ala Ser Gly Thr Pro Gly Gln
1               5                   10                  15

Arg Val Thr Ile Ser Cys Gln Gly Glu Ser Leu Arg Ser Tyr Tyr Val
            20                  25                  30

Asn Trp Tyr Gln Gln Leu Pro Gly Thr Ala Pro Lys Leu Leu Ile Tyr
        35                  40                  45
```

-continued

```
Asp His Ser Lys Arg Pro Thr Gly Val Pro Asp Arg Phe Ser Gly Ser
    50              55              60

Lys Ser Gly Thr Ser Ala Ser Leu Ala Ile Ser Gly Leu Arg Ser Glu
65              70              75              80

Asp Glu Ala Asp Tyr Tyr Cys Gln Ser Tyr Glu Ser Ser Thr Val Val
            85              90              95

Phe Gly Gly Gly Thr Lys Leu Thr Val Leu Gly Gln Pro Lys Ala Ala
            100             105             110

Pro Ser Val Thr Leu Phe Pro Pro Ser Ser Glu Glu Leu Gln Ala Asn
            115             120             125

Lys Ala Thr Leu Val Cys Leu Ile Ser Asp Phe Tyr Pro Gly Ala Val
    130             135             140

Thr Val Ala Trp Lys Ala Asp Ser Ser Pro Val Lys Ala Gly Val Glu
145             150             155             160

Thr Thr Thr Pro Ser Lys Gln Ser Asn Asn Lys Tyr Ala Ala Ser Ser
            165             170             175

Tyr Leu Ser Leu Thr Pro Glu Gln Trp Lys Ser His Arg Ser Tyr Ser
            180             185             190

Cys Gln Val Thr His Glu Gly Ser Thr Val Glu Lys Thr Val Ala Pro
            195             200             205

Ala Glu Cys Ser
    210
```

```
<210> SEQ ID NO 118
<211> LENGTH: 212
<212> TYPE: PRT
<213> ORGANISM: Artificial Sequence
<220> FEATURE:
<223> OTHER INFORMATION: BCMA-Light Chain of 5A6 M6 antibody

<400> SEQUENCE: 118
```

```
Gln Ser Val Leu Thr Gln Pro Pro Ser Ala Ser Gly Thr Pro Gly Gln
1               5               10              15

Arg Val Thr Ile Ser Cys Gln Gly Glu Ser Leu Arg Ser Tyr Tyr Val
            20              25              30

Asn Trp Tyr Gln Gln Leu Pro Gly Thr Ala Pro Lys Leu Leu Ile Tyr
            35              40              45

Asp His Ser Lys Arg Pro Thr Gly Val Pro Asp Arg Phe Ser Gly Ser
    50              55              60

Lys Ser Gly Thr Ser Ala Ser Leu Ala Ile Ser Gly Leu Arg Ser Glu
65              70              75              80

Asp Glu Ala Asp Tyr Tyr Cys Gln Ser Tyr Asp Ala Ser Thr Val Val
            85              90              95

Phe Gly Gly Gly Thr Lys Leu Thr Val Leu Gly Gln Pro Lys Ala Ala
            100             105             110

Pro Ser Val Thr Leu Phe Pro Pro Ser Ser Glu Glu Leu Gln Ala Asn
            115             120             125

Lys Ala Thr Leu Val Cys Leu Ile Ser Asp Phe Tyr Pro Gly Ala Val
    130             135             140

Thr Val Ala Trp Lys Ala Asp Ser Ser Pro Val Lys Ala Gly Val Glu
145             150             155             160

Thr Thr Thr Pro Ser Lys Gln Ser Asn Asn Lys Tyr Ala Ala Ser Ser
            165             170             175

Tyr Leu Ser Leu Thr Pro Glu Gln Trp Lys Ser His Arg Ser Tyr Ser
            180             185             190
```

Cys Gln Val Thr His Glu Gly Ser Thr Val Glu Lys Thr Val Ala Pro
        195                 200                 205

Ala Glu Cys Ser
    210

<210> SEQ ID NO 119
<211> LENGTH: 212
<212> TYPE: PRT
<213> ORGANISM: Artificial Sequence
<220> FEATURE:
<223> OTHER INFORMATION: BCMA-Light Chain of 5A6 M7 antibody

<400> SEQUENCE: 119

Gln Ser Val Leu Thr Gln Pro Pro Ser Ala Ser Gly Thr Pro Gly Gln
1               5                   10                  15

Arg Val Thr Ile Ser Cys Gln Gly Asp Ala Leu Arg Ser Tyr Tyr Val
            20                  25                  30

Asn Trp Tyr Gln Gln Leu Pro Gly Thr Ala Pro Lys Leu Leu Ile Tyr
        35                  40                  45

Asp His Ser Lys Arg Pro Thr Gly Val Pro Asp Arg Phe Ser Gly Ser
    50                  55                  60

Lys Ser Gly Thr Ser Ala Ser Leu Ala Ile Ser Gly Leu Arg Ser Glu
65                  70                  75                  80

Asp Glu Ala Asp Tyr Tyr Cys Gln Ser Tyr Glu Ser Ser Thr Val Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Ala Glu Cys Ser
    210

<210> SEQ ID NO 120
<211> LENGTH: 212
<212> TYPE: PRT
<213> ORGANISM: Artificial Sequence
<220> FEATURE:
<223> OTHER INFORMATION: BCMA-Light Chain of 5A6 M8 antibody

<400> SEQUENCE: 120

Gln Ser Val Leu Thr Gln Pro Pro Ser Ala Ser Gly Thr Pro Gly Gln
1               5                   10                  15

Arg Val Thr Ile Ser Cys Gln Gly Asp Ala Leu Arg Ser Tyr Tyr Val
            20                  25                  30

Asn Trp Tyr Gln Gln Leu Pro Gly Thr Ala Pro Lys Leu Leu Ile Tyr
        35                  40                  45

Asp His Ser Lys Arg Pro Thr Gly Val Pro Asp Arg Phe Ser Gly Ser

-continued

```
              50                 55                 60

Lys Ser Gly Thr Ser Ala Ser Leu Ala Ile Ser Gly Leu Arg Ser Glu
65                  70                 75                 80

Asp Glu Ala Asp Tyr Tyr Cys Gln Ser Tyr Asp Ala Ser Thr Val Val
                85                 90                 95

Phe Gly Gly Gly Thr Lys Leu Thr Val Leu Gly Gln Pro Lys Ala Ala
                100                105                110

Pro Ser Val Thr Leu Phe Pro Pro Ser Ser Glu Glu Leu Gln Ala Asn
            115                120                125

Lys Ala Thr Leu Val Cys Leu Ile Ser Asp Phe Tyr Pro Gly Ala Val
        130                135                140

Thr Val Ala Trp Lys Ala Asp Ser Ser Pro Val Lys Ala Gly Val Glu
145                150                155                160

Thr Thr Thr Pro Ser Lys Gln Ser Asn Asn Lys Tyr Ala Ala Ser Ser
                165                170                175

Tyr Leu Ser Leu Thr Pro Glu Gln Trp Lys Ser His Arg Ser Tyr Ser
            180                185                190

Cys Gln Val Thr His Glu Gly Ser Thr Val Glu Lys Thr Val Ala Pro
        195                200                205

Ala Glu Cys Ser
    210

<210> SEQ ID NO 121
<211> LENGTH: 251
<212> TYPE: PRT
<213> ORGANISM: Artificial Sequence
<220> FEATURE:
<223> OTHER INFORMATION: 41B01 scFV

<400> SEQUENCE: 121

Gln Ser Val Leu Thr Gln Pro Pro Ser Ala Ser Gly Thr Pro Gly Arg
1               5                  10                 15

Arg Val Thr Ile Ser Cys Ser Gly Ser Ser Ser Asn Ile Gly Asn Asn
                20                 25                 30

Tyr Val Thr Trp Tyr Gln Gln Leu Pro Gly Thr Ala Pro Lys Leu Leu
            35                 40                 45

Ile Tyr Ala Asp Ser His Arg Pro Ser Gly Val Pro Asp Arg Phe Ser
    50                 55                 60

Gly Ser Lys Ser Gly Thr Ser Ala Ser Leu Ala Ile Ser Gly Leu Arg
65                  70                 75                 80

Ser Glu Asp Glu Ala Asp Tyr Tyr Cys Ala Thr Trp Asp Tyr Ser Leu
                85                 90                 95

Ser Gly Tyr Val Phe Gly Cys Gly Thr Lys Leu Thr Val Leu Gly Gly
            100                105                110

Gly Gly Ser Gly Gly Gly Gly Ser Gly Gly Gly Ser Gly Gly Gly
        115                120                125

Gly Ser Glu Val Gln Leu Leu Glu Ser Gly Gly Gly Leu Val Gln Pro
    130                135                140

Gly Gly Ser Leu Arg Leu Ser Cys Ala Ala Ser Gly Phe Thr Phe Ser
145                150                155                160

Ser Tyr Asp Met Ser Trp Val Arg Gln Ala Pro Gly Lys Cys Leu Glu
                165                170                175

Trp Val Ser Trp Ile Ser Tyr Ser Gly Gly Ser Ile Tyr Tyr Ala Asp
            180                185                190

Ser Val Lys Gly Arg Phe Thr Ile Ser Arg Asp Asn Ser Lys Asn Thr
```

-continued

```
            195                 200                 205

Leu Tyr Leu Gln Met Asn Ser Leu Arg Ala Glu Asp Thr Ala Val Tyr
    210                 215                 220

Tyr Cys Ala Arg Asp Gly Gln Arg Asn Ser Met Arg Glu Phe Asp Tyr
225                 230                 235                 240

Trp Gly Gln Gly Thr Leu Val Thr Val Ser Ser
                245                 250

<210> SEQ ID NO 122
<211> LENGTH: 251
<212> TYPE: PRT
<213> ORGANISM: Artificial Sequence
<220> FEATURE:
<223> OTHER INFORMATION: 41B01 M4 scFV

<400> SEQUENCE: 122

Gln Ser Val Leu Thr Gln Pro Pro Ser Ala Ser Gly Thr Pro Gly Arg
1               5                   10                  15

Arg Val Thr Ile Ser Cys Ser Gly Ser Ser Ser Asn Ile Gly Asn Asn
                20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu Gly Gly
            100                 105                 110

Gly Gly Ser Gly Gly Gly Gly Ser Gly Gly Gly Ser Gly Gly Gly
            115                 120                 125

Gly Ser Glu Val Gln Leu Leu Glu Ser Gly Gly Gly Leu Val Gln Pro
    130                 135                 140

Gly Gly Ser Leu Arg Leu Ser Cys Ala Ala Ser Gly Phe Thr Phe Ser
145                 150                 155                 160

Ser Tyr Asp Met Ser Trp Val Arg Gln Ala Pro Gly Lys Cys Leu Glu
            165                 170                 175

Trp Val Ser Trp Ile Ser Tyr Ser Gly Gly Ser Ile Tyr Tyr Ala Asp
            180                 185                 190

Ser Val Lys Gly Arg Phe Thr Ile Ser Arg Asp Asn Ser Lys Asn Thr
            195                 200                 205

Leu Tyr Leu Gln Met Asn Ser Leu Arg Ala Glu Asp Thr Ala Val Tyr
    210                 215                 220

Tyr Cys Ala Arg Asp Ala Gln Arg Asn Ser Met Arg Glu Phe Asp Tyr
225                 230                 235                 240

Trp Gly Gln Gly Thr Leu Val Thr Val Ser Ser
                245                 250

<210> SEQ ID NO 123
<211> LENGTH: 251
<212> TYPE: PRT
<213> ORGANISM: Artificial Sequence
<220> FEATURE:
<223> OTHER INFORMATION: 41B01 M11 scFV

<400> SEQUENCE: 123
```

-continued

```
Gln Ser Val Leu Thr Gln Pro Pro Ser Ala Ser Gly Thr Pro Gly Arg
1               5                   10                  15

Arg Val Thr Ile Ser Cys Ser Gly Ser Ser Ser Asn Ile Gly Asn Asn
            20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu Gly Gly
            100                 105                 110

Gly Gly Ser Gly Gly Gly Gly Ser Gly Gly Gly Gly Ser Gly Gly Gly
            115                 120                 125

Gly Ser Glu Val Gln Leu Leu Glu Ser Gly Gly Gly Leu Val Gln Pro
        130                 135                 140

Gly Gly Ser Leu Arg Leu Ser Cys Ala Ala Ser Gly Phe Thr Phe Ser
145                 150                 155                 160

Ser Tyr Asp Met Ser Trp Val Arg Gln Ala Pro Gly Lys Cys Leu Glu
            165                 170                 175

Trp Val Ser Trp Ile Ser Tyr Ser Gly Gly Ser Ile Tyr Tyr Ala Asp
            180                 185                 190

Ser Val Lys Gly Arg Phe Thr Ile Ser Arg Asp Asn Ser Lys Asn Thr
            195                 200                 205

Leu Tyr Leu Gln Met Asn Ser Leu Arg Ala Glu Asp Thr Ala Val Tyr
        210                 215                 220

Tyr Cys Ala Arg Asp Ala Gln Arg Gln Ser Met Arg Glu Phe Asp Tyr
225                 230                 235                 240

Trp Gly Gln Gly Thr Leu Val Thr Val Ser Ser
                245                 250
```

```
<210> SEQ ID NO 124
<211> LENGTH: 251
<212> TYPE: PRT
<213> ORGANISM: Artificial Sequence
<220> FEATURE:
<223> OTHER INFORMATION: 41B01 M12 scFV

<400> SEQUENCE: 124
```

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu Gly Gly
            100                 105                 110
```

-continued

```
Gly Gly Ser Gly Gly Gly Gly Ser Gly Gly Gly Gly Ser Gly Gly Gly
        115                 120                 125

Gly Ser Glu Val Gln Leu Leu Glu Ser Gly Gly Gly Leu Val Gln Pro
    130                 135                 140

Gly Gly Ser Leu Arg Leu Ser Cys Ala Ala Ser Gly Phe Thr Phe Ser
145                 150                 155                 160

Ser Tyr Asp Met Ser Trp Val Arg Gln Ala Pro Gly Lys Cys Leu Glu
                165                 170                 175

Trp Val Ser Trp Ile Ser Tyr Ser Gly Gly Ser Ile Tyr Tyr Ala Asp
                180                 185                 190

Ser Val Lys Gly Arg Phe Thr Ile Ser Arg Asp Asn Ser Lys Asn Thr
        195                 200                 205

Leu Tyr Leu Gln Met Asn Ser Leu Arg Ala Glu Asp Thr Ala Val Tyr
    210                 215                 220

Tyr Cys Ala Arg Asp Ala Gln Arg Asn Ser Met Arg Glu Phe Asp Tyr
225                 230                 235                 240

Trp Gly Gln Gly Thr Leu Val Thr Val Ser Ser
                245                 250

<210> SEQ ID NO 125
<211> LENGTH: 251
<212> TYPE: PRT
<213> ORGANISM: Artificial Sequence
<220> FEATURE:
<223> OTHER INFORMATION: 41B01 M13 scFV

<400> SEQUENCE: 125

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
            85                  90                  95

Ser Gly Tyr Val Phe Gly Cys Gly Thr Lys Leu Thr Val Leu Gly Gly
            100                 105                 110

Gly Gly Ser Gly Gly Gly Gly Ser Gly Gly Gly Gly Ser Gly Gly Gly
        115                 120                 125

Gly Ser Glu Val Gln Leu Leu Glu Ser Gly Gly Gly Leu Val Gln Pro
    130                 135                 140

Gly Gly Ser Leu Arg Leu Ser Cys Ala Ala Ser Gly Phe Thr Phe Ser
145                 150                 155                 160

Ser Tyr Asp Met Ser Trp Val Arg Gln Ala Pro Gly Lys Cys Leu Glu
                165                 170                 175

Trp Val Ser Trp Ile Ser Tyr Ser Gly Gly Ser Ile Tyr Tyr Ala Asp
                180                 185                 190

Ser Val Lys Gly Arg Phe Thr Ile Ser Arg Asp Asn Ser Lys Asn Thr
        195                 200                 205

Leu Tyr Leu Gln Met Asn Ser Leu Arg Ala Glu Asp Thr Ala Val Tyr
    210                 215                 220
```

```
Tyr Cys Ala Arg Asp Ala Gln Arg Gln Ser Met Arg Glu Phe Asp Tyr
225                 230                 235                 240

Trp Gly Gln Gly Thr Leu Val Thr Val Ser Ser
                245                 250

<210> SEQ ID NO 126
<211> LENGTH: 257
<212> TYPE: PRT
<213> ORGANISM: Artificial Sequence
<220> FEATURE:
<223> OTHER INFORMATION: 41B02 scFV

<400> SEQUENCE: 126

Gln Ser Val Leu Thr Gln Pro Pro Ser Ala Ser Gly Thr Pro Gly Arg
1               5                   10                  15

Arg Val Thr Ile Ser Cys Ser Gly Ser Ser Ser Asn Ile Gly Asn Asn
                20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu Gly Gly
            100                 105                 110

Gly Gly Ser Gly Gly Gly Gly Ser Gly Gly Gly Gly Ser Gly Gly Gly
        115                 120                 125

Gly Ser Glu Val Gln Leu Leu Glu Ser Gly Gly Gly Leu Val Gln Pro
    130                 135                 140

Gly Gly Ser Leu Arg Leu Ser Cys Ala Ala Ser Gly Phe Thr Phe Ser
145                 150                 155                 160

Gly Tyr Asp Met Ser Trp Val Arg Gln Ala Pro Gly Lys Cys Leu Glu
                165                 170                 175

Trp Val Ser Val Ile Tyr Pro Asp Asp Gly Asn Thr Tyr Tyr Ala Asp
            180                 185                 190

Ser Val Lys Gly Arg Phe Thr Ile Ser Arg Asp Asn Ser Lys Asn Thr
            195                 200                 205

Leu Tyr Leu Gln Met Asn Ser Leu Arg Ala Glu Asp Ala Ala Val Tyr
        210                 215                 220

Tyr Cys Ala Lys His Gly Gly Gln Lys Pro Thr Thr Lys Ser Ser Ser
225                 230                 235                 240

Ala Tyr Gly Met Asp Gly Trp Gly Gln Gly Thr Leu Val Thr Val Ser
                245                 250                 255

Ser

<210> SEQ ID NO 127
<211> LENGTH: 257
<212> TYPE: PRT
<213> ORGANISM: Artificial Sequence
<220> FEATURE:
<223> OTHER INFORMATION: 41B02 M1 scFV

<400> SEQUENCE: 127

Gln Ser Val Leu Thr Gln Pro Pro Ser Ala Ser Gly Thr Pro Gly Gln
1               5                   10                  15
```

-continued

Arg Val Thr Ile Ser Cys Ser Gly Ser Ser Asn Ile Gly Asn Asn
            20              25                  30

Tyr Val Thr Trp Tyr Gln Gln Leu Pro Gly Thr Ala Pro Lys Leu Leu
            35              40                  45

Ile Tyr Ala Asp Ser His Arg Pro Ser Gly Val Pro Asp Arg Phe Ser
        50              55                  60

Gly Ser Lys Ser Gly Thr Ser Ala Ser Leu Ala Ile Ser Gly Leu Arg
65              70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu Gly Gly
            100                 105                 110

Gly Gly Ser Gly Gly Gly Gly Ser Gly Gly Gly Gly Ser Gly Gly Gly
            115                 120                 125

Gly Ser Glu Val Gln Leu Leu Glu Ser Gly Gly Gly Leu Val Gln Pro
        130                 135                 140

Gly Gly Ser Leu Arg Leu Ser Cys Ala Ala Ser Gly Phe Thr Phe Ser
145                 150                 155                 160

Gly Tyr Asp Met Ser Trp Val Arg Gln Ala Pro Gly Lys Cys Leu Glu
                165                 170                 175

Trp Val Ser Val Ile Tyr Pro Asp Asp Gly Asn Thr Tyr Tyr Ala Asp
                180                 185                 190

Ser Val Lys Gly Arg Phe Thr Ile Ser Arg Asp Asn Ser Lys Asn Thr
            195                 200                 205

Leu Tyr Leu Gln Met Asn Ser Leu Arg Ala Glu Asp Thr Ala Val Tyr
        210                 215                 220

Tyr Cys Ala Lys His Gly Gly Gln Lys Pro Thr Thr Lys Ser Ser Ser
225                 230                 235                 240

Ala Tyr Gly Met Asp Gly Trp Gly Gln Gly Thr Leu Val Thr Val Ser
                245                 250                 255

Ser

<210> SEQ ID NO 128
<211> LENGTH: 247
<212> TYPE: PRT
<213> ORGANISM: Artificial Sequence
<220> FEATURE:
<223> OTHER INFORMATION: AB41 scFV

<400> SEQUENCE: 128

Asp Ile Val Met Thr Gln Ser Pro Ala Phe Leu Ser Val Thr Pro Gly
1               5                   10                  15

Glu Lys Val Thr Ile Thr Cys Arg Ala Ser Gln Thr Ile Ser Asp Tyr
            20              25                  30

Leu His Trp Tyr Gln Gln Lys Pro Asp Gln Ala Pro Lys Leu Leu Ile
            35              40                  45

Lys Tyr Ala Ser Gln Ser Ile Ser Gly Ile Pro Ser Arg Phe Ser Gly
        50              55                  60

Ser Gly Ser Gly Thr Asp Phe Thr Phe Thr Ile Ser Ser Leu Glu Ala
65              70                  75                  80

Glu Asp Ala Ala Thr Tyr Tyr Cys Gln Asp Gly His Ser Phe Pro Pro
                85                  90                  95

Thr Phe Gly Cys Gly Thr Lys Leu Glu Ile Lys Arg Gly Gly Gly Gly
            100                 105                 110

Ser Gly Gly Gly Gly Ser Gly Gly Gly Gly Ser Gly Gly Gly Gly Ser

-continued

```
        115                 120                 125
Gln Val Gln Leu Gln Gln Ser Gly Ala Glu Val Ile Lys Pro Gly Ala
    130                 135                 140

Ser Val Lys Leu Ser Cys Lys Ala Ser Gly Tyr Thr Phe Ser Ser Tyr
145                 150                 155                 160

Trp Met His Trp Val Arg Gln Ala Pro Gly Gln Cys Leu Glu Trp Ile
                165                 170                 175

Gly Glu Ile Asn Pro Gly Asn Gly His Thr Asn Tyr Asn Glu Lys Phe
                180                 185                 190

Lys Ser Arg Ala Thr Leu Thr Gly Asp Thr Ser Thr Ser Thr Val Tyr
                195                 200                 205

Met Glu Leu Ser Ser Leu Arg Ser Glu Asp Thr Ala Val Tyr Tyr Cys
    210                 215                 220

Ala Arg Ser Phe Thr Thr Ala Arg Ala Phe Ala Tyr Trp Gly Gln Gly
225                 230                 235                 240

Thr Leu Val Thr Val Ser Ser
                245

<210> SEQ ID NO 129
<211> LENGTH: 715
<212> TYPE: PRT
<213> ORGANISM: Artificial Sequence
<220> FEATURE:
<223> OTHER INFORMATION: Heavy component of 5D5M4(NA)x41B01 M12
      bispecific antibody

<400> SEQUENCE: 129

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Gly Leu Ser Trp Val Arg Gln Ala Pro Gly Lys Gly Leu Glu Trp Val
            35                  40                  45

Ser Leu Ile Asp Ser Ser Gly Ser Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu His Gly Leu Phe Asp Ser Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
    210                 215                 220
```

-continued

```
Cys Pro Pro Cys Pro Ala Pro Glu Leu Leu Gly Gly Pro Ser Val Phe
225             230                 235             240

Leu Phe Pro Pro Lys Pro Lys Asp Thr Leu Met Ile Ser Arg Thr Pro
            245             250                 255

Glu Val Thr Cys Val Val Val Asp Val Ser His Glu Asp Pro Glu Val
            260             265             270

Lys Phe Asn Trp Tyr Val Asp Gly Val Glu Val His Asn Ala Lys Thr
            275             280             285

Lys Pro Arg Glu Glu Gln Tyr Ala Ser Thr Tyr Arg Val Val Ser Val
            290             295             300

Leu Thr Val Leu His Gln Asp Trp Leu Asn Gly Lys Glu Tyr Lys Cys
305             310             315             320

Lys Val Ser Asn Lys Ala Leu Pro Ala Pro Ile Glu Lys Thr Ile Ser
            325             330             335

Lys Ala Lys Gly Gln Pro Arg Glu Pro Gln Val Tyr Thr Leu Pro Pro
            340             345             350

Ser Arg Glu Glu Met Thr Lys Asn Gln Val Ser Leu Thr Cys Leu Val
            355             360             365

Lys Gly Phe Tyr Pro Ser Asp Ile Ala Val Glu Trp Glu Ser Asn Gly
            370             375             380

Gln Pro Glu Asn Asn Tyr Lys Thr Thr Pro Pro Val Leu Asp Ser Asp
385             390             395             400

Gly Ser Phe Phe Leu Tyr Ser Lys Leu Thr Val Asp Lys Ser Arg Trp
            405             410             415

Gln Gln Gly Asn Val Phe Ser Cys Ser Val Met His Glu Ala Leu His
            420             425             430

Asn His Tyr Thr Gln Lys Ser Leu Ser Leu Ser Pro Gly Lys Gly Ser
            435             440             445

Gly Ser Gly Ser Gly Ser Gly Ser Gly Ser Gly Ser Gly Ser Gly Ser
            450             455             460

Gln Ser Val Leu Thr Gln Pro Pro Ser Ala Ser Gly Thr Pro Gly Gln
465             470             475             480

Arg Val Thr Ile Ser Cys Ser Gly Ser Ser Ser Asn Ile Gly Asn Asn
            485             490             495

Tyr Val Thr Trp Tyr Gln Gln Leu Pro Gly Thr Ala Pro Lys Leu Leu
            500             505             510

Ile Tyr Ala Asp Ser His Arg Pro Ser Gly Val Pro Asp Arg Phe Ser
            515             520             525

Gly Ser Lys Ser Gly Thr Ser Ala Ser Leu Ala Ile Ser Gly Leu Arg
            530             535             540

Ser Glu Asp Glu Ala Asp Tyr Tyr Cys Ala Thr Trp Asp Tyr Ser Leu
545             550             555             560

Ser Gly Tyr Val Phe Gly Cys Gly Thr Lys Leu Thr Val Leu Gly Gly
            565             570             575

Gly Gly Ser Gly Gly Gly Gly Ser Gly Gly Gly Gly Ser Gly Gly Gly
            580             585             590

Gly Ser Glu Val Gln Leu Leu Glu Ser Gly Gly Gly Leu Val Gln Pro
            595             600             605

Gly Gly Ser Leu Arg Leu Ser Cys Ala Ala Ser Gly Phe Thr Phe Ser
            610             615             620

Ser Tyr Asp Met Ser Trp Val Arg Gln Ala Pro Gly Lys Cys Leu Glu
625             630             635             640

Trp Val Ser Trp Ile Ser Tyr Ser Gly Gly Ser Ile Tyr Tyr Ala Asp
```

-continued

```
                        645                 650                 655

Ser Val Lys Gly Arg Phe Thr Ile Ser Arg Asp Asn Ser Lys Asn Thr
                660                 665                 670

Leu Tyr Leu Gln Met Asn Ser Leu Arg Ala Glu Asp Thr Ala Val Tyr
            675                 680                 685

Tyr Cys Ala Arg Asp Ala Gln Arg Asn Ser Met Arg Glu Phe Asp Tyr
        690                 695                 700

Trp Gly Gln Gly Thr Leu Val Thr Val Ser Ser
705                 710                 715

<210> SEQ ID NO 130
<211> LENGTH: 716
<212> TYPE: PRT
<213> ORGANISM: Artificial Sequence
<220> FEATURE:
<223> OTHER INFORMATION: Heavy component of 5A6M6(NA)x41B01 M12
      bispecific antibody

<400> SEQUENCE: 130

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Val His Trp Val Arg Gln Ala Pro Gly Lys Gly Leu Glu Trp Val
        35                  40                  45

Ser Tyr Ile Ser Tyr Ser Gly Gly Thr Tyr Tyr Asn Pro Ser Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Ser Asp Asp Phe Gly Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285
```

```
Thr Lys Pro Arg Glu Glu Gln Tyr Ala Ser Thr Tyr Arg Val Val Ser
    290             295             300

Val Leu Thr Val Leu His Gln Asp Trp Leu Asn Gly Lys Glu Tyr Lys
305             310             315             320

Cys Lys Val Ser Asn Lys Ala Leu Pro Ala Pro Ile Glu Lys Thr Ile
            325             330             335

Ser Lys Ala Lys Gly Gln Pro Arg Glu Pro Gln Val Tyr Thr Leu Pro
            340             345             350

Pro Ser Arg Glu Glu Met Thr Lys Asn Gln Val Ser Leu Thr Cys Leu
            355             360             365

Val Lys Gly Phe Tyr Pro Ser Asp Ile Ala Val Glu Trp Glu Ser Asn
    370             375             380

Gly Gln Pro Glu Asn Asn Tyr Lys Thr Thr Pro Pro Val Leu Asp Ser
385             390             395             400

Asp Gly Ser Phe Phe Leu Tyr Ser Lys Leu Thr Val Asp Lys Ser Arg
            405             410             415

Trp Gln Gln Gly Asn Val Phe Ser Cys Ser Val Met His Glu Ala Leu
            420             425             430

His Asn His Tyr Thr Gln Lys Ser Leu Ser Leu Ser Pro Gly Lys Gly
    435             440             445

Ser Gly Ser Gly Ser Gly Ser Gly Ser Gly Ser Gly Ser Gly Ser Gly
    450             455             460

Ser Gln Ser Val Leu Thr Gln Pro Pro Ser Ala Ser Gly Thr Pro Gly
465             470             475             480

Gln Arg Val Thr Ile Ser Cys Ser Gly Ser Ser Asn Ile Gly Asn
            485             490             495

Asn Tyr Val Thr Trp Tyr Gln Gln Leu Pro Gly Thr Ala Pro Lys Leu
            500             505             510

Leu Ile Tyr Ala Asp Ser His Arg Pro Ser Gly Val Pro Asp Arg Phe
    515             520             525

Ser Gly Ser Lys Ser Gly Thr Ser Ala Ser Leu Ala Ile Ser Gly Leu
    530             535             540

Arg Ser Glu Asp Glu Ala Asp Tyr Tyr Cys Ala Thr Trp Asp Tyr Ser
545             550             555             560

Leu Ser Gly Tyr Val Phe Gly Cys Gly Thr Lys Leu Thr Val Leu Gly
            565             570             575

Gly Gly Gly Ser Gly Gly Gly Gly Ser Gly Gly Gly Gly Ser Gly Gly
            580             585             590

Gly Gly Ser Glu Val Gln Leu Leu Glu Ser Gly Gly Gly Leu Val Gln
            595             600             605

Pro Gly Gly Ser Leu Arg Leu Ser Cys Ala Ala Ser Gly Phe Thr Phe
    610             615             620

Ser Ser Tyr Asp Met Ser Trp Val Arg Gln Ala Pro Gly Lys Cys Leu
625             630             635             640

Glu Trp Val Ser Trp Ile Ser Tyr Ser Gly Gly Ser Ile Tyr Tyr Ala
            645             650             655

Asp Ser Val Lys Gly Arg Phe Thr Ile Ser Arg Asp Asn Ser Lys Asn
            660             665             670
```

-continued

```
Thr Leu Tyr Leu Gln Met Asn Ser Leu Arg Ala Glu Asp Thr Ala Val
        675             680             685

Tyr Tyr Cys Ala Arg Asp Ala Gln Arg Asn Ser Met Arg Glu Phe Asp
    690             695             700

Tyr Trp Gly Gln Gly Thr Leu Val Thr Val Ser Ser
705             710             715
```

ANTI-BCMA/ANTI-4-1BB BISPECIFIC ANTIBODIES AND USES THEREOF

CROSS-REFERENCE TO RELATED APPLICATIONS

This application is a national phase application of PCT Application No. PCT/KR20 20/018029, filed on Dec. 10, 2020, which claims priority to U.S. Provisional Application No. 62/945,965 filed on Dec. 10, 2019 and PCT Application No. PCT/KR2019/018 357 filed on Dec. 24, 2019. The entire disclosure of the applications identified in this paragraph is incorporated herein by reference.

TECHNICAL FIELD

The present disclosure relates to anti-BCMA/anti-4-1BB bispecific antibodies capable of effectively blocking the interactions between BCMA and its ligand, and activating 4-1BB signaling; a method of preparing the same; and use thereof. The bispecific antibodies may have high binding affinity to both of a BCMA protein and a 4-1BB protein.

BACKGROUND ART

B-cell maturation antigen (BCMA) is a protein of about 20 KDa and belongs to the tumor necrosis factor-receptor (TNFR) superfamily. BCMA is also known to have a ligand of B-cell Activating Factor belonging to the Tumor Necrosis Factor family (BAFF) and A Proliferation Inducing Ligand (APRIL). In pathological situations, BCMA is expressed in neoplastic plasma cells of patients with multiple myeloma (MM), and survival rates of patients with multiple myeloma are lower with higher BCMA expression (Moreaux et al., Eur J Haematol 2009 83: 119-129). Multiple myeloma is a neoplastic disease caused by monoclonal proliferation of plasma cells. The initial treatment rate has increased due to the development of drugs such as thalidomide, bortezomib, and lenalidomide, and the development of treatment methods. However, the survival of patients with multiple myeloma has not improved significantly.

4-1BB is a member of the TNF-receptor superfamily (TNFRSF) and is a co-stimulatory molecule which is expressed following the activation of immune cells, including both innate and adaptive immune cells. 4-1BB plays an important role in modulating the activity of various immune cells. Agonistic 4-1BB antibodies enhance immune cell proliferation, survival, secretion of cytokines and cytolytic activity of CD8 T cells. Many other studies have shown that activation of 4-1BB enhances the immune response to eliminate tumors in mice. Therefore, it suggests that 4-1BB is a promising target molecule in cancer immunology. Despite their anti-tumor efficacy, anti-4-1BB antibodies have induced severe liver toxicity in clinical application.

Multispecific antibodies targeting two or more antigens have been developed in various kinds and forms and are expected as new drug antibodies having excellent therapeutic effects as compared to monoclonal antibodies. Accordingly, there is a need for the development of multispecific antibodies which are effective in the treatment of cancer such as multiple myeloma.

SUMMARY

Technical Problem

Provided is an anti-B-cell maturation antigen (BCMA)/anti-4-1BB bispecific antibody or an antigen-binding fragment thereof.

Provided is a pharmaceutical composition for prevention or treatment of a disease related to BCMA, 4-1BB, or both thereof.

Provided is a method of prevention or treatment of a disease related to BCMA, 4-1BB, or both thereof in an individual.

Provided is an anti-B-cell maturation antigen (BCMA)/anti-4-1BB bispecific antibody or an antigen-binding fragment thereof for use in the prevention or treatment of a disease related to BCMA, 4-1BB, or both thereof.

Technical Solution

Reference will now be made in detail to example embodiments, which are illustrated in the accompanying drawings, wherein like reference numerals refer to like elements throughout. In this regard, the present example embodiments may have different forms and should not be construed as being limited to the descriptions set forth herein. Accordingly, the example embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an aspect of the present disclosure, anti-B-cell maturation antigen (BCMA)/anti-4-1BB bispecific antibody or an antigen-binding fragment thereof includes an anti-BCMA antibody or an antigen-binding fragment thereof, and an anti-4-1BB antibody or an antigen-binding fragment thereof.

The term "antibody" is interchangeably used with "immunoglobulin (Ig)." The whole antibody has a structure including two full-length light chains and two full-length heavy chains, which are connected by disulfide (SS) bonds. The antibody may be, for example, IgA, IgD, IgE, IgG, or IgM. The antibody may be a monoclonal antibody or a polyclonal antibody. The antibody may be an animal-derived antibody, a mouse-human chimeric antibody, a humanized antibody, or a human antibody.

The term "antigen-binding fragment" refers to a fragment of the whole immunoglobulin structure, which may be a part of a polypeptide including an antigen-binding site. For example, the antigen-binding fragment may be scFv, $(scFv)_2$, Fv, Fab, Fab', Fv $F(ab')_2$, or a combination thereof.

There are five types of heavy chains denoted by $\gamma$, $\delta$, $\alpha$, $\mu$, and $\varepsilon$. The type of heavy chain defines the class of antibody. The heavy chain types $\alpha$ and $\gamma$ each chain consists of approximately 450 amino acids, whereas $\mu$ and $\varepsilon$ each chain consists of approximately 550 amino acids. Each heavy chain has two regions, i.e., the variable region and the constant region.

There are two types of light chains denoted by $\lambda$ and $\kappa$. Each light chain consists of approximately 211 to 217 amino acids. Each human antibody contains only one type of light chain. Each light chain contains two successive domains including one constant region and one variable region.

The variable region refers to a region of the antibody which binds to an antigen.

The antibody or the antigen-binding fragment thereof may be modified. For example, the antibody or the antigen-binding fragment thereof may be modified by conjugation or binding, glycosylation, tag attachment, or a combination thereof. The antibody may be conjugated with other drugs such as anti-cancer drug. For example, the antibody or the antigen-binding fragment thereof may be conjugated with horseradish peroxidase (HRP), alkaline phosphatase, hapten, biotin, streptavidin, a fluorescent material, a radioactive material, quantum dots, polyethylene glycol (PEG), a histidine tag, or a combination thereof. The fluorescent material may be ALEXA FLUOR® 532, ALEXA FLUOR® 546, ALEXA FLUOR® 568, ALEXA FLUOR® 680, ALEXA FLUOR® 750, ALEXA FLUOR® 790, or ALEXA FLUOR® M350.

Anti-BCMA Antibody or the Antigen-Binding Fragment Thereof

The anti-BCMA antibody or the antigen-binding fragment thereof may include a heavy chain variable region including at least one amino acid sequence selected from the group consisting of SEQ ID NOs: 10 to 21, a light chain variable region including at least one amino acid sequence selected from the group consisting of SEQ ID NOs: 22 to 32 and 54 to 64, or the heavy chain variable region and the light chain variable region.

The anti-4-1BB antibody or the antigen-binding fragment thereof may include a heavy chain variable region including at least one amino acid sequence selected from the group consisting of SEQ ID NOs: 81 to 91, a light chain variable region including at least one amino acid sequence selected from the group consisting of SEQ ID NOs: 92 to 97, or the heavy chain variable region and the light chain variable region.

The heavy chain variable region of the anti-BCMA antibody or the antigen-binding fragment thereof may include a complementarity-determining region-H1 (CDR-H1) including an amino acid sequence selected from the group consisting of SEQ ID. NOs: 10 to 13; a CDR-H2 including an amino acid sequence selected from SEQ ID NOs: 14 to 17; and a CDR-H3 including an amino acid sequence selected from SEQ ID NOs: 18 to 21. The term "complementarity-determining region (CDR)" refers to a site of the variable region of an antibody that imparts binding specificity of the antibody or antigen-binding fragment thereof to an antigen.

The light chain variable region of the anti-BCMA antibody or the antigen-binding fragment thereof may include a complementarity-determining region-L1 (CDR-L1) including an amino acid sequence selected from the group consisting of SEQ ID. NOs: 22 to 25 and 54 to 62; a CDR-L2 including an amino acid sequence selected from SEQ ID NOs: 26 to 28; and a CDR-L3 including an amino acid sequence selected from SEQ ID NOs: 29 to 32, 63, and 64.

The anti-BCMA antibody or the antigen-binding fragment thereof may be selected from the group consisting of:

(1) an antibody or an antigen-binding fragment comprising a CDR-H1 having the amino acid sequence of SEQ ID NO: 10, a CDR-H2 having the amino acid sequence of SEQ ID NO: 14, and a CDR-H3 having the amino acid sequence of SEQ ID NO: 18;

(2) an antibody or an antigen-binding fragment comprising a CDR-H1 having the amino acid sequence of SEQ ID NO: 11, a CDR-H2 having the amino acid sequence of SEQ ID NO: 15, and a CDR-H3 having the amino acid sequence of SEQ ID NO: 19;

(3) an antibody or an antigen-binding fragment comprising a CDR-H1 having the amino acid sequence of SEQ ID NO: 12, a CDR-H2 having the amino acid sequence of SEQ ID NO: 16, and a CDR-H3 having the amino acid sequence of SEQ ID NO: 20; and (4) an antibody or an antigen-binding fragment comprising a CDR-H1 having the amino acid sequence of SEQ ID NO: 13, a CDR-H2 having the amino acid sequence of SEQ ID NO: 17, and a CDR-H3 having the amino acid sequence of SEQ ID NO: 21.

The anti-BCMA antibody or the antigen-binding fragment thereof may be selected from the group consisting of:

(1) an antibody or an antigen-binding fragment comprising a CDR-L1 having the amino acid sequence of SEQ ID NO: 22, a CDR-L2 having the amino acid sequence of SEQ ID NO: 26, and a CDR-L3 having the amino acid sequence of SEQ ID NO: 29;

(2) an antibody or an antigen-binding fragment comprising a CDR-L1 having the amino acid sequence of SEQ ID NO: 23, a CDR-L2 having the amino acid sequence of SEQ ID NO: 27, and a CDR-L3 having the amino acid sequence of SEQ ID NO: 30;

(3) an antibody or an antigen-binding fragment comprising a CDR-L1 having the amino acid sequence of SEQ ID NO: 24, a CDR-L2 having the amino acid sequence of SEQ ID NO: 27, and a CDR-L3 having the amino acid sequence of SEQ ID NO: 31;

(4) an antibody or an antigen-binding fragment comprising a CDR-L1 having the amino acid sequence of SEQ ID NO: 25, a CDR-L2 having the amino acid sequence of SEQ ID NO: 28, and a CDR-L3 having the amino acid sequence of SEQ ID NO: 32;

(5) an antibody or an antigen-binding fragment comprising a CDR-L1 having the amino acid sequence of SEQ ID NO: 54, a CDR-L2 having the amino acid sequence of SEQ ID NO: 27, and a CDR-L3 having the amino acid sequence of SEQ ID NO: 31;

(6) an antibody or an antigen-binding fragment comprising a CDR-L1 having the amino acid sequence of SEQ ID NO: 55, a CDR-L2 having the amino acid sequence of SEQ ID NO: 27, and a CDR-L3 having the amino acid sequence of SEQ ID NO: 31;

(7) an antibody or an antigen-binding fragment comprising a CDR-L1 having the amino acid sequence of SEQ ID NO: 56, a CDR-L2 having the amino acid sequence of SEQ ID NO: 27, and a CDR-L3 having the amino acid sequence of SEQ ID NO: 31;

(8) an antibody or an antigen-binding fragment comprising a CDR-L1 having the amino acid sequence of SEQ ID NO: 57, a CDR-L2 having the amino acid sequence of SEQ ID NO: 27, and a CDR-L3 having the amino acid sequence of SEQ ID NO: 31;

(9) an antibody or an antigen-binding fragment comprising a CDR-L1 having the amino acid sequence of SEQ ID NO: 58, a CDR-L2 having the amino acid sequence of SEQ ID NO: 27, and a CDR-L3 having the amino acid sequence of SEQ ID NO: 31;

(10) an antibody or an antigen-binding fragment comprising a CDR-L1 having the amino acid sequence of SEQ ID NO: 59, a CDR-L2 having the amino acid sequence of SEQ ID NO: 28, and a CDR-L3 having the amino acid sequence of SEQ ID NO: 32;

(11) an antibody or an antigen-binding fragment comprising a CDR-L1 having the amino acid sequence of SEQ ID NO: 60, a CDR-L2 having the amino acid sequence of SEQ ID NO: 28, and a CDR-L3 having the amino acid sequence of SEQ ID NO: 32;

(12) an antibody or an antigen-binding fragment comprising a CDR-L1 having the amino acid sequence of SEQ ID NO: 25, a CDR-L2 having the amino acid sequence of SEQ ID NO: 28, and a CDR-L3 having the amino acid sequence of SEQ ID NO: 63;

(13) an antibody or an antigen-binding fragment comprising a CDR-L1 having the amino acid sequence of SEQ ID NO: 25, a CDR-L2 having the amino acid sequence of SEQ ID NO: 28, and a CDR-L3 having the amino acid sequence of SEQ ID NO: 64;

(14) an antibody or an antigen-binding fragment comprising a CDR-L1 having the amino acid sequence of SEQ ID NO: 61, a CDR-L2 having the amino acid sequence of SEQ ID NO: 28, and a CDR-L3 having the amino acid sequence of SEQ ID NO: 63;

(15) an antibody or an antigen-binding fragment comprising a CDR-L1 having the amino acid sequence of SEQ ID NO: 61, a CDR-L2 having the amino acid sequence of SEQ ID NO: 28, and a CDR-L3 having the amino acid sequence of SEQ ID NO: 64;

(16) an antibody or an antigen-binding fragment comprising a CDR-L1 having the amino acid sequence of SEQ ID NO: 62, a CDR-L2 having the amino acid sequence of SEQ ID NO: 28, and a CDR-L3 having the amino acid sequence of SEQ ID NO: 63; and

(17) an antibody or an antigen-binding fragment comprising a CDR-L1 having the amino acid sequence of SEQ ID NO: 62, a CDR-L2 having the amino acid sequence of SEQ ID NO: 28, and a CDR-L3 having the amino acid sequence of SEQ ID NO: 64.

The anti-BCMA antibody or the antigen-binding fragment thereof may include a heavy chain variable region comprising an amino acid sequences selected from the group consisting SEQ ID NOs: 2 to 5.

The anti-BCMA antibody or the antigen-binding fragment thereof may include a light chain variable region comprising an amino acid sequences selected from the group consisting SEQ ID NOs: 6 to 9 and 41 to 53.

The B Cell Maturation Antigen (BCMA) may be a BCMA polypeptide or a fragment thereof. BCMA may also be referred to as tumor necrosis factor receptor superfamily member 17 (TNFRSF17), BCM, CD269, TNFRSF13A, or TNF receptor superfamily member 17. The BCMA polypeptide may include amino acid sequence of GenBank Accession No. NP_001183 (human) or amino acid sequence of GenBank Accession No. NP_035738 (mouse). The BCMA polypeptide may include amino acid sequence encoded by polynucleotide of GenBank Accession No. NM_001192 (human) or GenBank Accession No. NM_011608 (mouse). The fragment may be a polypeptide comprising any part of amino acid sequence of a BCMA polypeptide.

The anti-BCMA antibody or the antigen-binding fragment thereof may have affinity to an BCMA polypeptide or a fragment thereof, thereby specifically binding to BCMA.

The anti-BCMA antibody or antigen-binding fragment thereof may inhibit the binding between a BCMA protein and a substance specifically binding to the BCMA protein. Substances that specifically bind to the BCMA protein may also be referred to as ligands, for example B-cell Activating Factor belonging to the Tumor Necrosis Factor family (BAFF), A Proliferation Inducing Ligand (APRIL), or a combination thereof.

Anti-4-1BB Antibody or the Antigen-Binding Fragment Thereof

The heavy chain variable region of the anti-4-1BB antibody or the antigen-binding fragment thereof may include a CDR-H1 including an amino acid sequence selected from the group consisting of SEQ ID. NOs: 81 to 83; a CDR-H2 including an amino acid sequence selected from SEQ ID NOs: 84 to 86; and a CDR-H3 including an amino acid sequence selected from SEQ ID NOs: 87 to 91.

The light chain variable region of the anti-4-1BB antibody or the antigen-binding fragment thereof may include a CDR-L1 including an amino acid sequence selected from the group consisting of SEQ ID. NOs: 92 and 93; a CDR-L2 including an amino acid sequence selected from SEQ ID NOs: 94 and 95; and a CDR-L3 including an amino acid sequence selected from SEQ ID NOs: 96 and 97.

The anti-4-1BB antibody or the antigen-binding fragment thereof may be selected from the group consisting of:

(1) an antibody or an antigen-binding fragment comprising a CDR-H1 having the amino acid sequence of SEQ ID NO: 81, a CDR-H2 having the amino acid sequence of SEQ ID NO: 84, and a CDR-H3 having the amino acid sequence of SEQ ID NO: 87;

(2) an antibody or an antigen-binding fragment comprising a CDR-H1 having the amino acid sequence of SEQ ID NO: 81, a CDR-H2 having the amino acid sequence of SEQ ID NO: 84, and a CDR-H3 having the amino acid sequence of SEQ ID NO: 88;

(3) an antibody or an antigen-binding fragment comprising a CDR-H1 having the amino acid sequence of SEQ ID NO: 81, a CDR-H2 having the amino acid sequence of SEQ ID NO: 84, and a CDR-H3 having the amino acid sequence of SEQ ID NO: 89;

(4) an antibody or an antigen-binding fragment comprising a CDR-H1 having the amino acid sequence of SEQ ID NO: 82, a CDR-H2 having the amino acid sequence of SEQ ID NO: 85, and a CDR-H3 having the amino acid sequence of SEQ ID NO: 90; and (5) an antibody or an antigen-binding fragment comprising a CDR-H1 having the amino acid sequence of SEQ ID NO: 83, a CDR-H2 having the amino acid sequence of SEQ ID NO: 86, and a CDR-H3 having the amino acid sequence of SEQ ID NO: 91.

The anti-4-1BB antibody or the antigen-binding fragment thereof may be selected from the group consisting of:

(1) an antibody or an antigen-binding fragment comprising a CDR-L1 having the amino acid sequence of SEQ ID NO: 92, a CDR-L2 having the amino acid sequence of SEQ ID NO: 94, and a CDR-L3 having the amino acid sequence of SEQ ID NO: 96; and (2) an antibody or an antigen-binding fragment comprising a CDR-L1 having the amino acid sequence of SEQ ID NO: 93, a CDR-L2 having the amino acid sequence of SEQ ID NO: 95, and a CDR-L3 having the amino acid sequence of SEQ ID NO: 97.

The anti-4-1BB antibody or the antigen-binding fragment thereof may be selected from the group consisting of:

(1) an antibody or an antigen-binding fragment comprising a CDR-L1 having the amino acid sequence of SEQ ID NO: 92, a CDR-L2 having the amino acid sequence of SEQ ID NO: 94, and a CDR-L3 having the amino acid sequence of SEQ ID NO: 96; and (2) an antibody or an antigen-binding fragment comprising a CDR-L1 having the amino acid sequence of SEQ ID NO: 93, a CDR-L2 having the amino acid sequence of SEQ ID NO: 95, and a CDR-L3 having the amino acid sequence of SEQ ID NO: 97.

The anti-4-1BB antibody or the antigen-binding fragment thereof may include a light chain variable region comprising an amino acid sequences selected from the group consisting SEQ ID NOs: 73 to 80.

The 4-1BB may be a 4-1BB polypeptide or a fragment thereof. 4-1BB may also be referred to as CD137, CDw137, ILA, tumor necrosis factor receptor superfamily member 9 (TNFRSF9), or TNF receptor superfamily member 9. The 4-1BB polypeptide may include amino acid sequence of GenBank Accession No. NP_001552 (human), or amino acid sequence of GenBank Accession No. NP_001070976, NP_001070977, or NP_035742 (mouse). The BCMA polypeptide may include amino acid sequence encoded by polynucleotide of GenBank Accession No. NM_001561 (human), or GenBank Accession No. NM_001077508, NM_001077509, or NM_011612 (mouse). The fragment may be a polypeptide comprising any part of amino acid sequence of a 4-1BB polypeptide.

The anti-4-1BB antibody or the antigen-binding fragment thereof may have affinity to an 4-1BB polypeptide or a fragment thereof, thereby specifically binding to 4-1BB. The anti-4-1 BB antibody or an antigen-binding fragment thereof is capable of enhancing immune response and/or treating tumor (cancer) in a mammal. The anti-4-1BB antibody or an antigen-binding fragment thereof is characterized by localizing and/or activating only in tumor microenvironment (TME) and/or considerably reducing liver toxicities compared to pre-existing anti-4-11BB antibodies, with maintaining the efficacies of enhancing immune response enhancement and/or tumor treatment.

Anti-BCMA/Anti-4-1BB Bispecific Antibody or the Antigen-Binding Fragment

In the anti-BCMA/anti-4-1BB bispecific antibody or an antigen-binding fragment thereof, each of the anti-BCMA antibody or antigen-binding fragment thereof and the anti-4-1BB antibody or antigen-binding fragment thereof is independently a chimeric antibody, a humanized antibody, or a human antibody.

In the bispecific antibody, one of the BCMA targeting moiety and the 4-1BB targeting moiety can be a full-length antibody, and the other can be an antigen-binding fragment (e.g., scFv) comprising heavy chain CDRs, light chain CDRs, or a combination thereof. The full-length antibody targeting one of BCMA and 4-1BB proteins, and the antigen-binding fragment targeting the other protein may be chemically linked (e.g., covalently linked) directly or via a peptide linker. The antigen-binding fragment (e.g., scFv) may be linked directly or via a peptide linker to N-terminus of the full-length antibody (e.g., N-terminus of a light chain or a heavy chain of the full-length antibody), C-terminus of the full-length antibody (e.g., C-terminus of a heavy chain (or Fc or CH3 domain) of the full-length antibody), or both thereof (see FIG. 1).

The anti-BCMA/anti-4-1BB bispecific antibody or the antigen-binding fragment may include further at least one of a peptide linker. The term "peptide linker" may be those including any amino acids of 1 to 100, particularly 2 to 50, and any kinds of amino acids may be included without any restrictions. The peptide linker may include a peptide having an amino acid sequence selected from the group consisting of SEQ ID NO: 98 and SEQ ID NO: 99.

In an embodiment, the bispecific antibody may comprise a full-length anti-BCMA antibody, an antigen-binding fragment (e.g., scFv) of an anti-4-1BB antibody, and a peptide linker therebetween. In other embodiment, the bispecific antibody may comprise a full-length anti-4-1BB antibody, an antigen-binding fragment (e.g., scFv) of an anti-BCMA antibody, and a peptide linker therebetween.

In the anti-BCMA/anti-4-1BB bispecific antibody or an antigen-binding fragment thereof, the antibody may be IgA, IgD, IgE, IgG, or IgM. The antibody may be a monoclonal antibody or a polyclonal antibody. The antigen-binding fragment may be scFv, (scFv)$_2$, Fv, Fab, Fab', F(ab')$_2$, or a combination thereof. The antibody or the antigen-binding fragment thereof is modified by conjugation or binding, glycosylation, tag attachment, or a combination thereof.

In an embodiment, the scFv contained in the bispecific antibody may comprise a heavy chain variable region and a light chain variable region in any order. For example, the scFv contained in the bispecific antibody may comprise a heavy chain variable region and a light chain variable region, in a direction from N-terminus to C-terminus, and optionally a peptide linker therebetween, or alternatively, the scFv contained in the bispecific antibody may comprise a light chain variable region and a heavy chain variable region, in a direction from N-terminus to C-terminus, and optionally a peptide linker therebetween.

The anti-BCMA/anti-4-1BB bispecific antibody or the antigen-binding fragment may be in the form of IgG-scFv, triomab, knobs into holes (kih) IgG with common light chain, crossmab, ortho-Fab IgG, dual variable domain immunoglobulin (DVD-Ig™), 2 in 1-IgG, scFv2-Fc, bi-NANOBODY®, bispecific T cell engager (BiTE®), tand-Abs, dual affinity retargeting (DART®) antibody, DART®-Fc, scFv-human serum albumin (HSA)-scFv, dock-and-lock (DNL)-Fab3, minibody, scFv-Fc, scFv-zipper, scFv, Fab, Fab2 (bispecific), Fab3 (trispecific), scFab, Bis-scFv (bispecific), sdAb (VH/VHH), tetrabody, triabody, a diabody, camel Ig, IgNAR, IgG, bispecific construct comprising a Knob in Hole, a bispecific construct comprising a DUO-BODY®, a tetravalent multispecific antibody, tetravalent construct, tetravalent dual variable domain (DVD) construct, tetravalent IgGScv construct, tetravalent Mbatryn construct, or a composite antibody, or a combination thereof.

The anti-BCMA/anti-4-1BB bispecific antibody or the antigen-binding fragment may activate 4-1BB signaling depending on BCMA expressed on cell surfaces.

According to another aspect of the present disclosure, a pharmaceutical composition for prevention or treatment of a disease related to BCMA, 4-1BB, or both thereof includes the anti-BCMA/anti-4-1BB bispecific antibody or the antigen-binding fragment according to any one of the above-described embodiments, and a pharmaceutically acceptable carrier.

The BCMA, 4-1BB, anti-BCMA/anti-4-1BB bispecific antibody, and antigen-binding fragment are the same as described above.

The disease related to BCMA, 4-1BB, or both thereof may be cancer. The cancer may be a solid cancer or a non-solid cancer. Solid cancers refer to the incidence of cancerous tumors in solid organs such as the liver, lung, breast, or skin, whereas non-solid cancers refer to cancers affecting the blood, and so are called blood cancer. For example, the cancer may be selected from the group consisting of breast cancer, skin cancer, head and neck cancer, pancreatic cancer, lung cancer, colon cancer, colorectal cancer, gastric cancer, ovarian cancer, prostate cancer, bladder cancer, uterine cancer, liver cancer, kidney cancer, clear cell sarcoma, melanoma, cerebrospinal tumors, brain cancer, thymoma, mesothelioma, esophageal cancer, biliary tract cancer, testicular cancer, germinal cancer, thyroid cancer, parathyroid cancer, cervical cancer, endometrial cancer, lymphoma, myelodysplastic syndromes (MDS), myelofibrosis, acute leukemia, chronic leukemia, multiple myeloma, Hodgkin's disease, endocrine cancer, and sarcoma.

The term "prevention" refers to any act that suppresses or delays the onset of a disease related to BCMA, 4-1BB, or both thereof by administration of the pharmaceutical composition. The term "treatment" refers to any act that alleviates symptoms of a disease related to BCMA, 4-1BB, or both thereof by administration of the pharmaceutical composition.

The pharmaceutical composition may include a pharmaceutically acceptable carrier. The carrier may be construed as meaning an excipient, a diluent, or an adjuvant. For example, the carrier may be selected from the group consisting of lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinylpyrrolidone, water, physiological saline, a buffer such as phosphate-buffered saline (PBS), methyl hydroxybenzoate, propyl hydroxybenzoate, talc, magnesium stearate, glycine, histidine, serine, polysorbate, and mineral oil. The pharmaceutical composition may include a filler, an anti-coagulant, a lubricant, a wetting agent, a flavoring agent, an emulsifier, a preservative, or a combination thereof.

The pharmaceutical composition may be formulated in any form using any common method in the art. For example, the pharmaceutical composition may be formulated in oral dosage form (for example, powders, tablets, capsules, syrups, pills, or granules), or parenteral dosage form (for example, injection). The pharmaceutical composition may be prepared in formulation for systemic delivery, or in a formulation for local delivery.

The pharmaceutical composition may further include an anti-cancer drug. The anti-cancer drug may be Cetuximab, Panitumumab, Erlotinib, Gefitinib, Trastuzumab, T-DM1, Pertuzumab, Lapatinib, Paclitaxel, Tamoxifen, Cisplatin, anti-CTLA-4 antibody, anti-PD-1 antibody, anti-PD-L1 antibody, 5-fluorouracil (5FU), Gemcitabine, or a combination thereof. The pharmaceutical composition may include a single composition or separate compositions. For example, the anti-BCMA/anti-4-1BB bispecific antibody or the antigen-binding fragment thereof of the pharmaceutical composition may be a composition in parenteral dosage form, and the anti-cancer drug may be a composition in oral dosage form.

The pharmaceutical composition may include an effective amount of the antibody or the antigen-binding fragment thereof, an anti-cancer drug, or a combination thereof. The term "effective amount" used herein refers to an amount sufficient to prevent or treat a disease related to BCMA, 4-1BB, or both thereof when administered to an individual who needs such prevention or treatment. The effective amount may be appropriately selected depending on a selected cell or individual by one of ordinary skill in the art. For example, the effective amount may be determined depending on disease severity, a patient's age, body weight, health conditions, gender, a patient's drug sensitivity, administration duration, administration route, excretion rate, treatment duration, and other factors, including use of a drug in combination with or at the same time as the pharmaceutical composition, and other factors known in the medical field. The effective amount may be about 0.5 µg to about 2 g of the pharmaceutical composition.

A dose of the pharmaceutical composition may be, for example, about 0.001 mg/kg to about 100 mg/kg when administered to an adult. The number of administrations may be, for example, once or multiple times in a day, once in a week to four weeks, or once to twelve times in a year.

According to another aspect of the present disclosure, a method of prevention or treatment of a disease related to BCMA, 4-1BB, or both thereof in an individual includes administering the anti-BCMA/anti-4-1BB bispecific antibody or the antigen-binding fragment according to any one of the above-described embodiments to the individual.

The BCMA, 4-1BB, anti-BCMA/anti-4-1BB bispecific antibody, antigen-binding fragment, prevention, and treatment are the same as described above.

The individual may be a mammal, for example, a human, monkey, cow, horse, pig, dog, sheep, goat, or cat. The individual may be an individual who suffers from a disease related to BCMA, 4-1BB, or both thereof or who is susceptible to the disease, which may be cancer.

The method may further include administering an anti-cancer drug to the individual in need thereof. The anti-cancer drug may be administered at the same time with, separately from, or sequentially with the anti-BCMA/anti-4-1BB bispecific antibody or an antigen-binding fragment thereof according to any of the above-described example embodiments.

For example, the anti-BCMA/anti-4-1BB bispecific antibody or the antigen-binding fragment thereof, an anti-cancer drug, or a combination thereof may be directly administered to the individual by any method, for example, by oral, intravenous, intramuscular, transdermal, mucosal, intranasal, intratracheal, or subcutaneous administration. The antibody or the antigen-binding fragment thereof, an anti-cancer drug, or a combination thereof may be administered systemically or locally. The antibody or the antigen-binding fragment thereof, an anti-cancer drug, or a combination thereof may be administered alone or together with a pharmaceutically active compound.

A dose of the anti-BCMA/anti-4-1BB bispecific antibody or the antigen-binding fragment thereof, an anti-cancer drug, or a combination thereof may vary depending on a patient's condition, body weight, disease severity, drug formulation, administration route, and administration duration, and may be appropriately selected by one of ordinary skill in the art. For example, a dose of the antibody or the antigen-binding fragment thereof, an anti-cancer drug, or a combination thereof may be about 0.001 mg/kg to about 100 mg/kg when administered to an adult. The number of administrations may be, for example, once or multiple times in a day, once in a week to four weeks, or once to twelve times in a year.

According to another aspect of the present disclosure, an anti-B-cell maturation antigen (BCMA)/anti-4-1BB bispecific antibody or an antigen-binding fragment thereof according to any one of the above-described embodiments for use in the prevention or treatment of a disease related to BCMA, 4-1BB, or both thereof is provided.

The BCMA, 4-1BB, anti-BCMA/anti-4-1BB bispecific antibody, antigen-binding fragment, prevention, treatment, and the disease related to BCMA, 4-1BB, or both thereof are the same as described above.

Advantageous Effects of Invention

As described above, according to the one or more example embodiments, the anti-BCMA/anti-4-1BB bispecific antibody or the antigen-binding fragment thereof, and use thereof, are provided. The anti-BCMA/anti-4-1BB bispecific antibody or the antigen-binding fragment thereof may be effectively used to prevent or treat a disease related to BCMA, 4-1BB, or both thereof.

BRIEF DESCRIPTION OF THE DRAWINGS

These and/or other aspects will become apparent and more readily appreciated from the following description of the example embodiments, taken in conjunction with the accompanying drawings in which:

FIG. 5c is a graph showing results of a target protein binding test using DACE (WT and Mutants)

MODE FOR THE INVENTION

Figure 1:
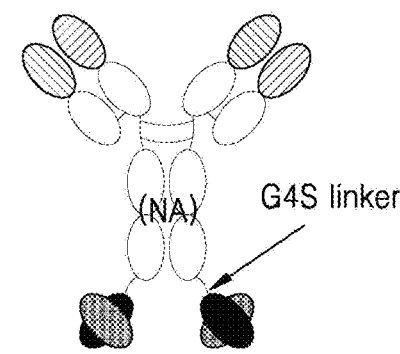
FIG. 1 is a schematic diagram of a bispecific antibody according to an embodiment of the present disclosure, in which the G4S linker has the amino acid sequence of SEQ ID NO: 98.

One or more embodiments of the present disclosure will now be described in detail with reference to the following examples. However, these examples are only for illustrative purposes and are not intended to limit the scope of the one or more embodiments of the present disclosure.

Example 1. Preparation of Anti-BCMA Monoclonal Antibodies 1-1. Preparation of Antigen Antigens were prepared as follows for the preparation of anti-BCMA antibodies. Polypeptides comprising amino acid residues 5-54, 1-51, 1-54, and 4-48, respectively, from the N-terminus of the amino acid sequence of human BCMA (GenBank Accession No. NP_001183.2, SEQ ID NO: 1), were used as antigens.

Specifically, an antigen containing amino acid residues 5-54 of human BCMA (GENSCRIPT®, Z02731) ("human BCMA (5-54)"); an antigen containing amino acid residues 1-51 of human BCMA (made in house, expressed in CHO cells) fused to the Fc region of the human IgG1 ("human BCMA-Fc (1-51)"); an antigen containing amino acid residues 1-54 of human BCMA fused to the Fc region and His tag to the C-terminus thereof (10620-H03H, Sino Biological Inc.) ("human BCMA-Fc/His (1-54)"); and an antigen containing amino acid residues 4-48 of human BCMA (made in house, expressed in HEK293 cells) fused to the Fc region ("human BCMA-Fc (4-48)") were prepared.

Human BCMA-Fc (4-48) was prepared as follows. Polynucleotides encoding amino acid residues 4-48 of human BCMA were cloned into pAB1-Fc which is an animal cell expression vector including a CMV promoter. The cloned vector was transformed into HEK293E cells, and human BCMA-Fc (4-48) was purified using Protein A affinity chromatography. Human BCMA-Fc (1-51) was prepared in the same manner as described above.

1-2. Library Phage Preparation and Phage-Display Panning

Human-derived single-chain fragment variable (ScFv) phage library cells (Mol. Cells OT, 225-235, Feb. 28, 2009), which are able to bind to various antigens, were prepared. The prepared phage library was infected with the helper phage, and then, phage packing was induced. Thereafter, the culture product was centrifuged at 4,500 rpm for 15 minutes at 4° C., and then, 4% (w/v) PEG 6000 (Fluka, 81253) and 3% (w/v) NaCl (Sigma, S7653) were added to the supernatant and dissolved well, followed by incubating on ice for 1 hour. The resultant product was centrifuged at 4° C. at 8,000 rpm for 20 minutes, pellets were suspended in PBS, and then centrifuged again at 4° C. at 12,000 rpm for 10 minutes to obtain a supernatant containing a library phage. The obtained library phage was stored at 4° C. before use.

Panning was performed a total of three times in the following manner to screen for antibodies that are reactive to human BCMA or cross-reactive to human BCMA and monkey BCMA. 5 µg of the antigen prepared according to Example 1-1 was added to an immunotube (maxisorp 444202) and incubated at 4° C. for 16 hours to coat the surface of the test tube with a protein. The supernatant was removed therefrom, and bovine serum albumin (BSA) was added thereto to block nonspecific binding.

$10^{12}$ CFU of the phage library of prepared according to Example 1-2 was mixed with 1.5% (w/v) BSA, and the mixture was added to the target protein-coated immunoassay tube and reacted at 37° C. for 1 hour to allow a BCMA-specific phage to bind to the target protein. Subsequently, after multiple washing with a PBS-T (phosphate buffered saline including 0.05% (v/v) TWEEN® 20) solution, phages bound to BCMA were recovered by using a 100 mM triethylamine solution. The recovered phages were neutralized with 1M tris(hydroxymethyl)aminomethane (Tris) buffer (pH 7.4), and then, K12 ER2738 Escherichia coli was infected therewith, and the phages were recovered again. This cycle including target binding, eluting, neutralizing, infecting, and recovering was repeatedly performed four times. As the panning round progressed, the number of washing process using PBS-T was increased to amplify and concentrate the antigen-specific phage.

1-3. Single Clone Phage Antibody Screening

A single clone phage antibody screening procedure was performed to select, from a phage pool, a monoclonal antibody that specifically binds to BCMA.

Specifically, the phage pool obtained according to Example 1-2 was sequentially diluted, and cultured on a solid medium containing LB-tetracycline/cabenicillin to obtain single colonies. Each colony was cultured on a 96-deep well plate so that OD600 was from 0.5 to 0.7. 20 MOI of helper phage was added to each well, and reacted at 37° C. for 1 hour. Thereafter, kanamycin was added to each well and incubated overnight at 30° C. On the next day, the culture was centrifuged and the supernatant thereof was collected, and then, ELISA was performed to select BCMA-specific phages. Each well of the ELISA plate was coated with 100 ng of recombinant BCMA, and then incubated with PBS-B (3% BSA containing PBS) to prevent nonspecific binding. Thereafter, the plate was washed with PBS. The prepared single clone phage was added to each well and incubated at 37° C. for 1 hour, and the plate was washed three times with PBS-T. For detecting the bounded phages, horseradish peroxidase (HRP) conjugated anti-hemagglutinin (HA) antibody was added to each well. After washing step with PBS-T, tetramethylbenzidine (TMB, Sigma, T0440) was added. Clones, which are with an absorbance that is 0.5 or more at the wavelength of 450 nm and also the absorbance is at least 5 times greater than that of the control with anti-HA HRP alone, were selected. Four antibody clones (B58, 5B5, 5D5, and 5A6), which specifically bind to human BCMA, were selected.

From the nucleotide sequences encoding the selected antibodies, the amino acid sequences of the heavy chain variable region (SEQ ID NOs: 2 to 5) and the amino acid sequences of the light chain variable region (SEQ ID NOs: 6 to 9) were analyzed, and complementarity determining regions (CDR) was determined according to Kabat definition. The determined CDR amino acid sequences (N→C) of the heavy chains and light chains are shown in Tables 1 and 2, respectively.

TABLE 1

| Antibody | CDR-H1 | CDR-H2 | CDR-H3 |
|---|---|---|---|
| B58 | NYDMS (SEQ ID NO: 10) | WIYPSDSS IYYADSVK G (SEQ ID NO: 14) | RGPFANKY RQFDY (SEQ ID NO: 18) |
| 5B5 | GHYWS (SEQ ID NO: 11) | TVSGSGGD TFYADSVK G (SEQ ID NO: 15) | RGHSVMDV (SEQ ID NO: 19) |
| 5D5 | DYGLS (SEQ ID NO: 12) | LIDSSGSS TFYADSVK G (SEQ ID NO: 16) | KEHGLFDS (SEQ ID NO: 20) |
| 5A6 | NYGVH (SEQ ID NO: 13) | YISYSGGT YYNPSLKS (SEQ ID NO: 17) | RDSDDFGF DY (SEQ ID NO: 21) |

TABLE 2

| Antibody | CDR-L1 | CDR-L2 | CDR-L3 |
|---|---|---|---|
| B58 | SGSSSNIG SNSVS (SEQ ID NO: 22) | ADSKRPS (SEQ ID NO: 26) | GSWDYSLS GYV (SEQ ID NO: 29) |
| 5B5 | RASQGIDS YVA (SEQ ID NO: 23) | DASLRAT (SEQ ID NO: 27) | QQYNSWPI (SEQ ID NO: 30) |
| 5D5 | KASQDIDD DIN (SEQ ID NO: 24) | DASLRAT (SEQ ID NO: 27) | QQSLRTPI (SEQ ID NO: 31) |
| 5A6 | QGDSLRSY YVN (SEQ ID NO: 25) | DHSKRPT (SEQ ID NO: 28) | QSYDSSTV (SEQ ID NO: 32) |

Nucleotide sequence encoding heavy chain variable regions and nucleotide sequences encoding light chain variable regions are shown in Table 3 below.

TABLE 3

| Antibody | Nucleotide sequence encoding heavy chain variable region | Nucleotide sequence encoding light chain variable region |
|---|---|---|
| B58 | SEQ ID NO: 33 | SEQ ID NO: 37 |
| 5B5 | SEQ ID NO: 34 | SEQ ID NO: 38 |
| 5D5 | SEQ ID NO: 35 | SEQ ID NO: 39 |
| 5A6 | SEQ ID NO: 36 | SEQ ID NO: 40 |

1-4. Production of Anti-BCMA IgG Antibodies from Selected Anti-BCMA Phages

Polynucleotides having nucleotide sequences encoding the antibodies selected according to Example 1-3 were synthesized. The prepared polynucleotides were cloned into animal cell culture vectors (heavy chain expression vector: pAB1-HC, and light chain expression vector: pAB1-LC). Prepared were a total of 8 vectors containing polynucleotides encoding heavy and light chains for each of the four antibody clones (B58, 5A6, 5D5, and 5B5). Each of the prepared vectors for pAB1-HC contained an IgG1-type sequence.

CHO-S cells were cultured in a CD-CHO (Gibco, 10743) medium, and the prepared vectors were introduced into the CHO-S cells using polyethylenimine (PEI). Transduced CHO-S cells were cultured in CD-CHO medium for about 7 days at 8% $CO_2$, at 37° C. with shacking (110 rpm).

After collecting the cultured supernatant, then it was passed through a MABSELECT™ SURE™ column (GE healthcare, 5 mL) equilibrated with equilibration buffer (50 mM Tris-HCl, pH7.5, 100 mM NaCl) to allow the expressed antibody to bind to the column. The antibody was eluted with a solution of 50 mM Na-citrate (pH 3.4) and 100 mM NaCl, and then, neutralized using 1M Tris-HCl (pH 9.0) to obtain a final pH of 7.2. The buffer was then exchanged with PBS (pH 7.4) and the anti-BCMA IgG antibodies B58, 5A6, 5D5, and 5B5 were stored at 4° C. until use.

1-5. Preparation of Mutations of 5A6 and 5D5

In order to improve the productivity of the selected 5A6 and 5D5 antibodies, mutated antibodies were prepared in accordance with the nucleotide sequences of Table 3 by mutating one or two amino acid residues in the light chain CDR of the antibody.

The amino acid sequences of CDR-L1, CDR-L2, and CDR-L3 of the 5D5 mutant antibodies and the 5A6 mutant antibodies are shown in Table 4 and Table 5, respectively. In Tables 4 and 5, the underlined and bold amino acid residues are mutated moieties (WT: wild type, LM: light chain mutants). The light chain variable regions of the 5D5 mutant antibodies and the 5A6 mutant antibodies have the amino acid sequences of SEQ ID NOs: 41 to 45 and SEQ ID NOs: 46 to 53, respectively.

TABLE 4

| Antibody | CDR-L1 | CDR-L2 | CDR-L3 |
|---|---|---|---|
| 5D5 WT | KASQDIDD DIN (SEQ ID NO: 24) | DASLRAT (SEQ ID NO: 27) | QQSLRTPI (SEQ ID NO: 31) |
| 5D5 M1 | KASQDIDN DIN (SEQ ID NO: 54) | DASLRAT (SEQ ID NO: 27) | QQSLRTPI (SEQ ID NO: 31) |

TABLE 4-continued

| Antibody | CDR-L1 | CDR-L2 | CDR-L3 |
|---|---|---|---|
| 5D5 M2 | KASQDIDE DIN (SEQ ID NO: 55) | DASLRAT (SEQ ID NO: 27) | QQSLRTPI (SEQ ID NO: 31) |
| 5D5 M3 | KASQDIDA DIN (SEQ ID NO: 56) | DASLRAT (SEQ ID NO: 27) | QQSLRTPI (SEQ ID NO: 31) |
| 5D5 M4 | KASQDIDD AIN (SEQ ID NO: 57) | DASLRAT (SEQ ID NO: 27) | QQSLRTPI (SEQ ID NO: 31) |
| 515 M5 | KASQDIDD EIN (SEQ ID NO: 58) | DASLRAT (SEQ ID NO: 27) | QQSLRTPI (SEQ ID NO: 31) |

TABLE 5

| Antibody | CDR-L1 | CDR-L2 | CDR-L3 |
|---|---|---|---|
| 5A6 H | QGDSLRSY YVN (SEQ ID NO: 25) | DHSKRPT (SEQ ID NO: 28) | QSYDSSTV (SEQ ID NO: 32) |
| 5A6 M1 | QGESLRSY YVN (SEQ ID NO: 59) | DHSKRPT (SEQ ID NO: 28) | QSYDSSTV (SEQ ID NO: 32) |
| 5A6 M2 | QGDALRSY YVN (SEQ ID NO: 60) | DHSKRPT (SEQ ID NO: 28) | QSYDSSTV (SEQ ID NO: 32) |
| 5A6 M3 | QGDSLRSY YVN (SEQ ID NO: 25) | DHSKRPT (SEQ ID NO: 28) | QSYESSTV (SEQ ID NO: 63) |
| 5A6 M4 | QGDSLRSY YVN (SEQ ID NO: 25) | DHSKRPT (SEQ ID NO: 28) | QSYDASTV (SEQ ID NO: 64) |
| 5A6 M5 | QGESLRSY YVN (SEQ ID NO: 61) | DHSKRPT (SEQ ID NO: 28) | QSYESSTV (SEQ ID NO: 63) |
| 5A6 M6 | QGESLRSY YVN (SEQ ID NO: 61) | DHSKRPT (SEQ ID NO: 28) | QSYDASTV (SEQ ID NO: 64) |
| 5A6 M7 | QGDALRSY YVN (SEQ ID NO: 62) | DHSKRPT (SEQ ID NO: 28) | QSYESSTV (SEQ ID NO: 63) |

TABLE 5-continued

| Antibody | CDR-L1 | CDR-L2 | CDR-L3 |
|---|---|---|---|
| 5A6 M8 | QGDALRSY YVN (SEQ ID NO: 62) | DHSKRPT (SEQ ID NO: 28) | QSYDASTV (SEQ ID NO: 64) |

Example 2. Preparation of Anti-4-1BB Monoclonal Antibodies 2-1. Screening of Full Human Monoclonal Antibodies Against 4-11B1 (Phage Library Immunotube Panning)

For panning of the library against target molecules, a total of four rounds of panning were carried out using 4-1BB coated immunotubes.

Bacterial colonies from the $3^{rd}$ rounds of panning output were grown in SB medium containing carbenicilin in 96 deepwell plate until turbid, at which point $10^{11}$ pfu of VCSM13 helper phages were added to each well. After 1-hour infection at 37° C. with gentle shaking (80 rpm), 70 μg/mL of kanamycin was added and the cells were cultured overnight at 30° C. with shaking at 200 rpm.

Next day, the plates were centrifuged and the supernatants containing the phages were added to 4-1BB antigen-coated ELISA plates blocked with 3% (w/v) BSA in PBST. After 1-hour incubation at room temperature, the plates were washed three times with PBST, and anti-M13 antibody was added. The plates were incubated for 1 hour, washed three times with PBST, and the binding activity was measured using tetramethylbenzidine (TMB).

The 4-1BB specific antibodies were amplified for plasmid DNA sequencing. The regions of variable heavy chain and light chain (VH and VL) were analyzed to identify unique sequences and determine sequence diversity. Three antibody clones (41B01, 41B02, and AB41), which specifically bind to human 4-1BB, were selected. 41B01 M4, 41B01 M11, 41B01 M12, 41B01 M13, and 41B02 M1 mutants were prepared from the selected antibodies, as described in Example 1-5.

From the nucleotide sequences encoding the selected antibodies, the amino acid sequences of the antibody heavy chain variable region (SEQ ID NOs: 65 to 72) and the amino acid sequences of the light chain variable region (SEQ ID NOs: 73 to 80) were analyzed, and CDRs were determined according to Kabat definition. The determined CDR amino acid sequences (N→C) of the heavy chains and light chains are shown in Tables 6 and 7, respectively.

TABLE 6

| Antibody | CDR-H1 | CDR-H2 | CDR-H3 |
|---|---|---|---|
| 41B01 | SYDMS (SEQ ID NO: 81) | WISYSGGS IYYADSVK G (SEQ ID NO: 84) | DGQRNSMR EFDY (SEQ ID NO: 87) |
| 41B01 M4 | SYDMS (SEQ ID NO: 81) | WISYSGGS IYYADSVK G (SEQ ID NO: 84) | DAQRNSMR EFDY (SEQ ID NO: 88) |

TABLE 6-continued

| Antibody | CDR-H1 | CDR-H2 | CDR-H3 |
|---|---|---|---|
| 41B01 M11 | SYDMS (SEQ ID NO: 81) | WISYSGGS IYYADSVK G (SEQ ID NO: 84) | DAQRQSMR EFDY (SEQ ID NO: 89) |
| 41B01 M12 | SYDMS (SEQ ID NO: 81) | WISYSGGS IYYADSVK G (SEQ ID NO: 84) | DAQRNSMR EFDY (SEQ ID NO: 88) |
| 41B01 M13 | SYDMS (SEQ ID NO: 81) | WISYSGGS IYYADSVK G (SEQ ID NO: 84) | DAQRQSMR EFDY (SEQ ID NO: 89) |
| 41B02 | GYDMS (SEQ ID NO: 82) | VIYPDDGN TYYADSVK G (SEQ ID NO: 85) | HGGQKPTT KSSSAYGM DG (SEQ ID NO: 90) |
| 41B02 M1 | GYDMS (SEQ ID NO: 82) | VIYPDDGN TYYADSVK G (SEQ ID NO: 85) | HGGQKPTT KSSSAYGM DG (SEQ ID NO: 90) |
| AB41 | SYWMH (SEQ ID NO: 83) | EINPGNGH TNYNEKFK S (SEQ ID NO: 86) | SFTTARAF AY (SEQ ID NO: 91) |

TABLE 7

| Antibody | CDR-L1 | CDR-L2 | CDR-13 |
|---|---|---|---|
| 41B01 | SGSSSNIG NNYVT (SEQ ID NO: 92) | ADSHRPS (SEQ ID NO: 94) | ATWDYSLS GYV (SEQ ID NO: 96) |
| 41B01 M4 | SGSSSNIG NNYVT (SEQ ID NO: 92) | ADSHRPS (SEQ ID NO: 94) | ATWDYSLS GYV (SEQ ID NO: 96) |
| 41B01 M11 | SGSSSNIG NNYVT (SEQ ID NO: 92) | ADSHRPS (SEQ ID NO: 94) | ATWDYSLS GYV (SEQ ID NO: 96) |
| 41B01 M12 | SGSSSNIG NNYVT (SEQ ID NO: 92) | ADSHRPS (SEQ ID NO: 94) | ATWDYSLS GYV (SEQ ID NO: 96) |
| 41B01 M13 | SGSSSNIG NNYVT (SEQ ID NO: 92) | ADSHRPS (SEQ ID NO: 94) | ATWDYSLS GYV (SEQ ID NO: 96) |
| 41B02 | SGSSSNIG NNYVT (SEQ ID NO: 92) | ADSHRPS (SEQ ID NO: 94) | ATWDYSLS GYV (SEQ ID NO: 96) |
| 41B02 M1 | SGSSSNIG NNYVT (SEQ ID NO: 92) | ADSHRPS (SEQ ID NO: 94) | ATWDYSLS GYV (SEQ ID NO: 96) |

TABLE 7-continued

| Antibody | CDR-L1 | CDR-L2 | CDR-13 |
|---|---|---|---|
| AB41 | RASQTISD YLH (SEQ ID NO: 93) | YASQSI S (SEQ ID NO: 95) | QDGHSFPP T (SEQ ID NO: 97) |

2-2. Antigen Binding Abilities of Anti-4-1BB Antibodies to Human 4-1BB (1) Antigen Binding Measured by ELISA To evaluate the antigen binding activity, the antibody candidates were subjected to ELISA test. Briefly, microtiter plates were coated with human 4-1BB-Fc protein at 0.1 μg/mL in PBS, 100 μl/well at 4° C. overnight, then blocked with 100 μl/well of 5% (w/v) BSA. Five-fold dilutions of humanized antibodies 41B01 and 41B02 starting from 10 μg/mL were added to each well and incubated for 1-2 hours at RT. The plates were washed with PBS/TWEEN® and then incubate with goat-anti-human IgG antibody conjugated with Horse Radish Peroxidase (HRP) for 1 hour at RT. After washing, the plates were developed with TMB substrate and analyzed by spectrophotometer at OD 450-630 nm.

(2) Cell Binding Measured by FACS®

To evaluate the antigen binding property, the antibody candidates were analyzed for its binding to mammalian expressed 4-1BB by FACS®. Briefly, 4-1BB-Jurkat cells were incubated with antibodies (41B01 and 41B02). After wash by FACS® buffer (1% (w/v) BSA in PBS), the FITC-anti-human IgG antibody was added to each well and incubated at 4° C. for 1 hour. The MFI of FITC was evaluated by FACSCaliber®.

(3) Protein Kinetic for 4-1BB

To explore the binding kinetics of the humanized antibody, this example performed the affinity ranking by using Octet Red 96. As shown in Table 8 below, 41B01 and 41B02.

TABLE 8

| Antibody | KD (M) | kon(1/Ms) | kdis(1/s) | Chi | $R^2$ |
|---|---|---|---|---|---|
| 41B01 | 1.80E−10 | 6.58E+05 | 1.19E−04 | 0.0392 | 0.9987 |
| 41B02 | 1.01E−09 | 5.95E+05 | 6.03E−04 | 0.0525 | 0.9973 |

As shown in Table 8, the tested anti-4-1BB antibodies showed high 4-1BB binding affinities.

Example 3. Characterization of Anti-BCMA/Anti-4-1BB Bispecific Antibodies 3-1. Preparation of Bispecific Antibodies Anti-BCMA/Anti-4-1BB Bispecific Antibodies Various anti-BCMA/anti-4-1BB bispecific antibody candidates were prepared in full-length IgG (anti-BCMA antibody)-scFv(anti-4-1BB antibody) format as presented in Table 9. The constant region of the anti-BCMA antibody contained in the bispecific antibody can still be modified by introducing more than one mutation or change into human IgG1. In an example, NA mutation (N297A) has been introduced.

TABLE 9

| Bispecific antibody | Format |
|---|---|
| B58(NA)x41B01 | (NA)_(G4S)3_41B01 VH_(G4S)4_41B01 VL |
| B58(NA)x41B02 | (NA)_(G4S)3_41B02 VL_(G4S)4_41B02 VH |
| B58(NA)xAB41 | (NA)_(G4S)3_AB41 VL_(G4S)4_AB41 VH |
| 5A6(NA)x41B01 | (NA)_(G4S)3_41B01 VH_(G4S)4_41B01 VL |
| 5A6(NA)x41B02 | (NA)_(G4S)3_41B02 VL_(G4S)4_41B02 VH |
| 5A6(NA)xAB41 | (NA)_(G4S)3_AB41 VL_(G4S)4_AB41 VH |
| 5D5(NA)x41B01 | (NA)_(G4S)3_41B01 VH_(G4S)4_41B01 VL |
| 5D5(NA)x41B02 | (NA)_(G4S)3_41B02 VL_(G4S)4_41B02 VH |
| 5D5(NA)xAB41 | (NA)_(G4S)3_AB41 VL_(G4S)4_AB41 VH |
| 5B5(NA)x41B01 | (NA)_(G4S)3_41B01 VH_(G4S)4_41B01 VL |
| 5B5(NA)x41B02 | (NA)_(G4S)3_41B02 VL_(G4S)4_41B02 VH |
| 5B5(NA)xAB41 | (NA)_(G4S)3_AB41 VL_(G4S)4_AB41 VH |
| 5D5(NA)x41B01 M12 | (NA)_(GS)9_41B01 M12 VL_(G4S)4_41B01 M12 VH |
| 5D5M1(NA)x41B01 M12 | (NA)_(GS)9_41B01 M12 VL_(G4S)4_41B01 M12 VH |
| 5D5M2(NA)x41B01 M12 | (NA)_(GS)9_41B01 M12 VL_(GAS)4_41B01 M12 VH |
| 5D5M3(NA)x41B01 M12 | (NA)_(GS)9_41B01 M12 VL_(G4S)4_41B01 M12 VH |
| 5D5M4(NA)x41B01 M12 | (NA)_(GS)9_41B01 M12 VL_(GAS)4_41B01 M12 VH |
| 5D5M5(NA)x41B01 M12 | (NA)_(GS)9_41B01 M12 VL_(G4S)4_41B01 M12 VH |
| 5A6(NA)x41B01 M12 | (NA)_(GS)9_41B01 M12 VL_(G4S)4_41B01 M12 VH |
| 5A6M1(NA)x41B01 M12 | (NA)_(GS)9_41B01 M12 VL_(G4S)4_41B01 M12 VH |

TABLE 9-continued

| Bispecific antibody | Format |
|---|---|
| 5A6M2(NA)x41B01 M12 | (NA)_(GS)9_41B01 M12 VL_(G4S)4_41B01 M12 VH |
| 5A6M3(NA)x41B01 M12 | (NA)_(GS)9_41B01 M12 VL_(G4S)4_41B01 M12 VH |
| 5A6M4(NA)x41B01 M12 | (NA)_(GS)9_41B01 M12 VL_(G4S)4_41B01 M12 VH |
| 5A6M5(NA)x41B01 M12 | (NA)_(GS)9_41B01 M12 VL_(G4S)4_41B01 M12 VH |
| 5A6M6(NA)x41B01 M12 | (NA)_(GS)9_41B01 M12 VL_(G4S)4_41B01 M12 VH |
| 5A6M7(NA)x41B01 M12 | (NA)_(GS)9_41B01 M12 VL_(G4S)4_41B01 M12 VH |
| 5A6M8(NA)x41B01 M12 | (NA)_(GS)9_41B01 M12 VL_(G4S)4_41B01 M12 VH |

The anti-BCMA IgG and anti-4-1BB scFv clones prepared in Example 1 and Example 2, respectively, were exemplarily selected, to prepare anti-BCMA/anti-4-1BB bispecific antibodies in a IgG-scFv fusion form, in which a scFv antibody fragment of one antigen being fused to the c-terminal of IgG of another antigen. When BCMA is placed in full IgG part, IgG1 with ADCC reduced mutant backbone (N297A mutation; Cancer Cell, vol. 19, issue 1, pp. 101-113, etc.) was used, and when 4-1BB is placed in full IgG part, IgG4 was used. The amino acid sequences of anti-BCMA IgG and the 41BB scF scFv are presented in Table 10 and Table 11, respectively.

TABLE 10

| Antibody | Components | Amino acid sequence_HC: Fc(NA) |
|---|---|---|
| B58 | BCMA-Heavy Chain | EVQLLESGGGLVQPGGSLRLSCAASGFTFSNYDMSWVRQAPGKGLEWVSWIYPSD SSIYYADSVKGRFTISRDNSKNTLYLQMNSLRAEDTAVYYCARGPFANKYRQFDY WGQGTLVTVSSASTKGPSVFPLAPSSKSTSGGTAALGCLVKDYFPEPVTVSWNSG ALTSGVHTFPAVLQSSGLYSLSSVVTVPSSSLGTQTYICNVNHKPSNTKVDKKVE PKSCDKTHTCPPCPAPELLGGPSVFLFPPKPKDTLMISRTPEVTCVVVDVSHEDP EVKFNWYVDGVEVHNAKTKPREEQYASTYRVVSVLTVLHQDWLNGKEYKCKVSNK ALPAPIEKTISKAKGQPREPQVYTLPPSREEMTKNQVSLTCLVKGFYPSDIAVEW ESNGQPENNYKTTPPVLDSDGSFFLYSKLTVDKSRWQQGNVFSCSVMHEALHNHY TQKSLSLSPGK (SEQ ID NO: 100) |
| | BCMA-Light Chain | QSVLTQPPSASGTPGQRVTISCSGSSSNIGSNSVSWYQQLPGTAPKLLIYADSKR PSGVPDRFSGSKSGTSASLAISGLRSEDEADYYCGSWDYSLSGYVFGGGTKLTVL GQPKAAPSVTLFPPSSEELQANKATLVCLISDFYPGAVTVAWKADSSPVKAGVET TTPSKQSNNKYAASSYLSLTPEQWKSHRSYSCQVTHEGSTVEKTVAPAECS (SEQ ID NO: 101) |
| 5B5 | BCMA-Heavy Chain | EVQLLESGGGLVQPGGSLRLSCAASGFTFSGHYWSWVRQAPGKGLEWVSTVSGSG GDTFYADSVKGRFTISRDNSKNTLYLQMNSLRAEDTAVYYCARGHSVMDVWGQGT LVTVSSASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKVEPKSCD KTHTCPPCPAPELLGGPSVFLFPPKPKDTLMISRTPEVTCVVVDVSHEDPEVKFN WYVDGVEVHNAKTKPREEQYASTYRVVSVLTVLHQDWLNGKEYKCKVSNKALPAP IEKTISKAKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHNHYTQKSL SLSPGK (SEQ ID NO: 102) |
| | BCMA-Light Chain | EIVLTQSPGTLSLSPGERATLSCRASQGIDSYVAWYQQKPGQAPRLLIYDASLRA TGIPDRFSGSGSGTDFTLTISRLEPEDFAVYYCQQYNSWPITFGQGTKLEIKRTV AAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC (SEQ ID NO: 103) |
| 5D5 | BCMA-Heavy Chain | EVQLLESGGGLVQPGGSLRLSCAASGFTFSDYGLSWVRQAPGKGLEWVSLIDSSG SSTFYADSVKGRFTISRDNSKNTLYLQMNSLRAEDTAVYYCAKEHGLFDSWGQGT LVTVSSASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKVEPKSCD KTHTCPPCPAPELLGGPSVFLFPPKPKDTLMISRTPEVTCVVVDVSHEDPEVKFN WYVDGVEVHNAKTKPREEQYASTYRVVSVLTVLHQDWLNGKEYKCKVSNKALPAP IEKTISKAKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHNHYTQKSL SLSPGK (SEQ ID NO: 104) |

TABLE 10-continued

| Antibody | Components | Amino acid sequence_HC: Fc(NA) |
|---|---|---|
| | BCMA-Light Chain | EIVLTQSPGTLSLSPGERATLSCKASQDIDDDINWYQQKPGQAPRLLIYDASLRA TGIPDRFSGSGSGTDFTLTISRLEPEDFAVYYCQQSLRTPITFGQGTKLEIKRTV AAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC (SEQ ID NO: 105) |
| 5D5M1 | BCMA-Heavy Chain | EVQLLESGGGLVQPGGSLRLSCAASGFTFSDYGLSWVRQAPGKGLEWVSLIDSSG SSTFYADSVKGRFTISRDNSKNTLYLQMNSLRAEDTAVYYCAKEHGLFDSWGQGT LVTVSSASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKVEPKSCD KTHTCPPCPAPELLGGPSVFLFPPKPKDTLMISRTPEVTCVVVDVSHEDPEVKFN WYVDGVEVHNAKTKPREEQYASTYRVVSVLTVLHQDWLNGKEYKCKVSNKALPAP IEKTISKAKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHNHYTQKSL SLSPGK (SEQ ID NO: 104) |
| | BCMA-Light Chain | EIVLTQSPGTLSLSPGERATLSCKASQDIDNDINWYQQKPGQAPRLLIYDASLRA TGIPDRFSGSGSGTDFTLTISRLEPEDFAVYYCQQSLRTPITFGQGTKLEIKRTV AAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC (SEQ ID NO: 106) |
| 5D5M2 | BCMA-Heavy Chain | EVQLLESGGGLVQPGGSLRLSCAASGFTFSDYGLSWVRQAPGKGLEWVSLIDSSG SSTFYADSVKGRFTISRDNSKNTLYLQMNSLRAEDTAVYYCAKEHGLFDSWGQGT LVTVSSASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKVEPKSCD KTHTCPPCPAPELLGGPSVFLFPPKPKDTLMISRTPEVTCVVVDVSHEDPEVKFN WYVDGVEVHNAKTKPREEQYASTYRVVSVLTVLHQDWLNGKEYKCKVSNKALPAP IEKTISKAKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHNHYTQKSL SLSPGK (SEQ ID NO: 104) |
| | BCMA-Light Chain | EIVLTQSPGTLSLSPGERATLSCKASQDIDEDINWYQQKPGQAPRLLIYDASLRA TGIPDRFSGSGSGTDFTLTISRLEPEDFAVYYCQQSLRTPITFGQGTKLEIKRTV AAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC (SEQ ID NO: 107) |
| 5D5M3 | BCMA-Heavy Chain | EVQLLESGGGLVQPGGSLRLSCAASGFTFSDYGLSWVRQAPGKGLEWVSLIDSSG SSTFYADSVKGRFTISRDNSKNTLYLQMNSLRAEDTAVYYCAKEHGLFDSWGQGT LVTVSSASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKVEPKSCD KTHTCPPCPAPELLGGPSVFLFPPKPKDTLMISRTPEVTCVVVDVSHEDPEVKFN WYVDGVEVHNAKTKPREEQYASTYRVVSVLTVLHQDWLNGKEYKCKVSNKALPAP IEKTISKAKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHNHYTQKSL SLSPGK (SEQ ID NO: 104) |
| | BCMA-Light Chain | EIVLTQSPGTLSLSPGERATLSCKASQDIDADINWYQQKPGQAPRLLIYDASLRA TGIPDRFSGSGSGTDFTLTISRLEPEDFAVYYCQQSLRTPITFGQGTKLEIKRTV AAPSVFIFPPSDEQLKSGTASVVCLLNNFYPREAKVQWKVDNALQSGNSQESVTE QDSKDSTYSLSSTLILSKADYEKHKVYACEVTHQGLSSPVIKSFNRGEC (SEQ ID NO: 108) |
| 5D5M4 | BCMA-Heavy Chain | EVQLLESGGGLVQPGGSLRLSCAASGFTFSDYGLSWVRQAPGKGLEWVSLIDSSG SSTFYADSVKGRFTISRDNSKNTLYLQMNSLRAEDTAVYYCAKEHGLFDSWGQGT LVTVSSASTKGPSVFPLAPSSKSTSGGTAALGCLVKDYFPEPVTVSWNSGALTSG VHTFPAVLQSSGLYSLSSVVTYPSSSLGTQTYICNVNHKPSNTKVDKKVEPKSCD KTHTCPPCPAPELLGGPSVFLFPPKPKDTLMISRTPEVTCVVVDVSHEDPEVKFN WYVDGVEVHNAKTKPREEQYASTYRVVSVLTVLHQDWLNGKEYKCKVSNKALPAP IEKTISKAKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHNHYTQKSL SLSPGK (SEQ ID NO: 104) |
| | BCMA-Light Chain | EIVLTQSPGTLSLSPGERATLSCKASQDIDDAINWYQQKPGQAPRLLIYDASLRA TGIPDRFSGSGSGTDFTLTISRLEPEDFAVYYCQQSLRTPITFGQGTKLEIKRTV AAPSVFIFPPSDEQLKSGTASVVCLLNNFYPREAKVQWKVDNALQSGNSQESVTE QDSKDSTYSLSSTLTLSKADYEKHKVYACEVTHQGLSSPVIKSFNRGEC (SEQ ID NO: 109) |
| 5D5M5 | BCMA-Heavy Chain | EVQLLESGGGLVQPGGSLRLSCAASGFTFSDYGLSWVRQAPGKGLEWVSLIDSSG SSTFYADSVKGRFTISRDNSKNTLYLQMNSLRAEDTAVYYCAKEHGLFDSWGQGT LVTVSSASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKVEPKSCD KTHTCPPCPAPELLGGPSVFLFPPKPKDTLMISRTPEVTCVVVDVSHEDPEVKFN WYVDGVEVHNAKTKPREEQYASTYRVVSVLTVLHQDWLNGKEYKCKVSNKALPAP IEKTISKAKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHNHYTQKSL SLSPGK (SEQ ID NO: 104) |

TABLE 10-continued

| Antibody | Components | Amino acid sequence_HC: Fc(NA) |
|---|---|---|
| | BCMA-Light Chain | EIVLTQSPGTLSLSPGERATLSCKASQDIDDEINWYQQKPGQAPRLLIYDASLRA TGIPDRFSGSGSGTDFTLTISRLEPEDFAVYYCQQSLRTPITFGQGTKLEIKRTV AAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC (SEQ ID NO: 110) |
| 5A6 | BCMA-Heavy Chain | EVQLLESGGGLVQPGGSLRLSCAASGFTFSNYGVHWVRQAPGKGLEWVSYISYSG GTYYNPSLKSRFTISRDNSKNTLYLQMNSLRAEDTAVYYCARDSDDFGFDYWGQG TLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSC DKTHTCPPCPAPELLGGPSVFLFPPKPKDTLMISRTPEVTCVVVDVSHEDPEVKF NWYVDGVEVHNAKTKPREEQYASTYRVVSVLTVLHQDWLNGKEYKCKVSNKALPA PIEKTISKAKGQPREPQVYTLPPSREEMTKNQVSLTCLVKGFYPSDIAVEWESNG QPENNYKTTPPVLDSDGSFFLYSKLTVDKSRWQQGNVFSCSVMHEALHNHYTQKS LSLSPGK (SEQ ID NO: 111) |
| | BCMA-Light Chain | QSVLTQPPSASGTPGQRVTISCQGDSLRSYYVNWYQQLPGTAPKLLIYDHSKRPT GVPDRFSGSKSGTSASLAISGLRSEDEADYYCQSYDSSTVVFGGGTKLTVLGQPK AAPSVTLFPPSSEELQANKATLVCLISDFYPGAVTVAWKADSSPVKAGVETTTPS KQSNNKYAASSYLSLTPEQWKSHRSYSCQVTHEGSTVEKTVAPAECS (SEQ ID NO: 112) |
| 5A6M1 | BCMA-Heavy Chain | EVQLLESGGGLVQPGGSLRLSCAASGFTFSNYGVHWVRQAPGKGLEWVSYISYSG GTYYNPSLKSRFTISRDNSKNTLYLQMNSLRAEDTAVYYCARDSDDFGFDYWGQG TLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSC DKTHTCPPCPAPELLGGPSVFLFPPKPKDTLMISRTPEVTCVVVDVSHEDPEVKF NWYVDGVEVHNAKTKPREEQYASTYRVVSVLTVLHQDWLNGKEYKCKVSNKALPA PIEKTISKAKGQPREPQVYTLPPSREEMTKNQVSLTCLVKGFYPSDIAVEWESNG QPENNYKTTPPVLDSDGSFFLYSKLTVDKSRWQQGNVFSCSVMHEALHNHYTQKS LSLSPGK (SEQ ID NO: 111) |
| | BCMA-Light Chain | QSVLTQPPSASGTPGQRVTISCQGESLRSYYVNWYQQLPGTAPKLLIYDHSKRPT GVPDRFSGSKSGTSASLAISGLRSEDEADYYCQSYDSSTVVFGGGTKLTVLGQPK AAPSVTLFPPSSEELQANKATLVCLISDFYPGAVTVAWKADSSPVKAGVETTTPS KQSNNKYAASSYLSLTPEQWKSHRSYSCQVTHEGSTVEKTVAPAECS (SEQ ID NO: 113) |
| 5A6M2 | BCMA-Heavy Chain | EVQLLESGGGLVQPGGSLRLSCAASGFTFSNYGVHWVRQAPGKGLEWVSYISYSG GTYYNPSLKSRFTISRDNSKNTLYLQMNSLRAEDTAVYYCARDSDDFGFDYWGQG TLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSC DKTHTCPPCPAPELLGGPSVFLFPPKPKDTLMISRTPEVTCVVVDVSHEDPEVKF NWYVDGVEVHNAKTKPREEQYASTYRVVSVLTVLHQDWLNGKEYKCKVSNKALPA PIEKTISKAKGQPREPQVYTLPPSREEMTKNQVSLTCLVKGFYPSDIAVEWESNG QPENNYKTTPPVLDSDGSFFLYSKLTVDKSRWQQGNVFSCSVMHEALHNHYTQKS LSLSPGK (SEQ ID NO: 111) |
| | BCMA-Light Chain | QSVLTQPPSASGTPGQRVTISCQGDALRSYYVNWYQQLPGTAPKLLIYDHSKRPT GVPDRFSGSKSGTSASLAISGLRSEDEADYYCQSYDSSTVVFGGGTKLTVLGQPK AAPSVTLFPPSSEELQANKATLVCLISDFYPGAVTVAWKADSSPVKAGVETTTPS KQSNNKYAASSYLSLTPEQWKSHRSYSCQVTHEGSTVEKTVAPAECS (SEQ ID NO: 114) |
| 5A6M3 | BCMA-Heavy Chain | EVQLLESGGGLVQPGGSLRLSCAASGFTFSNYGVHWVRQAPGKGLEWYSYISYSG GTYYNPSLKSRFTISRDNSKNTLYLQMNSLRAEDTAVYYCARDSDDFGFDYWGQG TLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSC DKTHTCPPCPAPELLGGPSVFLEPPKPKDTLMISRTPEVTCVVVDVSHEDPEVKF NWYVDGVEVHNAKTKPREEQYASTYRVVSVLTVLHQDWLNGKEYKCKVSNKALPA PIEKTISKAKGQPREPQVYTLPPSREEMTKNQVSLTCLVKGFYPSDIAVEWESNG QPENNYKTTPPVLDSDGSFFLYSKLTVDKSRWQQGNVFSCSVMHEALHNHYTQKS LSLSPGK (SEQ ID NO: 111) |
| | BCMA-Light Chain | QSVLTQPPSASGTPGQRVTISCQGDSLRSYYVNWYQQLPGTAPKLLIYDHSKRPT GVPDRFSGSKSGTSASLAISGLRSEDEADYYCQSYESSTVVFGGGTKLTVLGQPK AAPSVTLFPPSSEELQANKATLVCLISDFYPGAVTVAWKADSSPVKAGVETTTPS KQSNNKYAASSYLSLTPEQWKSHRSYSCQVTHEGSTVEKTVAPAECS (SEQ ID NO: 115) |
| 5A6M4 | BCMA-Heavy Chain | EVQLLESGGGLVQPGGSLRLSCAASGFTFSNYGVHWVRQAPGKGLEWVSYISYSG GTYYNPSLKSRFTISRDNSKNTLYLQMNSLRAEDTAVYYCARDSDDFGFDYWGQG TLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSC DKTHTCPPCPAPELLGGPSVFLFPPKPKDTLMISRTPEVTCVVVDVSHEDPEVKF NWYVDGVEVHNAKTKPREEQYASTYRVVSVLTVLHQDWLNGKEYKCKVSNKALPA PIEKTISKAKGQPREPQVYTLPPSREEMTKNQVSLTCLVKGFYPSDIAVEWESNG QPENNYKTTPPVLDSDGSFFLYSKLTVDKSRWQQGNVFSCSVMHEALHNHYTQKS LSLSPGK (SEQ ID NO: 111) |

TABLE 10-continued

| Antibody | Components | Amino acid sequence_HC: Fc(NA) |
|---|---|---|
| | BCMA-Light Chain | QSVLTQPPSASGTPGQRVTISCQGDSLRSYYVNWYQQLPGTAPKLLIYDHSKRPT GVPDRFSGSKSGTSASLAISGLRSEDEADYYCQSYDASTVVFGGGTKLTVLGQPK AAPSVTLFPPSSEELQANKATLVCLISDFYPGAVTVAWKADSSPVKAGVETTTPS KQSNNKYAASSYLSLTPEQWKSHRSYSCQVTHEGSTVEKTVAPAECS (SEQ ID NO: 116) |
| 5A6M5 | BCMA-Heavy Chain | EVQLLESGGGLVQPGGSLRLSCAASGFTFSNYGVHWVRQAPGKGLEWVSYISYSG GTYYNPSLKSRFTISRDNSKNTLYLQMNSLRAEDTAVYYCARDSDDFGFDYWGQG TLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSC DKTHTCPPCPAPELLGGPSVFLFPPKPKDTLMISRTPEVTCVVVDVSHEDPEVKF NWYVDGVEVHNAKTKPREEQYASTYRVVSVLTVLHQDWLNGKEYKCKVSNKALPA PIEKTISKAKGQPREPQVYTLPPSREEMTKNQVSLTCLVKGFYPSDIAVEWESNG QPENNYKTTPPVLDSDGSFFLYSKLTVDKSRWQQGNVFSCSVMHEALHNHYTQKS LSLSPGK (SEQ ID NO: 111) |
| | BCMA-Light Chain | QSVLTQPPSASGTPGQRVTISCQGESLRSYYVNWYQQLPGTAPKLLIYDHSKRPT GVPDRFSGSKSGTSASLAISGLRSEDEADYYCQSYESSTVVFGGGGTKLTVLGQPK AAPSVTLFPPSSEELQANKATLVCLISDFYPGAVTVAWKADSSPVKAGVETTTPS KQSANKYAASSYLSLTPEQWKSHRSYSCQVTHEGSTVEKTVAPAECS (SEQ ID NO: 117) |
| 5A6M6 | BCMA-Heavy Chain | EVQLLESGGGLVQPGGSLRLSCAASGFTFSNYGVHWVRQAPGKGLEWVSYISYSG GTYYNPSLKSRFTISRDNSKNTLYLQMNSLRAEDTAVYYCARDSDDFGFDYWGQG TLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSC DKTHTCPPCPAPELLGGPSVFLFPPKPKDTLMISRTPEVTCVVVDVSHEDPEVKF NWYVDGVEVHNAKTKPREEQYASTYRVVSVLTVLHQDWLNGKEYKCKVSNKALPA PIEKTISKAKGQPREPQVYTLPPSREEMTKNQVSLTCLVKGFYPSDIAVEWESNG QPENNYKTTPPVLDSDGSFFLYSKLTVDKSRWQQGNVFSCSVMHEALHNHYTQKS LSLSPGK (SEQ ID NO: 111) |
| | BCMA-Light Chain | QSVLTQPPSASGTPGQRVTISCQGESLRSYYVNWYQQLPGTAPKLLIYDHSKRPT GVPDRESGSKSGTSASLAISGLRSEDEADYYCQSYDASTVVFGGGTKLTVLGQPK AAPSVTLFPPSSEELQANKATLVCLISDFYPGAVTVAWKADSSPVKAGVETTTPS KQSNNKYAASSYLSLTPEQWKSHRSYSCQVTHEGSTVEKTVAPAECS (SEQ ID NO: 118) |
| 5A6M7 | BCMA-Heavy Chain | EVQLLESGGGLVQPGGSLRLSCAASGFTFSNYGVHWVRQAPGKGLEWVSYISYSG GTYYNPSLKSRFTISRDNSKNTLYLQMNSLRAEDTAVYYCARDSDDFGFDYWGQG TLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSC DKTHTCPPCPAPELLGGPSVFLFPPKPKDTLMISRTPEVTCVVVDVSHEDPEVKF NWYVDGVEVHNAKTKPREEQYASTYRVVSVLTVLHQDWLNGKEYKCKVSNKALPA PIEKTISKAKGQPREPQVYTLPPSREEMTKNQVSLTCLVKGFYPSDIAVEWESNG QPENNYKTTPPVLDSDGSFFLYSKLTVDKSRWQQGNVFSCSVMHEALHNHYTQKS LSLSPGK (SEQ ID NO: 111) |
| | BCMA-Light Chain | QSVLTQPPSASGTPGQRVTISCQGDALRSYYVNWYQQLPGTAPKLLIYDHSKRPT GVPDRFSGSKSGTSASLAISGLRSEDEADYYCQSYESSTVVFGGGTKLTVLGQPK AAPSVTLFPPSSEELQANKATLVCLISDFYPGAVTVAWKADSSPVKAGVETTTPS KQSNNKYAASSYLSLTPEQWKSHRSYSCQVTHEGSTVEKTVAPAECS (SEQ ID NO: 119) |
| 5A6M8 | BCMA-Heavy Chain | EVQLLESGGGLVQPGGSLRLSCAASGFTFSNYGVHWVRQAPGKGLEWVSYISYSG GTYYNPSLKSRFTISRDNSKNTLYLQMNSLRAEDTAVYYCARDSDDFGFDYWGQG TLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSC DKTHTCPPCPAPELLGGPSVFLFPPKPKDTLMISRTPEVTCVVVDVSHEDPEVKF NWYVDGVEVHNAKTKPREEQYASTYRVVSVLTVLHQDWLNGKEYKCKVSNKALPA PIEKTISKAKGQPREPQVYTLPPSREEMTKNQVSLTCLVKGFYPSDIAVEWESNG QPENNYKTTPPVLDSDGSFFLYSKLTVDKSRWQQGNVFSCSVMHEALHNHYTQKS LSLSPGK (SEQ ID NO: 111) |
| | BCMA-Light Chain | QSVLTQPPSASGTPGQRVTISCQGDALRSYYVNWYQQLPGTAPKLLIYDHSKRPT GVPDRFSGSKSGTSASLAISGLRSEDEADYYCQSYDASTVVFGGGTKLTVLGQPK AAPSVTLFPPSSEELQANKATLVCLISDFYPGAVTVAWKADSSPVKAGVETTTPS KQSNNKYAASSYLSLTPEQWKSHRSYSCQVTHEGSTVEKTVAPAECS (SEQ ID NO: 120) |

TABLE 11

| Antibody | Amino acid sequence (VL-L-VH constructs) |
|---|---|
| 41B01 scFV | QSVLTQPPSASGTPGRRVTISCSGSSSNIGNNYVTWYQQLPGTAPKELIYADSHRPS GVPDRFSGSKSGTSASLAISGLRSEDEADYYCATWDYSLSGYVFGCGTKLTVLGGGG SGGGGSGGGGSGGGGSEVQLLESGGGLVQPGGSLRLSCAASGFTFSSYDMSWVRQAP GKCLEWVSWISYSGGSIYYADSVKGRFTISRDNSKNTLYLQMNSLRAEDTAVYYCAR DGQRNSMREFDYWGQGTLVTVSS (SEQ ID NO: 121) |

TABLE 11-continued

| Antibody | Amino acid sequence (VL-L-VH constructs) |
| --- | --- |
| 41B01 M4 scFV | QSVLTQPPSASGTPGRRVTISCSGSSSNIGNNYVTWYQQLPGTAPKLLIYADSHRPS<br>GVPDRFSGSKSGTSASLAISGLRSEDEADYYCATWDYSLSGYVFGCGTKLTVLGGGG<br>SGGGGSGGGGSGGGGSEVQLLESGGGLVQPGGSLRLSCAASGFTFSSYDMSWVRQAP<br>GKCLEWVSWISYSGGSIYYADSVKGRFTISRDNSKNTLYLQMNSLRAEDTAVYYCAR<br>DAQRNSMREFDYWGQGTLVTVSS (SEQ ID NO: 122) |
| 41B01 M11 scFV | QSVLTQPPSASGTPGRRVTISCSGSSSNIGNNYVTWYQQLPGTAPKLLIYADSHRPS<br>GVPDRFSGSKSGTSASLAISGLRSEDEADYYCATWDYSLSGYVFGCGTKLTVLGGGG<br>SGGGGSGGGGSGGGGSEVQLLESGGGLVQPGGSLRLSCAASGFTFSSYDMSWVRQAP<br>GKCLEWVSWISYSGGSIYYADSVKGRFTISRDNSKNTLYLQMNSLRAEDTAVYYCAR<br>DAQRQSMREFDYWGQGTLVTVSS (SEQ ID NO: 123) |
| 41B01 M12 scFV | QSVLTQPPSASGTPGQRVTISCSGSSSNIGNNYVTWYQQLPGTAPKLLIYADSHRPS<br>GVPDRFSGSKSGTSASLAISGLRSEDEADYYCATWDYSLSGYVFGCGTKLTVLGGGG<br>SGGGGSGGGGSGGGGSEVQLLESGGGLVQPGGSLRLSCAASGFTFSSYDMSWVRQAP<br>GKCLEWVSWISYSGGSIYYADSVKGRFTISRDNSKNTLYLQMNSLRAEDTAVYYCAR<br>DAQRNSMREFDYWGQGTLVTVSS (SEQ ID NO: 124) |
| 41B01 M13 scFV | QSVLTQPPSASGTPGQRVTISCSGSSSNIGNNYVTWYQQLPGTAPKLLIYADSHRPS<br>GVPDRFSGSKSGTSASLAISGLRSEDEADYYCATWDYSLSGYVFGCGTKLTVLGGGG<br>SGGGGSGGGGSGGGGSEVQLLESGGGLVQPGGSLRLSCAASGFTFSSYDMSWVRQAP<br>GKCLEWVSWISYSGGSIYYADSVKGRFTISRDNSKNTLYLQMNSLRAEDTAVYYCAR<br>DAQRQSMREFDYWGQGTLVTVSS (SEQ ID NO: 125) |
| 41B02 scFV | QSVLTQPPSASGTPGRRVTISCSGSSSNIGNNYVTWYQQLPGTAPKLLIYADSHRPS<br>GVPDRFSGSKSGTSASLAISGLRSEDEADYYCATWDYSLSGYVFGCGTKLTVLGGGG<br>SGGGGSGGGGSGGGGSEVQLLESGGGLVQPGGSLRLSCAASGFTFSGYDMSWVRQAP<br>GKCLEWVSVIYPDDGNTYYADSVKGRFTISRDNSKNTLYLQMNSLRAEDAAVYYCAK<br>HGGQKPTTKSSSAYGMDGWGQGTLVTVSS (SEQ ID NO: 126) |
| 41B02 M1 scFV | QSVLTQPPSASGTPGQRVTISCSGSSSNIGNNYVTWYQQLPGTAPKLLIYADSHRPS<br>GVPDRFSGSKSGTSASLAISGLRSEDEADYYCATWDYSLSGYVFGCGTKLTVLGGGG<br>SGGGGSGGGGSGGGGSEVQLLESGGGLVQPGGSLRLSCAASGFTFSGYDMSWVRQAP<br>GKCLEWVSVIYPDDGNTYYADSVKGRFTISRDNSKNTLYLQMNSLRAEDTAVYYCAK<br>HGGQKPTTKSSSAYGMDGWGQGTLVTVSS (SEQ ID NO: 127) |
| AB41 scFV | DIVMTQSPAFLSVTPGEKVTITCRASQTISDYLHWYQQKPDQAPKLLIKYASQSISG<br>IPSRFSGSGSGTDFTFTISSLEAEDAATYYCQDGHSFPPTFGCGTKLEIKRGGGGSG<br>GGGSGGGGSGGGGSQVQLQQSGAEVIKPGASVKLSCKASGYTFSSYWMHWVRQAPGQ<br>CLEWIGEINPGNGHTNYNEKFKSRATLTGDTSTSTVYMELSSLRSEDTAVYYCARSF<br>TTARAFAYWGQGTLVTVSS (SEQ ID NO: 128) |

A DNA segment 1 having a nucleotide sequence encoding a heavy chain of an IgG antibody of the anti-BCMA/anti-4-1BB bispecific antibody was inserted into pcDNA3.4 (Invitrogen, A14697; plasmid 1), and a DNA segment 2 having a nucleotide sequence encoding a light chain of an IgG antibody of the anti-BCMA/anti-4-1BB bispecific antibody was inserted into pcDNA 3.4 (Invitrogen, A14697; plasmid 2). Thereafter, a DNA segment 3 encoding a scFv was fused at a part of the DNA segment 1 corresponding to the c-terminus of the Fc region of the IgG antibody inserted into the plasmid 1, using a DNA segment 4 encoding a linker peptide having 15 amino acid lengths consisting of (GGGGS)4 (SEQ ID NO: 98) or using a DNA segment 5 encoding a linker peptide having 18 amino acid lengths consisting of (GS)9 (SEQ ID NO: 99), to construct vectors for the expression of bispecific antibodies. Furthermore, in order to stabilize scFv, as described in Example 2, additional modification was applied to generate disulfide bridge fusing VL103-VH44(VL103: VL having G→C mutation at the position 103; VH 44: VH having G→C mutation at the position 44) to C-terminus of light chain and C-terminus of heavy chain, respectively.

The amino acid sequences of the prepared bispecific antibodies are presented in Table 12.

TABLE 12

| bispecific antibody | | component | | Amino acid sequence | Amino acid sequence of bispecific antibody |
| --- | --- | --- | --- | --- | --- |
| 5D5M4 (NA) x41B01 M12 | Heavy com-ponent | Heavy chain of anti-BCMA | BCMA-Heavy Chain (NA) | EVQLLESGGGLVQPGGSLRLSC<br>AASGFTFSDYGLSWVRQAPGKG<br>LEWYSLIDSSGSSTFYADSVKG<br>RFTISRDNSKNTLYLQMNSLRA<br>EDTAVYYCAKEHGLFDSWGQGT<br>LVTVSSASTKGPSVFPLAPSSK<br>STSGGTAALGCLVKDYFPEPVT<br>VSWNSGALTSGVHTFPAVLQSS<br>GLYSLSSVVTVPSSSLGTQTYI<br>CNVNHKPSNTKVDKKVEPKSCD<br>KTHTCPPCPAPELLGGPSVFLF<br>PPKPKDTLMISRTPEVTCVVVD | EVQLLESGGGLVQPGGSLRLSC<br>AASGFTFSDYGLSWVRQAPGKG<br>LEWVSLIDSSGSSTFYADSVKG<br>RFTISRDNSKNTLYLQMNSLRA<br>EDTAVYYCAKEHGLFDSWGQGT<br>LVTVSSASTKGPSVFPLAPSSK<br>STSGGTAALGCLVKDYFPEPVT<br>VSWNSGALTSGVHTFPAVLQSS<br>GLYSLSSVVTVPSSSLGTQTYI<br>CNVNHKPSNTKVDKKVEPKSCD<br>KTHTCPPCPAPELLGGPSVFLF<br>PPKPKDTLMISRTPEVTCVVVD |

TABLE 12-continued

| bispecific antibody | component | | | Amino acid sequence | Amino acid sequence of bispecific antibody |
|---|---|---|---|---|---|
| | | | | VSHEDPEVKFNWYVDGVEVHNA KTKPREEQYASTYRVVSVLTVL HQDWLNGKEYKCKVSNKALPAP IEKTISKAKGQPREPQVYTLPP SREEMTKNQVSLTCLVKGFYPS DIAVEWESNGQPENNYKTTPPV LDSDGSFFLYSKLTVDKSRWQQ GNVFSCSVMHEALHNHYTQKSL SLSPGK (SEQ ID NO: 104) | VSHEDPEVKFNWYVDGVEVHNA KTKPREEQYASTYRVVSVLTVL HQDWLNGKEYKCKVSNKALPAP IEKTISKAKGQPREPQVYTLPP SREEMTKNQVSLTCLVKGFYPS DIAVEWESNGQPENNYKTTPPV LDSDGSFFLYSKLTVDKSRWQQ GNVFSCSVMHEALHNHYTQKSL SLSPGKGSGSGSGSGSGSGSGS GSQSVLTQPPSASGTPGQRVTI SCSGSSSNIGNNYVTWYQQLPG TAPKLLIYADSHRPSGVPDRFS GSKSGTSASLAISGLRSEDEAD YYCATWDYSLSGYVFGCGTKLT VLGGGGSGGGGSGGGGSGGGGS EVQLLESGGGLVQPGGSLRLSC AASGFTFSSYDMSWVRQAPGKC LEWVSWISYSGGSIYYADSVKG RFTISRDNSKNTLYLQMNSLRA EDTAVYYCARDAQRNSMREFDY WGQGTLVTVSS (SEQ ID NO: 129) |
| | | Linker | (GS)9 | GSGSGSGSGSGSGSGSGS (SEQ ID NO: 99) | |
| | | scFv of anti-4-1BB anti-body | 41B01 M12 VL-(GGGG S)4-41B01 M12 VH | QSVLTQPPSASGTPGQRVTISC SGSSSNIGNNYVTWYQQLPGTA PKLLIYADSHRPSGVPDRFSGS KSGTSASLAISGLRSEDEADYY CATWDYSLSGYVFGCGTKLTVL GGGGSGGGGSGGGGSGGGGSEV QLLESGGGLVQPGGSLRLSCAA SGFTFSSYDMSWVRQAPGKCLE WVSWISYSGGSIYYADSVKGRF TISRDNSKNTLYLQMNSLRAED TAVYYCARDAQRNSMREFDYWG QGTLVTVSS (SEQ ID NO: 124) | |
| | Light com-po-nent | Light chain of anti-BCMA | BCMA-Light Chain | EIVLTQSPGTLSLSPGERATLS CKASQDIDDAINWYQQKPGQAP RLLIYDASLRATGIPDRFSGSG SGTDFTLTISRLEPEDFAVYYC QQSLRTPITFGQGTKLEIKRTV AAPSVFIFPPSDEQLKSGTASV VCLLNNFYPREAKVQWKVDNAL QSGNSQESVTEQDSKDSTYSLS STLTLSKADYEKHKVYACEVTH QGLSSPVTKSFNRGEC (SEQ ID NO: 109) | EIVLTQSPGTLSLSPGERATLS CKASQDIDDAINWYQQKPGQAP RLLIYDASLRATGIPDRESGSG SGTDFTLTISRLEPEDFAVYYC QQSLRTPITFGQGTKLEIKRTV AAPSVFIFPPSDEQLKSGTASV VCLLNNFYPREAKVQWKVDNAL QSGNSQESVTEQDSKDSTYSLS STLTLSKADYEKHKVYACEVTH QGLSSPVTKSFNRGEC (SEQ ID: NO: 109) |
| 5A6M6(NA) x41B01 M12 | Heavy com-po-nent | Heavy chain of anti-BCMA | BCMA-Heavy Chain (NA) | EVQLLESGGGLVQPGGSLRLSC AASGFTFSNYGVHWVRQAPGKG LEWVSYISYSGGTYYNPSLKSR FTISRDNSKNTLYLQMNSLRAE DTAVYYCARDSDDFGFDYWGQG TLVTVSSASTKGPSVFPLAPSS KSTSGGTAALGCLVKDYFPEPV TVSWNSGALTSGVHTFPAVLQS SGLYSLSSVVTVPSSSLGTQTY ICNVNHKPSNTKVDKKVEPKSC DKTHTCPPCPAPELLGGPSVFL FPPKPKDTLMISRTPEVTCVVV DVSHEDPEVKFNWYVDGVEVHN AKTKPREEQYASTYRVVSVLTV LHQDWLNGKEYKCKVSNKALPA PIEKTISKAKGQPREPQVYTLP PSREEMTKNQVSLTCLVKGFYP SDIAVEWESNGQPENNYKTTPP VLDSDGSFFLYSKLTVDKSRWQ QGNVFSCSVMHEALHNHYTQKS LSLSPGK (SEQ ID NO: 111) | EVQLLESGGGLVQPGGSLRLSC AASGFTFSNYGVHWVRQAPGKG LEWVSYISYSGGTYYNPSLKSR FTISRDNSKNTLYLQMNSLRAE DTAVYYCARDSDDFGFDYWGQG TLVTVSSASTKGPSVFPLAPSS KSTSGGTAALGCLVKDYFPEPV TVSWNSGALTSGVHTFPAVLQS SGLYSLSSVVTVPSSSLGTQTY ICNVNHKPSNTKVDKKVEPKSC DKTHTCPPCPAPELLGGPSVFL FPPKPKDTLMISRTPEVTCVVV DVSHEDPEVKFNWYVDGVEVHN AKTKPREEQYASTYRVVSVLTV LHQDWLNGKEYKCKVSNKALPA PIEKTISKAKGQPREPQVYTLP PSREEMTKNQVSLTCLVKGFYP SDIAVEWESNGQPENNYKTTPP VLDSDGSFFLYSKLTVDKSRWQ QGNVFSCSVMHEALHNHYTQKS LSLSPGKGSGSGSGSGSGSGSG SGSQSVLTQPPSASGTPGQRVT ISCSGSSSNIGNNYVTWYQQLP GTAPKLLIYADSHRPSGVPDRF SGSKSGTSASLAISGLRSEDEA DYYCATWDYSLSGYVFGCGTKL TVLGGGGSGGGGSGGGGSGGGG SEVQLLESGGGLVQPGGSLRLS CAASGFTFSSYDMSWVRQAPGK CLEWYSWISYSGGSIYYADSVK GRFTISRDNSKNTLYLQMNSLR AEDTAVYYCARDAQRNSMREFD YWGQGTLVTVSS (SEQ ID NO: 130) |
| | | Linker | (GS)9 | GSGSGSGSGSGSGSGSGS (SEQ ID NO: 99) | |
| | | scFv of anti-4-1BB antib ody | 41B01 M12 VL-(GGGG S)4-41B01 M12 VH | QSVLTQPPSASGTPGQRVTISC SGSSSNIGNNYVTWYQQLPGTA PKLLIYADSHRPSGVPDRFSGS KSGTSASLAISGLRSEDEADYY CATWDYSLSGYVFGCGTKLTVL GGGGSGGGGSGGGGSGGGGSEV QLLESGGGLVQPGGSLRLSCAA SGFTFSSYDMSWVRQAPGKCLE WVSWISYSGGSIYYADSVKGRF TISRDNSKNTLYLQMNSLRAED TAVYYCARDAQRNSMREFDYWG QGTLVTVSS (SEQ ID NO: 124) | |

TABLE 12-continued

| bispecific antibody | component | | | Amino acid sequence | Amino acid sequence of bispecific antibody |
|---|---|---|---|---|---|
| | Light com-po-nent | Light chain of anti-BCMA | BCMA-Light Chain | QSVLTQPPSASGTPGQRVTISC QGESLRSYYVNWYQQLPGTAPK LLIYDHSKRPTGVPDRFSGSKS GTSASLAISGLRSEDEADYYCQ SYDASTVVFGGGTKLTVLGQPK AAPSVTLEPPSSEELQANKATL VCLISDFYPGAVTVAWKADSSP VKAGVETTTPSKQSNNKYAASS YLSLTPEQWKSHRSYSCQVTHE GSTVEKTVAPAECS (SEQ ID NO: 118) | QSVLTQPPSASGTPGQRVTISC QGESLRSYYVNWYQQLPGTAPK LLIYDHSKRPTGVPDRFSGSKS GTSASLAISGLRSEDEADYYCQ SYDASTVVFGGGTKLTVLGQPK AAPSVTLFPPSSEELQANKATL VCLISDFYPGAVTVAWKADSSP VKAGVETTTPSKQSNNKYAASS YLSLTPEQWKSHRSYSCQVTHE GSTVEKTVAPAECS (SEQ ID NO: 118) |

One or more than one point mutations in amino acid sequences can be applied in the antibodies presented below, for the purpose of improved stability and potency, decreased immunogenicity, and etc.

3-2. Antigen Binding Abilities of Anti-BCMA/Anti-4-1BB Antibodies (Full-Length IgG Form) to Target Protein (1) Antigen Binding Measured by DACE (Dual Antigen Captured ELISA)

To evaluate the antigen binding activity, the antibody candidates were subjected to ELISA test. Briefly, microtiter plates were coated with human BCMA-Fc protein at 0.5 $\mu$g/mL in PBS, to 100 $\mu$l/well at 4° C. overnight, and then blocked with 100 $\mu$l/well of 1% (w/v) BSA. Three-fold dilutions of bispecific antibodies starting from 20 $\mu$g/mL were added to each well and incubated for 1 hour at 37° C. The plates were washed with PBS/TWEEN® and then incubate with 1% (w/v) BSA contained human 4-1BB his protein 0.8 $\mu$g/mL for 1 hour at 37° C. The plates were washed with PBST (0.05% (v/v) TWEEN® 20 in PBS). And then the plate was developed with TMB substrate and analyzed by spectrophotometer at OD 450-630 nm.

Figure 2A:
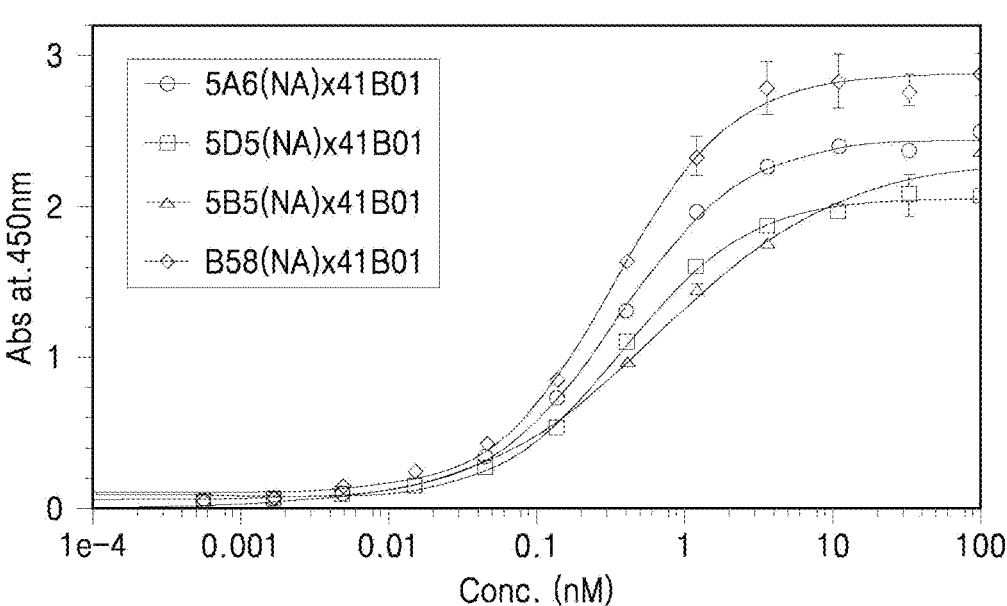
FIGS. 2a, 2b and 2c are graphs showing results of a target protein binding test using DACE.
Figure 2B:
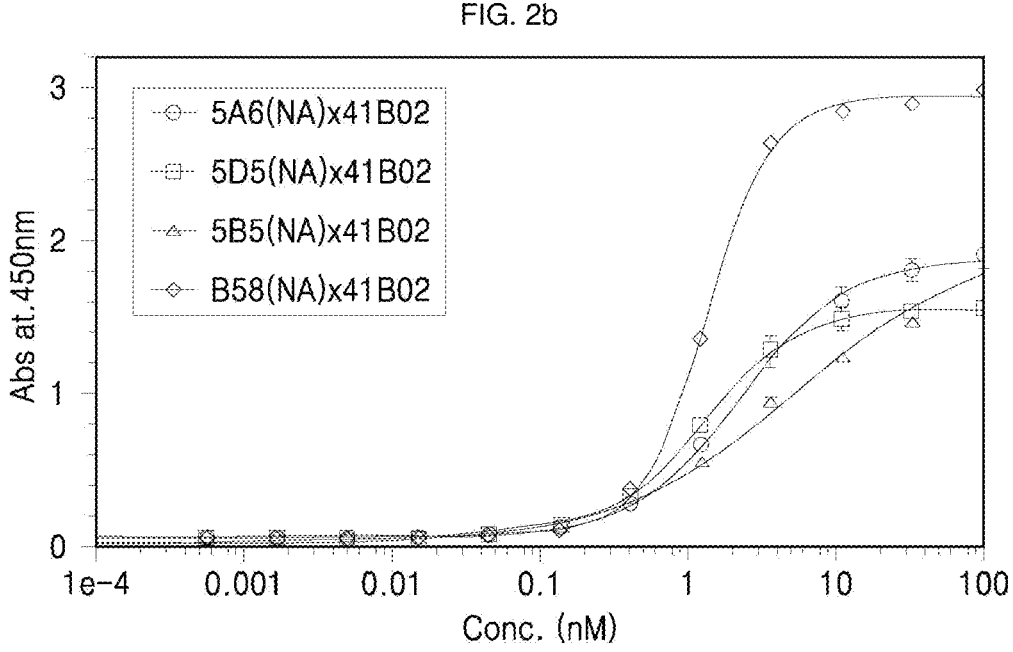
Figure 2C:
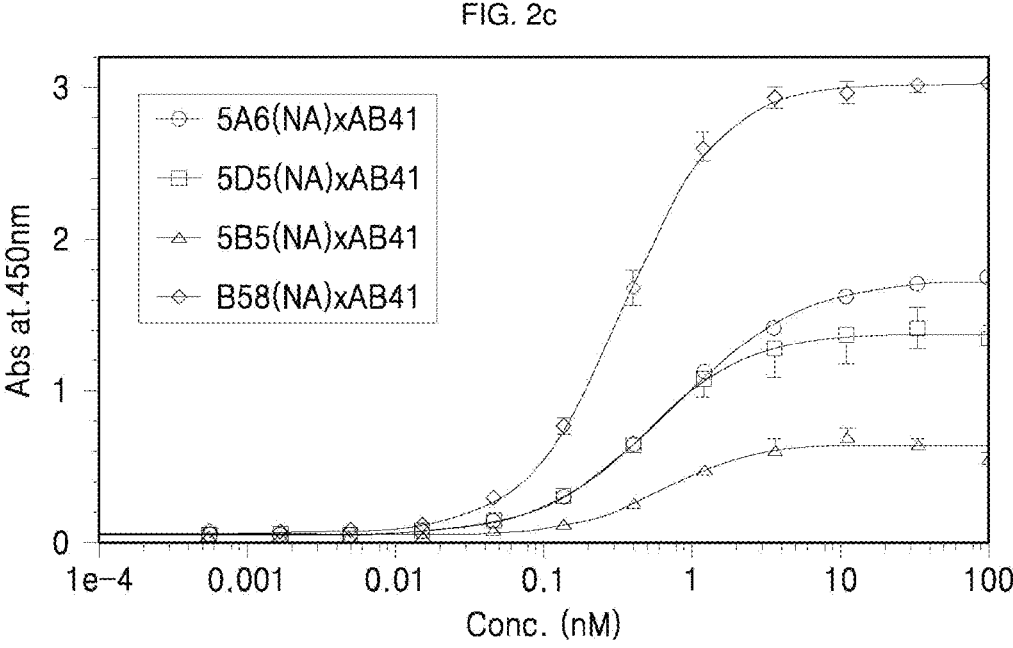

As shown in FIGS. 2a-2c, all the bispecific antibodies can bind to human BCMA and 4-1BB protein simultaneously with dose dependent manner. EC50 (nM) values are summarized in Table 13.

TABLE 13

| Antibody | EC50(nM) 4-1BB | | |
|---|---|---|---|
| BCMA | 41B01 | 41B02 | AB41 |
| 5A6(NA) | 0.359 | 2.22 | 0.763 |
| 5D5(NA) | 0.392 | 1.27 | 0.475 |
| 5B5(NA) | 0.683 | 5.57 | 0.636 |
| B58(NA) | 0.335 | 1.34 | 0.349 |

(2) Cell surface binding test by flow cytometry

Figure 2D:
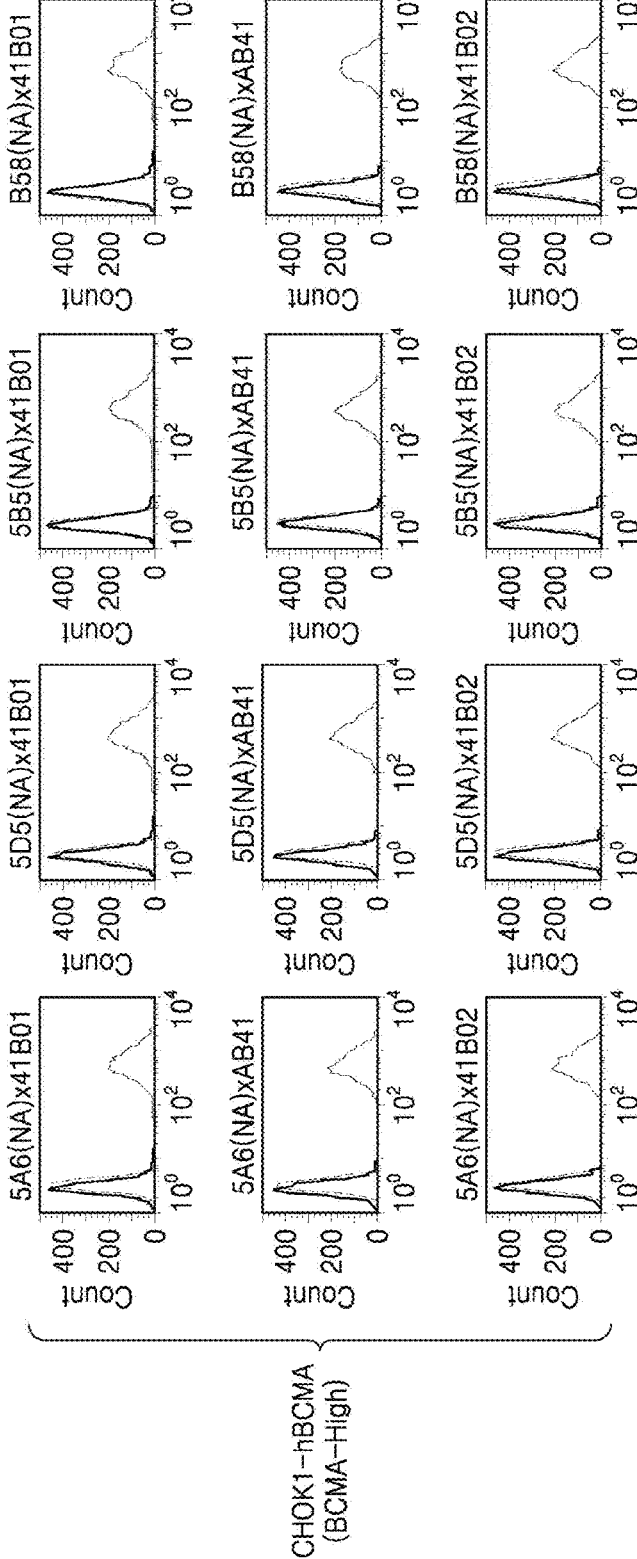
FIGS. 2d-2f are graphs showing a cell surface binding test using a Fluorescence-Activated Cell Sorting (FACS®) system.
Figure 2E:
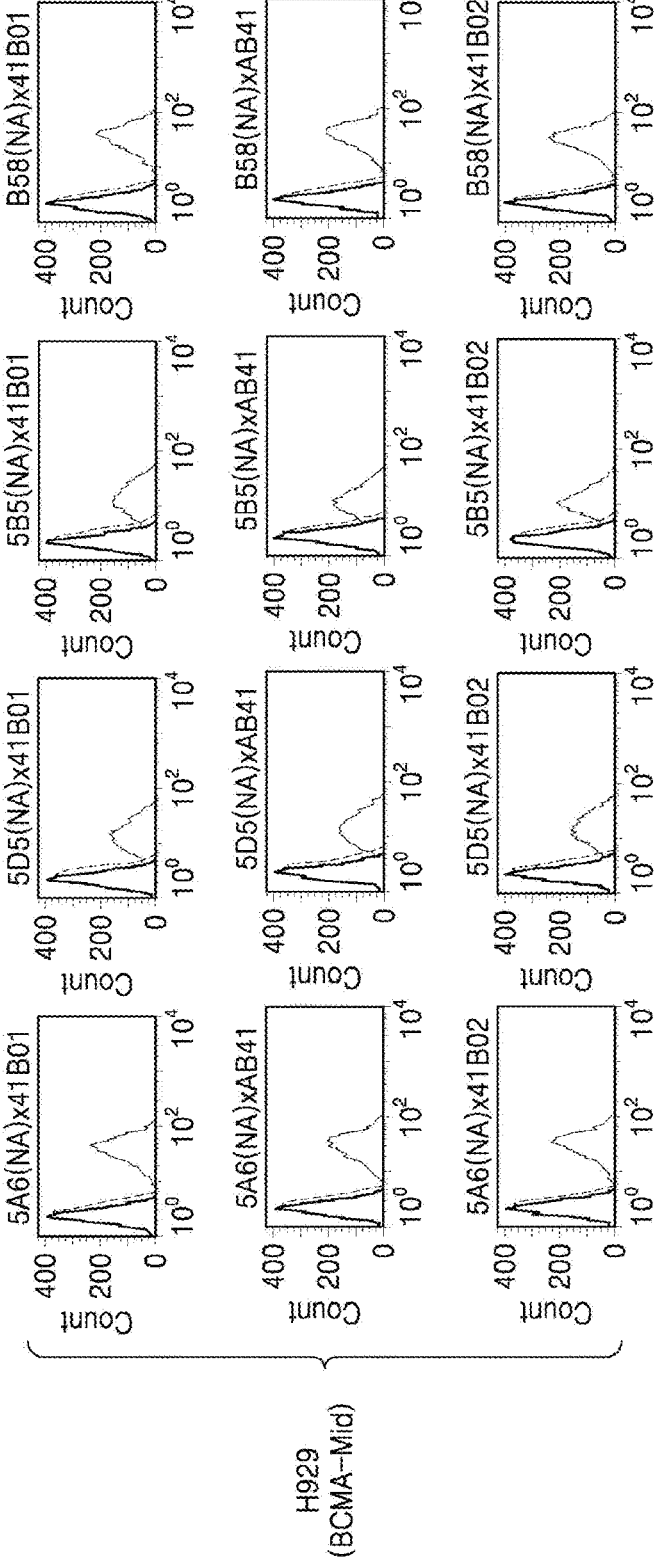
Figure 2F:
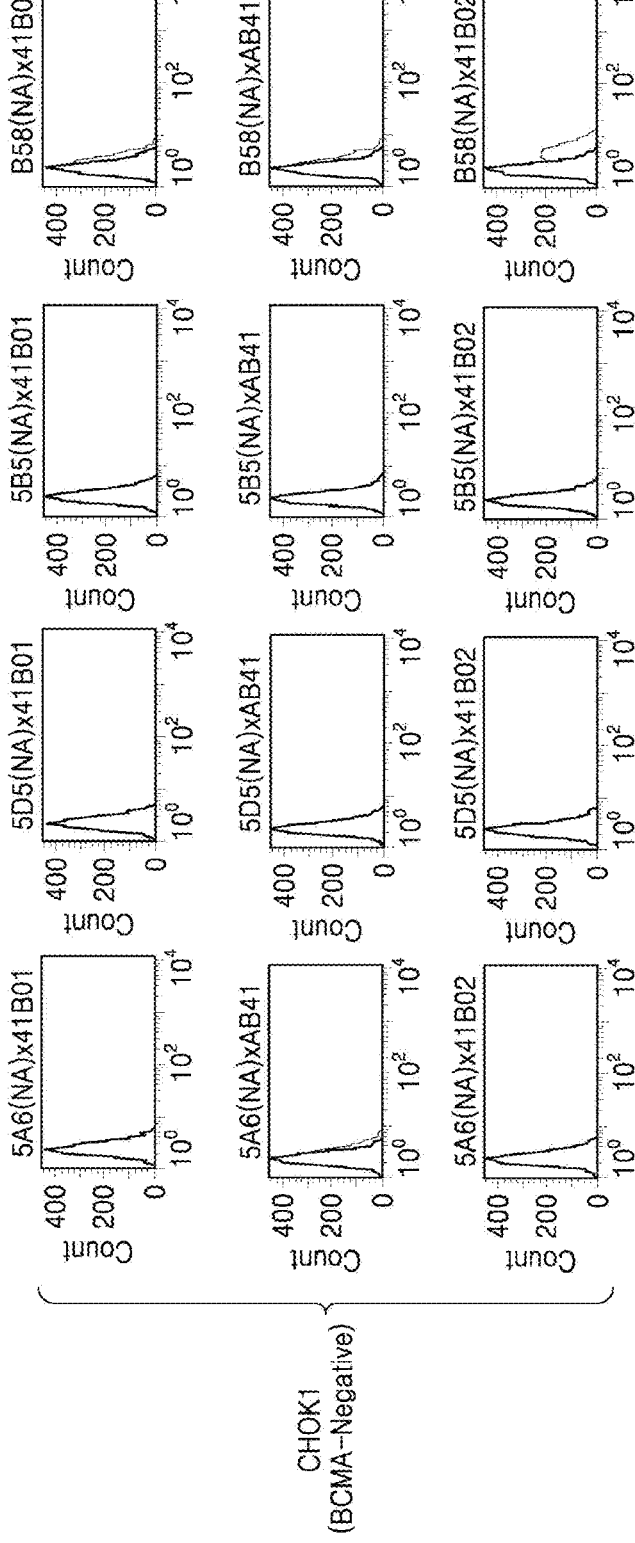

To evaluate the antigen binding property, the antibody candidates were analyzed for their bindings to BCMA expressed cells by FACS®. Briefly, CHOK1 expressing human BCMA (CHOK1-hBCMA) or H929 expressing endogenous BCMA cells were treated with the 100 nM of indicated antibodies at 4° C. for 1 hr. CHOK1 cells were used for BCMA-negative control. After washing by FACS® buffer (1% (w/v) BSA in PBS), cells were incubated with the FITC-anti-human IgG antibody at 4° C. for 1 hr and then subjected to FACS® analysis. As shown in FIGS. 2d-2f, the anti-BCMAx4-1BB antibodies bind to BCMA expressed CHOK1-hBCMA and H929 cell lines but not BCMA negative CHOK1. This result means that Anti-BCMA/anti-4-1BB Bispecific antibodies can bind to tumor targeting antigen (BCMA) specifically. The results of FIGS. 2d-2f are quantified and summarized in Table 14.

TABLE 14

| Antibodies | | Cell line | | |
|---|---|---|---|---|
| | | H929 | CHOK1 | CHOK1-hBCMA |
| Cell only | | 2.51 | 2.6 | 3.13 |
| $2^{nd}$ Ab control | | 3.24 | 2.66 | 3.65 |
| 5A6(NA) | x41B01 (1A10) | 43.8 | 3.06 | 652 |
| 5D5(NA) | | 17.9 | 2.74 | 579 |
| 5B5(NA) | | 17.6 | 3.37 | 493 |
| B58(NA) | | 45.8 | 3.45 | 662 |
| 5A6(NA) | xAB41 | 39.9 | 3.23 | 636 |
| 5D5(NA) | | 19.7 | 2.88 | 585 |
| 5B5(NA) | | 14.1 | 3.38 | 477 |
| B58(NA) | | 49.8 | 3.71 | 652 |
| 5A6(NA) | x41B02 (1A12) | 40.3 | 3.07 | 646 |
| 5D5(NA) | | 20.2 | 2.99 | 602 |
| 5B5(NA) | | 14.9 | 3.19 | 484 |
| B58(NA) | | 41.6 | 6.01 | 644 |

3-3. In Vitro 4-1BB Activation Test of Anti-BCMA/Anti-4-1BB Bispecific Antibodies (4-1BB Reporter Bioassay)

In this assay, GloResponse™ NF$\kappa$B-luc2/4-1BB Jurkat cell line, genetically modified to stably express human 4-1BB and luciferase downstream of a response element, was used as effector cell and cancer cells expressing or not expressing BCMA were used as target cells. In brief, plate CHOK1-hBCMA (BCMA positive, $2.5 \times 10^1$n), or CHOK1 (BCMA negative, $2.5 \times 10^1$) in a white 96-well assay plate in 100 $\mu$l culture medium each. Culture overnight in 37° C. with 5% $CO_2$ humidified incubator. After overnight culture, remove 100 $\mu$l of culture medium and dispense 25 A2 of assay medium (RPM11640 containing 1% (v/v) FBS) to pre-plated target cells. In case of suspension cells, plate H929 (BCMA positive, $2.5 \times 10^1$) or Jurkat (BCMA negative, $2.5 \times 10^5$) in a white 96-well assay plate in 25 $\mu$l of assay medium. 25 $\mu$l of each bispecific antibody (starting from 50 nM diluted for 5-fold or 200 nM diluted for 4-fold) were added to the plate. Harvest GLORESPONSE™ NF$\kappa$B-luc2/4-1BB Jurkat cell line and resuspend with assay medium. Dispense 25 $\mu$l of GLORESPONSE™ NF$\kappa$B-luc2/4-1BB Jurkat cell line to make $2.5 \times 10^4$ cells per well to plate. Culture 6 hrs in 37° C. with 5% $CO_2$ humidified incubator. During incubation time reconstitute BIO-GLO™ reagent according to the manufacturer's instruction. After 6 hrs incubation, add 75 per well of BIO-GLO™ Reagent to the assay plate. Wait 5 minutes and measure luminescence using microplate reader. Four-parameter logistic curve was evaluated by using GraphPad software. The experimental results using CHOK1-hBCMA, CHOK1, H929 and Jurkat cells are shown in FIGS. 3a-3d, respectively.

Figure 3A:
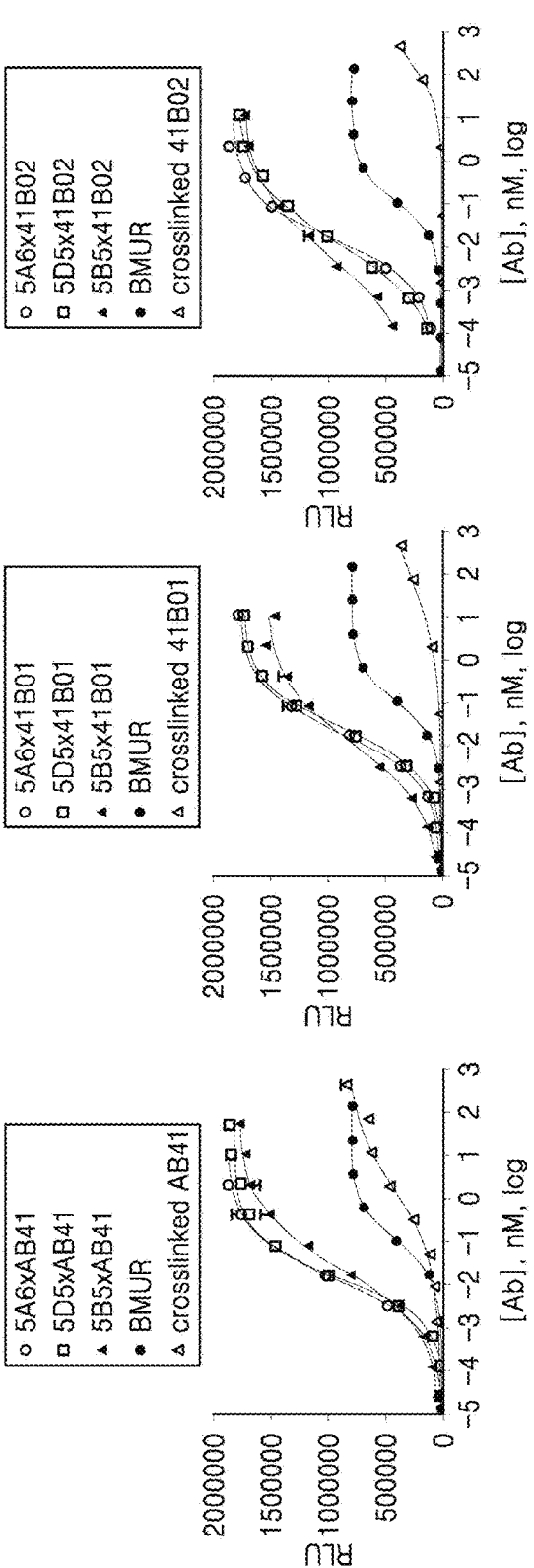
FIGS. 3a, 3b, 3c and 3d are graphs showing results of a 4-1BB reporter bioassay.
Figure 3B:
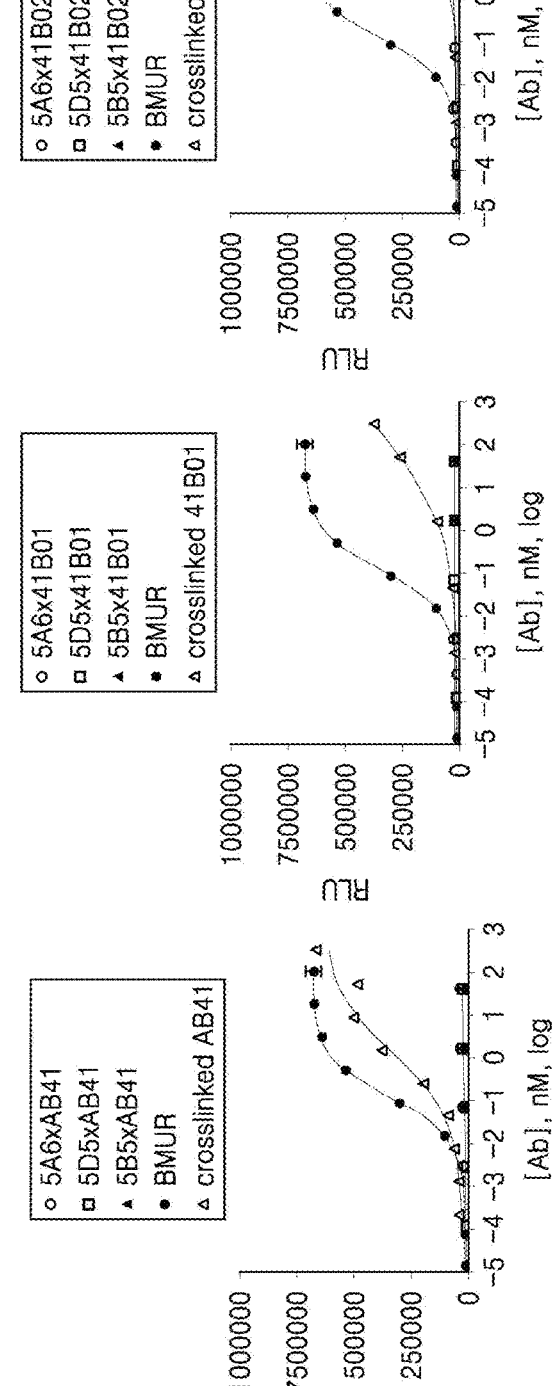
Figure 3C:
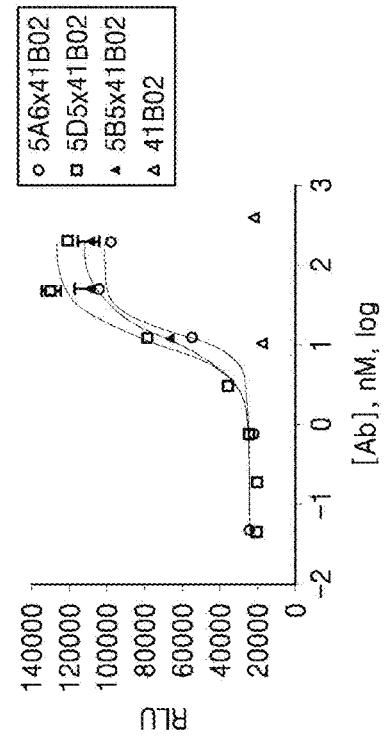
Figure 3C:
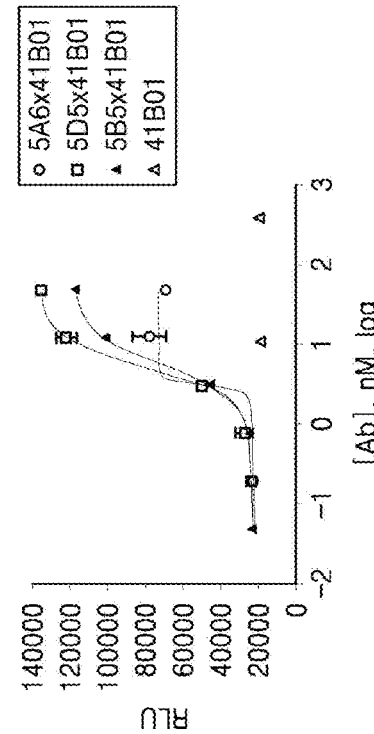
Figure 3D:
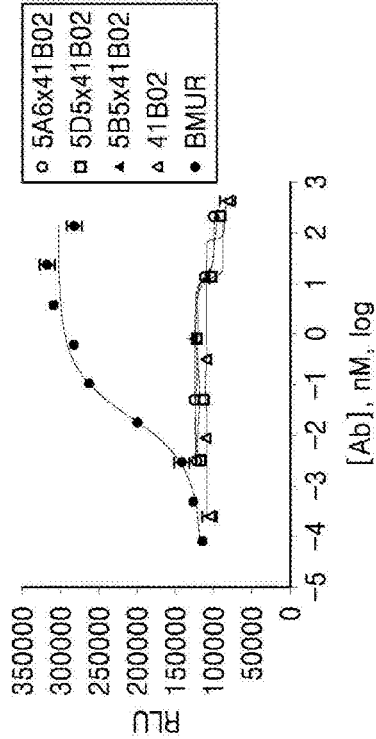
Figure 3D:
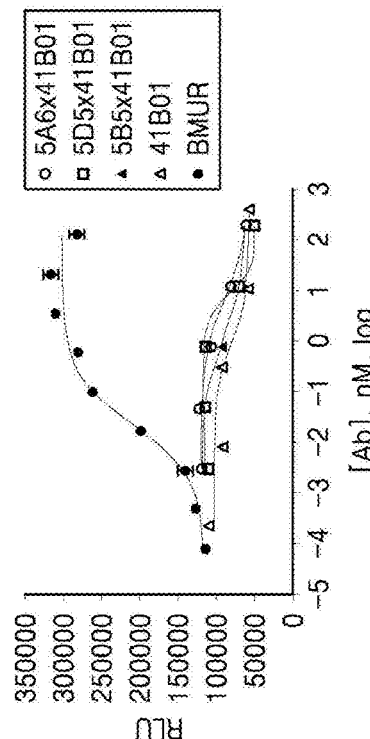

As shown in FIGS. 3a-3d, the BCMAx4-1BB bispecific antibodies tested showed stronger 4-1BB signal activation in the presence of tumor antigen (BCMA), compared to anti 4-1 BB monoclonal antibodies alone or cross-linked 4-11BB applied. And also BMUR which is agonistic anti 4-1BB monoclonal antibody (Reference antibody) had an in vitro 4-1BB activation effect in the absence of BCMA (FIGS. 3b and 3d).

This means that anti-BCMA/anti-4-1BB antibodies can only act specifically in the presence of BCMA-expressing cancer cells but not agonistic anti 4-1BB antibody. The results of FIGS. 3a-3d are quantified and summarized in Tables 15 and 16 (Table 15: CHOK1-hBCMA (EC50, nM), Table 16: H929 (EC50, nM)).

TABLE 15

|  | xAB41 | x41B01 | x41B02 | BMUR |
|---|---|---|---|---|
| 5A6(NA) | 0.0397 | 0.0616 | 0.0413 | 0.1025 |
| 5D5(NA) | 0.0426 | 0.0691 | 0.0314 | |
| 5B5(NA) | 0.0741 | 0.0316 | 0.003 | |

TABLE 16

|  | x41B01 | x41B02 | BMUR |
|---|---|---|---|
| 5A6(NA) | 3.164 | 14.34 | 0.069 |
| 5D5(NA) | 5.354 | 10.92 | |
| 5B5(NA) | 5.756 | 12.11 | |

3-4. In Vitro 4-11BB Activation Test of Anti-BCMA/Anti-4-1BB Bispecific Antibodies (Human PBMC Based Test)

Human PBMCs were co-cultured with CHOK1 cell line (not expressing human BCMA) or genetically modified CHOK1-hBCMA (stably expressing human BCMA) in the presence of anti-human CD3 antibody and antibodies to be tested. In brief, PBMCs were plated with $3 \times 10^1$ cells per well and either CHOK1 or CHOK1-hBCMA were co-plated with $1 \times 10^4$ cells per well. Bispecific antibodies (starting from 20 nM diluted for 4-fold) and monoclonal antibodies (starting from 26.67 nM diluted for 4-fold) were added to the plate wells. After culture, the concentration of secreted IFN-gamma in supernatant was measured by Human IFN-gamma QUANTIKINE® Kit (R&D system, SIF50).

Figure 4A:
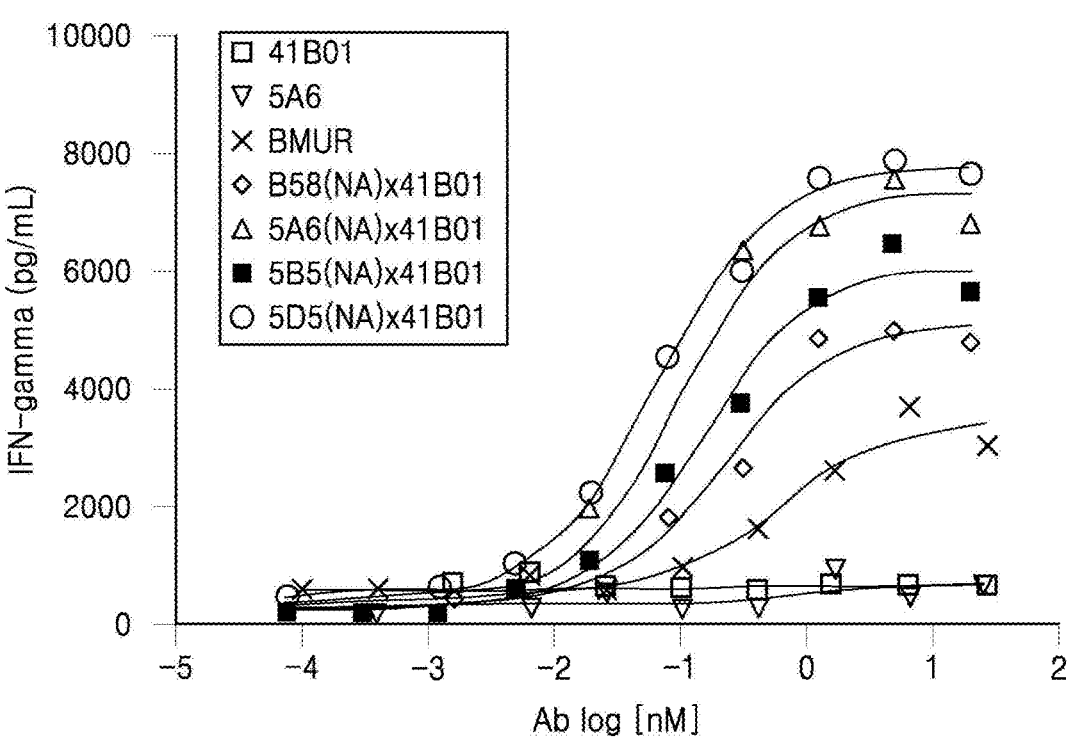
FIGS. 4a, 4b and 4c are graphs showing results of a PBMC-based study.
Figure 4B:
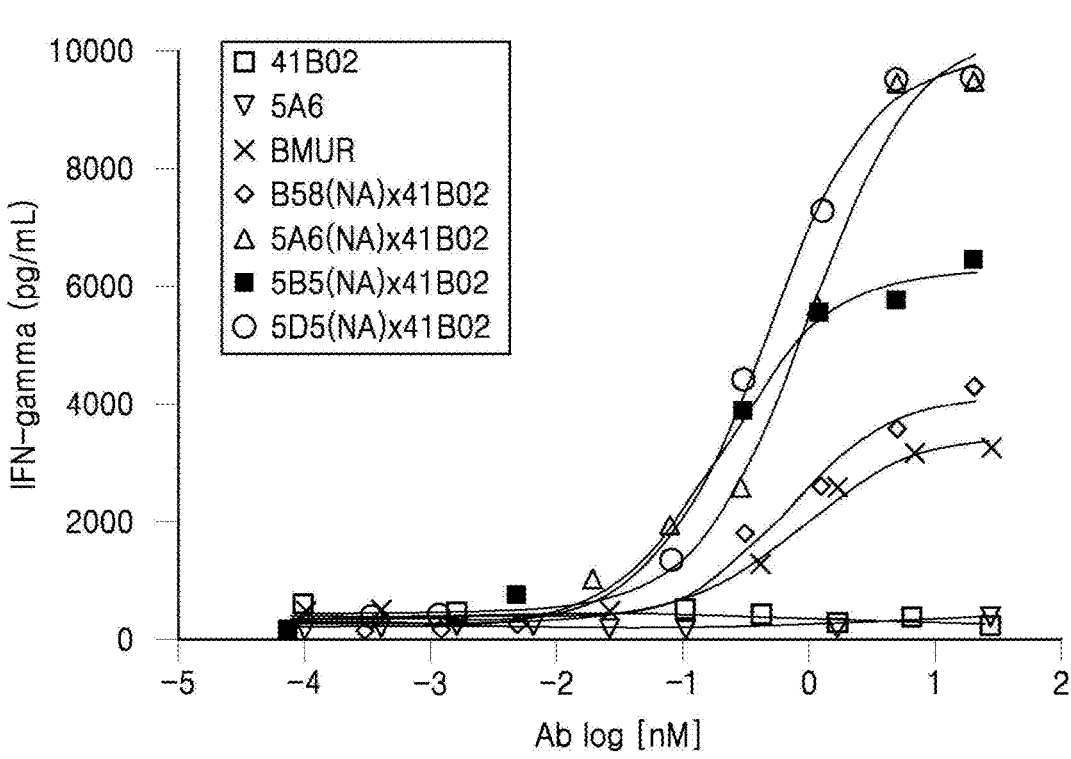
Figure 4C:
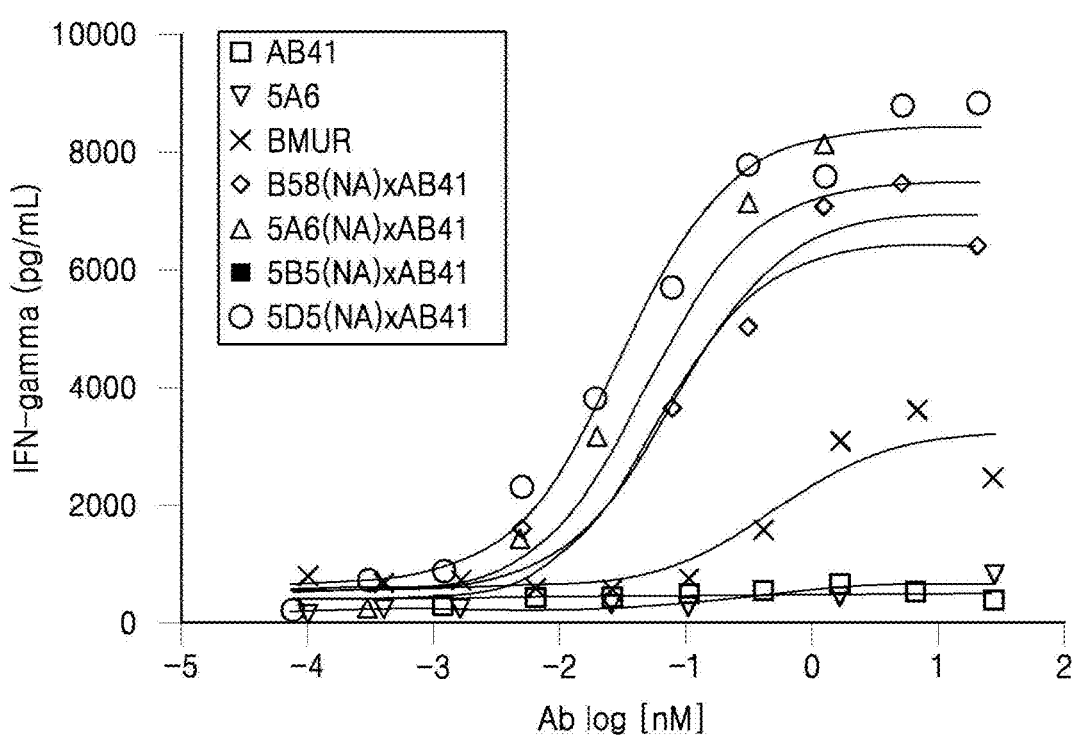

As shown in FIGS. 4a-4c anti-BCMA/anti-4-1BB antibodies induced more cytokine release than monoclonal antibodies or BMUR (Agonistic anti-4-1BB monoclonal antibody).

3-5. Target Protein Binding Activity Comparison (Wilde Type Vs Mutants)

In order to stabilize anti-BCMA/anti-4-1BB bispecific antibodies, one or more than one point mutations in amino acid sequences was introduced in the Heavy chain or Light chain CDR of antibodies as shown Table 4. To evaluate the antigen binding activity, the antibody candidates (Wild type clone and Mutant clones) were subjected to DACE (Dual Antigen Captured ELISA) test as performed in Example 3-2(1). The obtained results are shown in FIGS. 5a-5b.

Figure 5A:
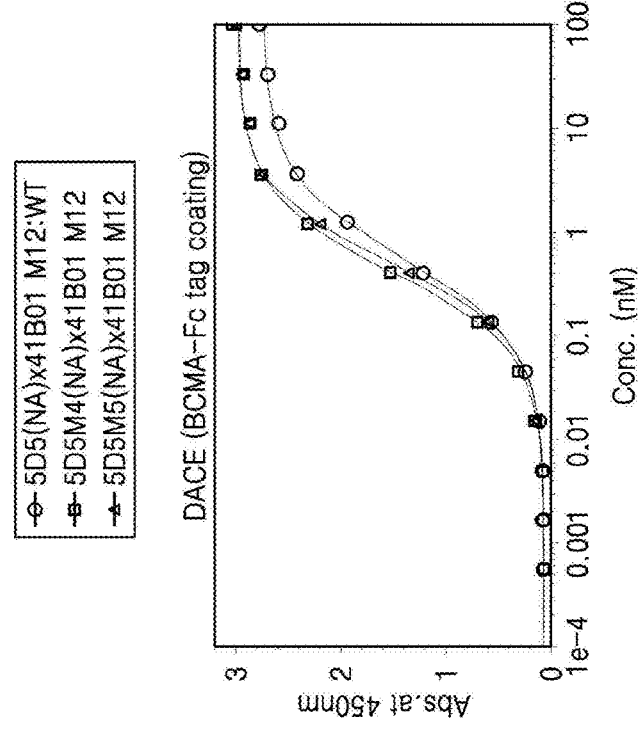
FIG. 5a is graphs showing results of a target protein binding test using DACE (5D5 WT and 5D5 Mutants)
Figure 5A:
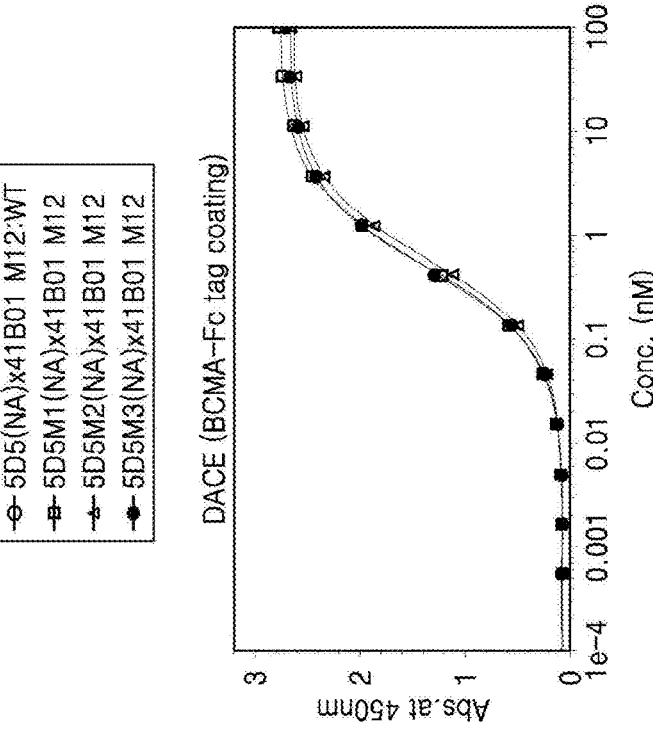
Figure 5B:
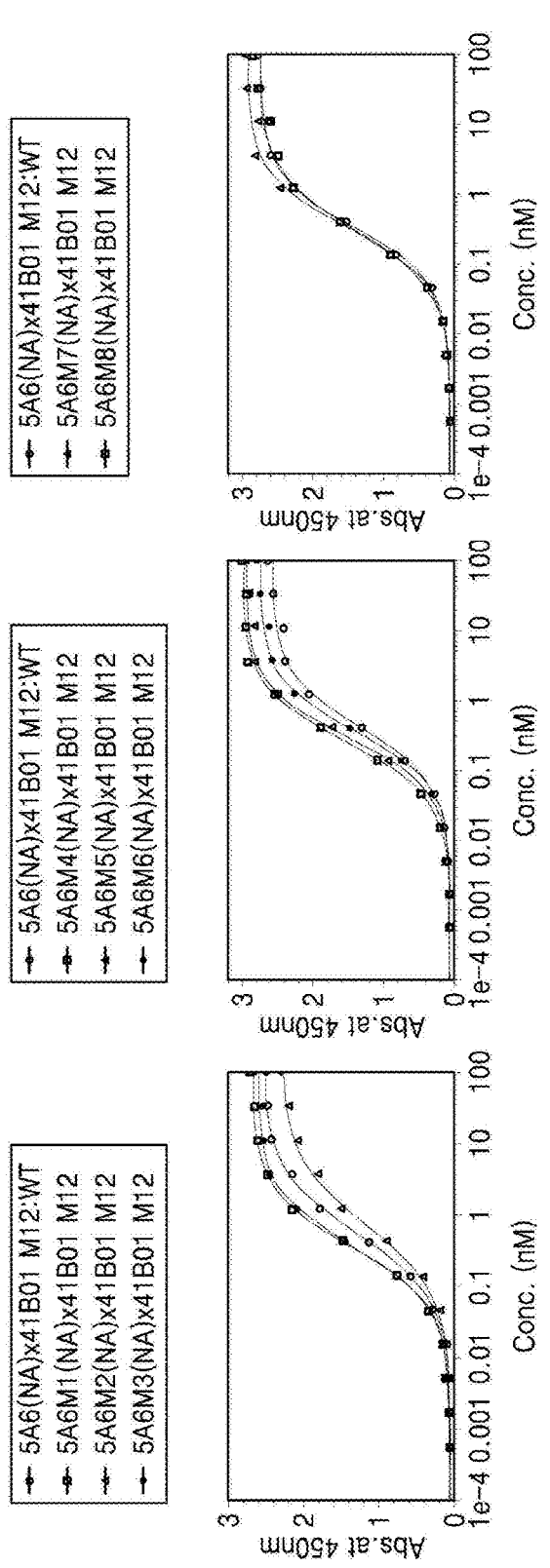
FIG. 5b is graphs showing results of a target protein binding test using DACE (5A6 WT and 5A6 Mutants)
Figure 5C:
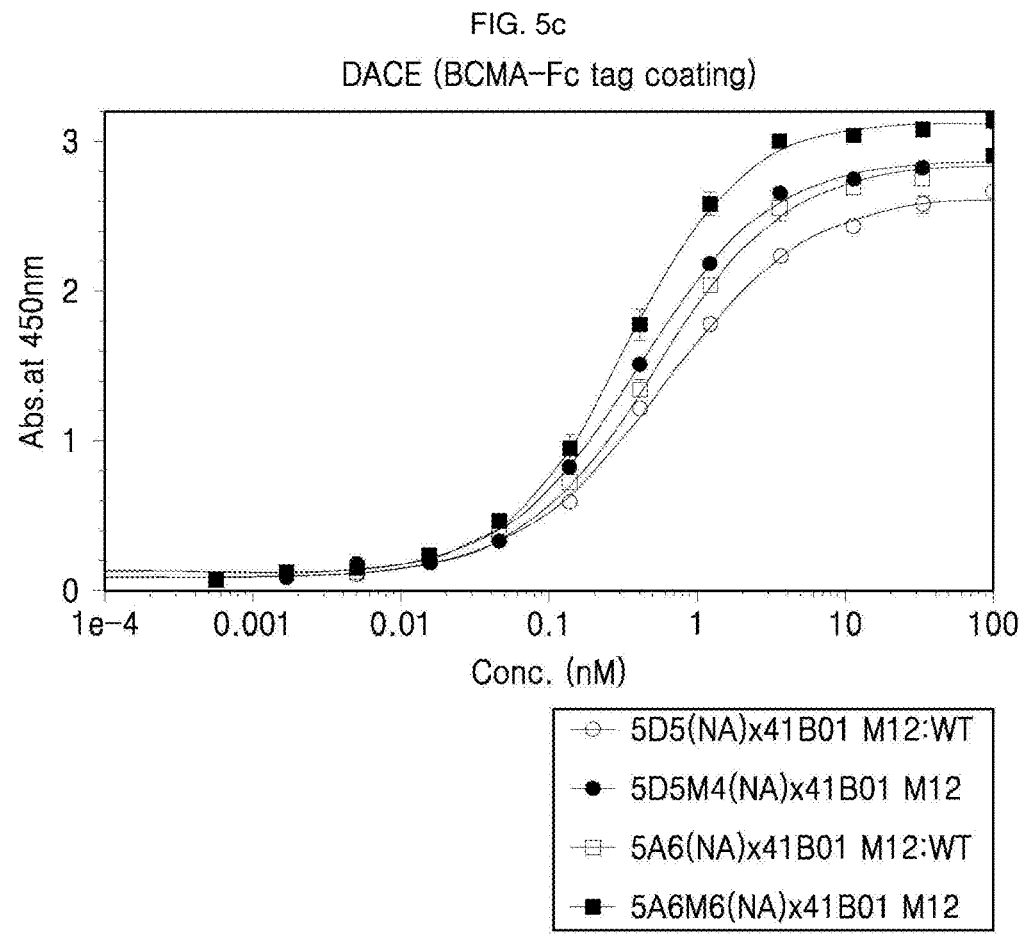
Figure 5D:
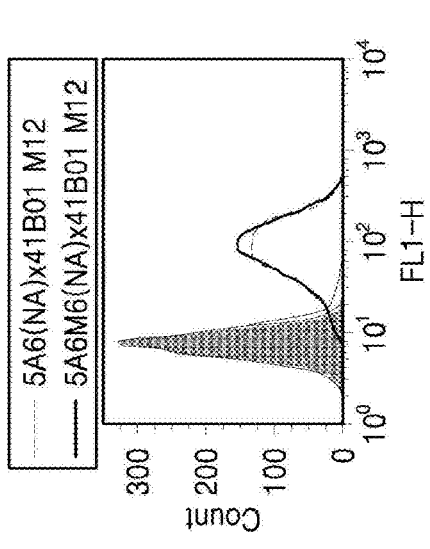
FIG. 5d is graphs showing a cell surface binding test using a FACS® system (WT and Mutants)
Figure 5D:
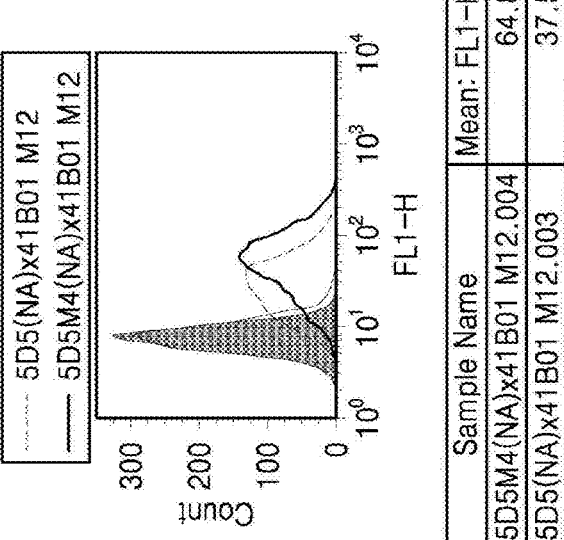

As shown in FIG. 5a-5b, all the bispecific antibodies can bind to human BCMA and 4-1BB protein simultaneously with dose dependent manner. And several mutants were found to improve target protein binding. Among the mutants, 5D5M4(NA)X41B01 M12 and 5A6M6(NA) X41B01 M12 showed superior antigen binding activity compared with Wild type clone (FIG. 5c). To evaluate the native antigen binding property, 5D5M4(NA)X41B01 M12 and 5A6M6(NA)X41B01 M12 were analyzed for its binding to mammalian expressed BCMA by FACS® as performed in Example 2-2(2). As shown in FIG. 5d, 5D5M4(NA)X41B01 M12 and 5A6M6(NA)X41B01 M12 showed increased native antigen binding activity compared with Wild type. The results of the protein binding test and the cell binding test are quantified and summarized in Tables 17 and 18 (Table 17: Protein binding (EC50, nM)).

TABLE 17

|  | Antibody | EC50 (nM) |
|---|---|---|
| FIG. 5a (left) | 5D5(NA)x41B01 M12:WT | 0.496 |
| | 5D5M1(NA)x41B01 M12 | 0.542 |
| | 5D5M2(NA)x41B01 M12 | 0.580 |
| | 5D5M3(NA)x41B01 M12 | 0.468 |
| FIG. 5a (right) | 5D5(NA)x41B01 M12:WT | 0.547 |
| | 5D5M4(NA)x41B01 M12 | 0.418 |
| | 5D5M5(NA)x41B01 M12 | 0.507 |
| FIG. 5b (left) | 5A6(NA)x41B01 M12:WT | 0.545 |
| | 5A6M1(NA)x41B01 M12 | 0.355 |
| | 5A6M2(NA)x41B01 M12 | 0.698 |
| | 5A6M3(NA)x41B01 M12 | 0.356 |
| FIG. 5b (middle) | 5A6(NA)x41B01 M12:WT | 0.397 |
| | 5A6M4(NA)x41B01 M12 | 0.356 |
| | 5A6M5(NA)x41B01 M12 | 0.249 |
| | 5A6M6(NA)x41B01 M12 | 0.291 |
| FIG. 5b (right) | 5A6(NA)x41B01 M12:WT | 0.334 |
| | 5A6M7(NA)x41B01 M12 | 0.325 |
| | 5A6M8(NA)x41B01 M12 | 0.304 |

TABLE 18

| Antibody | MFI | MFI of mutant/MFI of WI × 100 |
|---|---|---|
| 5D5M4(NA)x41B01 M12 | 64.8 | 172.8% |
| 5A6M6(NA)x41B01 M12 | 102 | 101.0% |

3-6. Binding Affinity of Mutant Bispecific Antibodies to Target Protein BCMA and 4-1BB (SPR)

In the SPR experiment, the anti-BCMA/anti-4-1BB bispecific antibodies obtained in Example 3-5 were individually captured on flow-cells 2, 3 and 4, keeping the flow-cell 1 as reference, on a Protein A Chip on which an anti-BCMA/ anti-4-1BB Bispecific antibody (5D5M4(NA)X41B01 M12 or 5A6M6(NA)X41B01 M12) had been immobilized by amine coupling. Recombinant Human BCMA or Human 4-1BB protein was flowed across the chip at concentration range from 100 nM to 6.25 nM for human BCMA or 250 nM to 15.625 nM for human 4-1BB and 0.78 nM at 30 μl/min for 300 seconds, followed by a dissociation phase of 400 seconds. Regeneration was performed with 10 mM Glycine-HCl (pH 2.0). The obtained results are shown in following Tables 19 and 20. As shown in Tables 19 and 20, 5D5M4 (NA)X41B01 M12 and 5A6M6(NA)X41B01 M12 showed high affinity against BCMA and 4-1BB (Table 19: Affinity measurement result for 5D5M4(NA)X41B01 M12, Table 20: Affinity measurement result for 5A6M6(NA)X41B01 M12).

TABLE 19

| Target | Ka ($\times 10^5$, 1/Ms) | Kd ($\times 10^{-2}$, 1/s) | $K_D$ ($\times 10^{-8}$, M) | $R_{max}$ (RU, target = 12.5 RU) |
|---|---|---|---|---|
| hBCMA | 40.69 | 6.503 | 1.602 | 13.18 |
| h-BB | 2.361 | 9.461 | 4.009 | 53.78 |

TABLE 20

| Target | Ka ($\times 10^5$, 1/Ms) | Kd ($\times 10^{-2}$, 1/s) | $K_D$ ($\times 10^{-8}$, M) | $R_{max}$ (RU, target = 12.5 RU) |
| --- | --- | --- | --- | --- |
| hBCMA | 5.272 | 1.186 | 2.257 | 13.42 |
| h4-1BB | 2.379 | 9.732 | 4.102 | 52.61 |

3-7. In Vitro 4-1BB Activation Test for Mutant Bispecific Antibodies

The antibody candidates were analyzed for their in vitro 4-1BB activity by using Promega kit system as in Example 2-3.

Figure 6A:
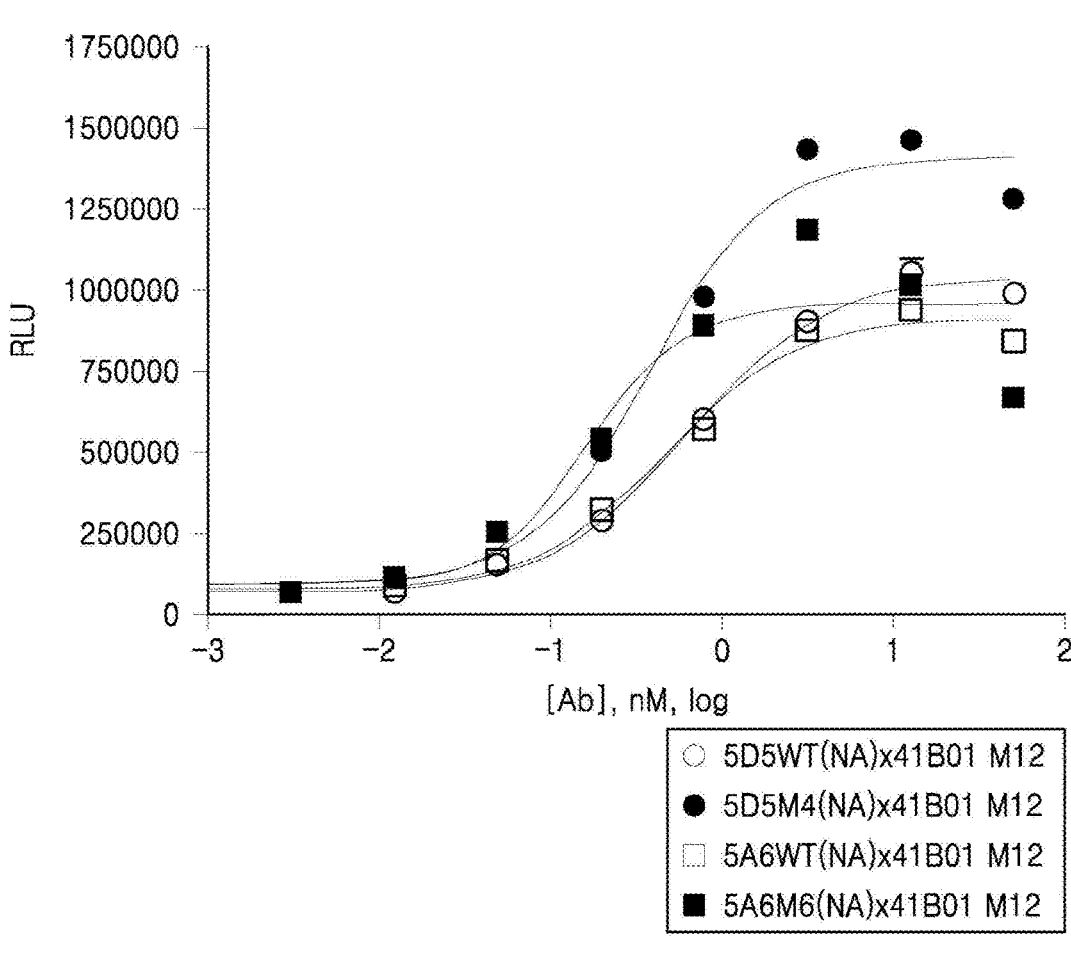
FIGS. 6a, 6b and 6c are graphs showing results of an in vitro 4-1BB activation test.
Figure 6B:
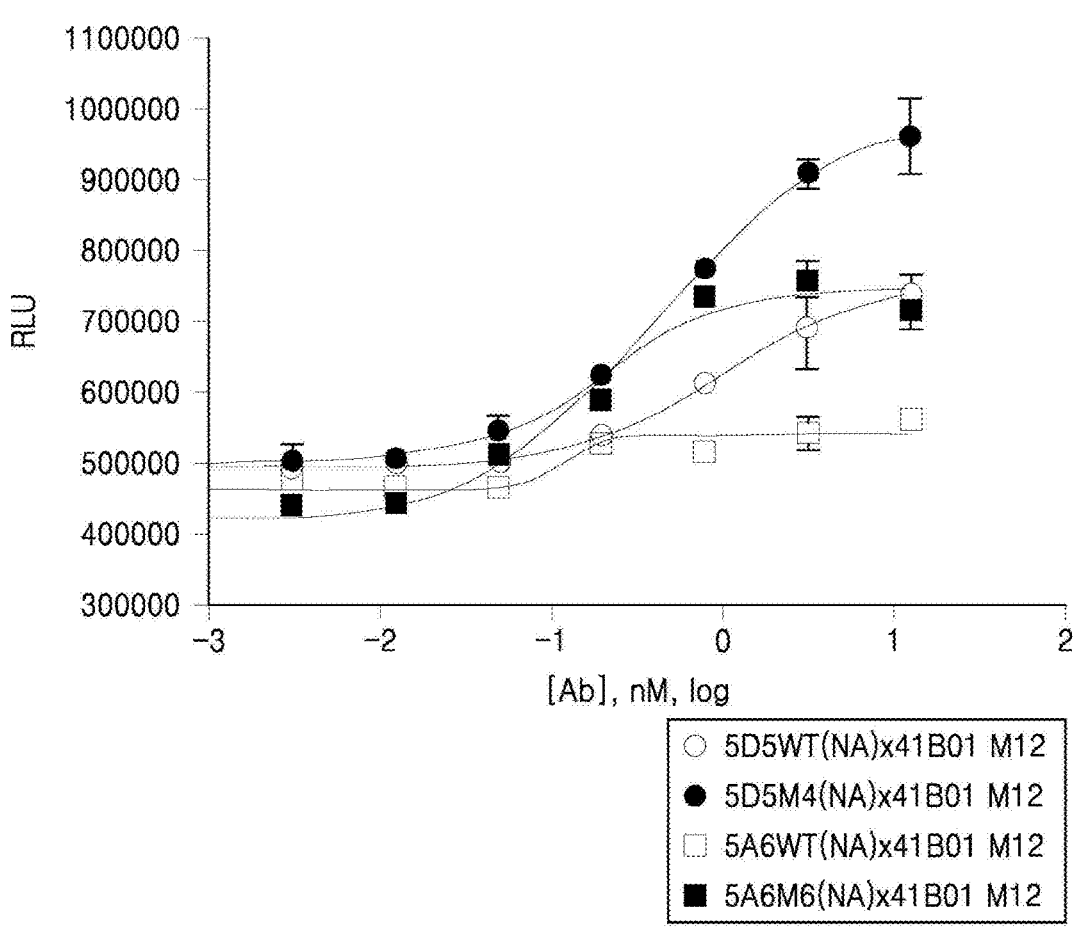
Figure 6C:
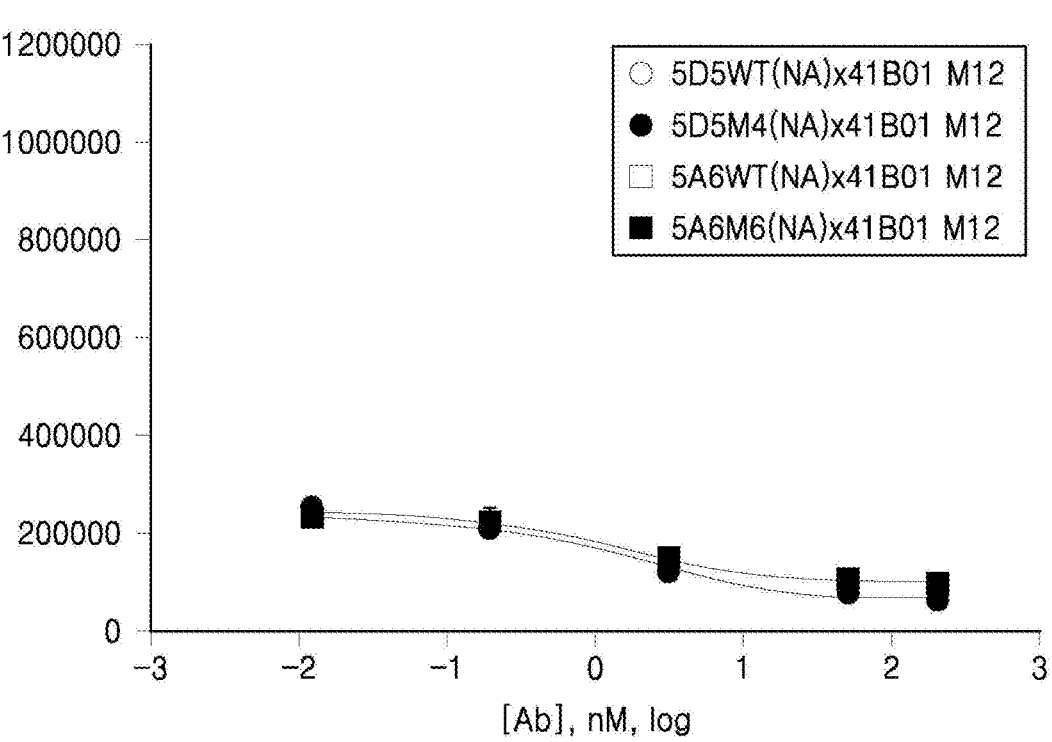

As shown in FIGS. 6a-6c, mutant format of Anti-BCMA/anti-4-1BB Bispecific antibodies showed improved potency compared to the wild type format in BCMA positive cancer cells while all clones did not activate 4-1BB signaling in BCMA negative cancer cells (Jurkat)(Table 21: In vitro 4-1BB activation result (EC50, nM)). Therefore, 5D5M4(NA)X41B01 M12 and 5A6M6(NA)X41B01 M12 showed improved target mediated 4-1BB activation.

TABLE 21

| Antibody Name | H929 | MM1S |
| --- | --- | --- |
| 5D5WT(NA)x41B01 M12 | 0.629 | 2.66 |
| 5D5M4(NA)x41B01 M12 | 0.377 | 2.41 |
| 5A6WT(NA)x41B01 M12 | 0.459 | 2.26 |
| 5A6M6(NA)x41B01 M12 | 0.165 | 1.98 |

3-8. Monkey Cross Reactivity Test for Mutant Bispecific Antibodies

Figure 7:
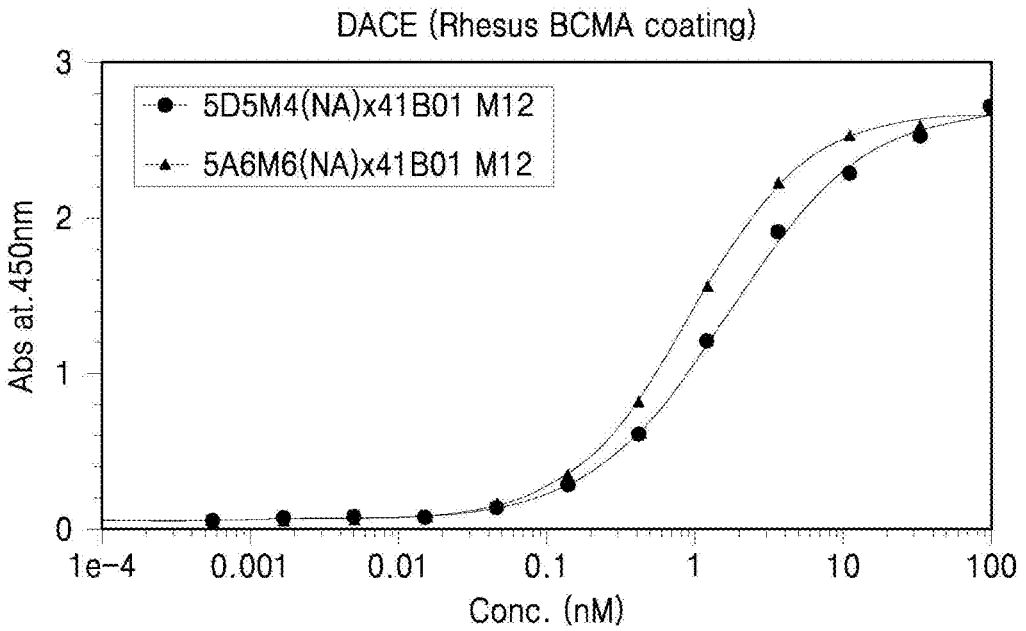
FIG. 7 is a graph showing results of a monkey cross reactivity test by DACE.

To evaluate the cross reactivity, the antibody candidates (5D5M4(NA)X41B01 M12 and 5A6M6(NA)X41B01 M12) were subjected to ELISA test. Briefly, microtiter plates were coated with Rhesus BCMA-Fc protein (50 ng/well) at 4° C. overnight, then blocked with 200 µl/well PBSB (1% (w/v) BSA in PBS). Three-fold dilutions of 5D5M4(NA)X41B01 M12 and 5A6M6(NA)X41B01 M12 starting from 100 nM were added to each well and incubated at 37° C. for 1 hours. The plates were washed with PBST (0.05% (v/v) TWEEN® 20 in PBS) and then incubate for 1 hours at 37° C. with Rhesus 4-1BB-His protein (80 ng/well). The plates were washed with PBST (0.05% (v/v) TWEEN® 20 in PBS) and then incubated with HRP (Horse Radish Peroxidase) conjugated Anti-his antibody for 1 hr at 37° C. After washing, the plates were developed with TMB substrate and analyzed by spectrophotometer at 450-630 nm. As shown in FIG. 7, 5D5M4(NA)X41B01 M12 and 5A6M6(NA)X41B01 M12 bind to Rhesus BCMA and 4-1BB simultaneously with dose dependent manner (Table 22: Protein binding (EC50, nM)).

TABLE 22

| Antibody | EC50 (nM) |
| --- | --- |
| 5D5M4(NA)x41B01 M12 | 0.926 |
| 5A6M6(NA)x41B01 M12 | 1.66 |

3-9. Tumor Growth Inhibition by Mutant Bispecific Antibodies in Humanized NOG Mice Bearing H929

Figure 8A:
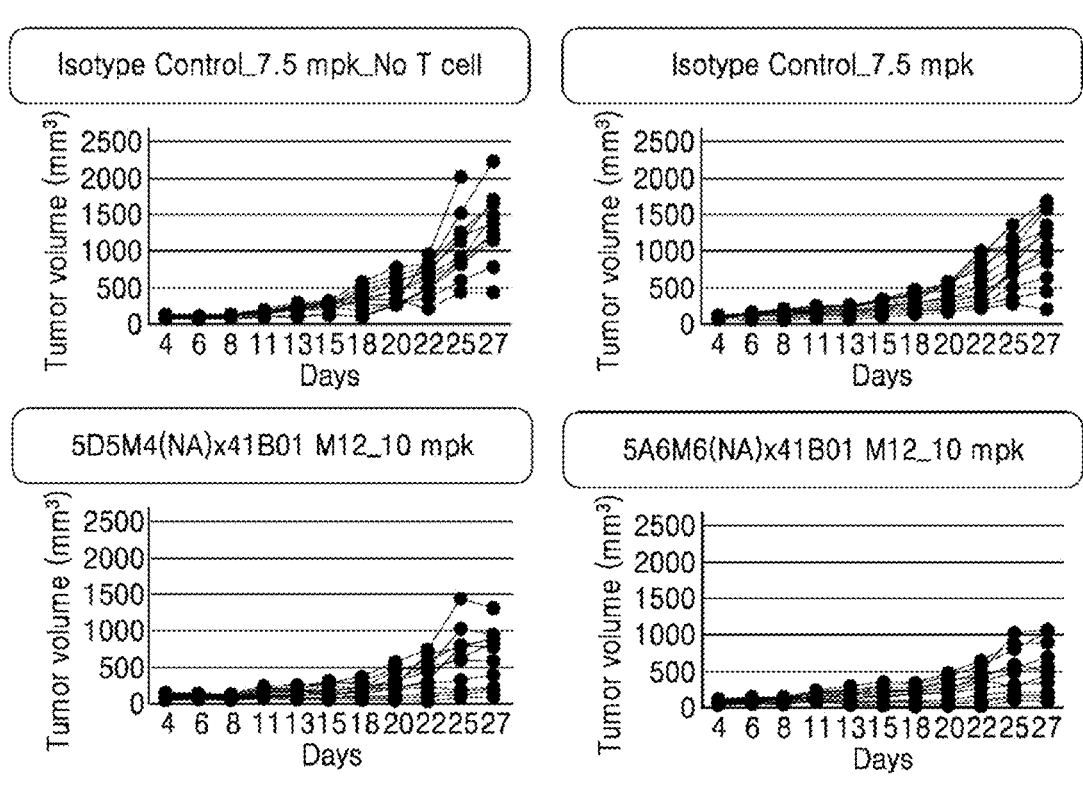
FIGS. 8a, 8b and 8c are graphs showing tumor growth inhibition by a BCMAx4-1 BB bispecific antibody in humanized NOG Mice bearing H929.
Figure 8B:
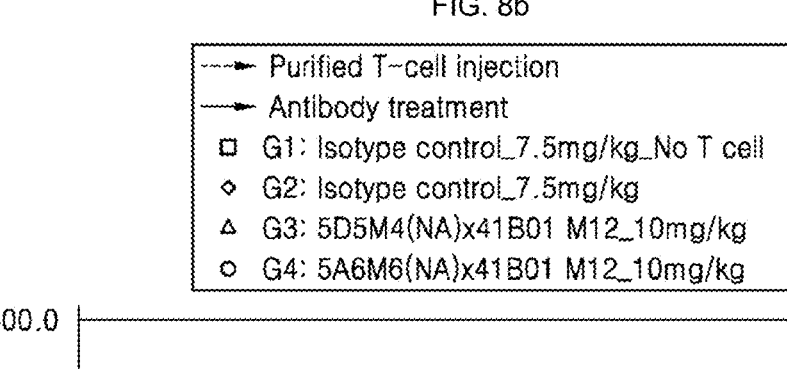
Figure 8B:
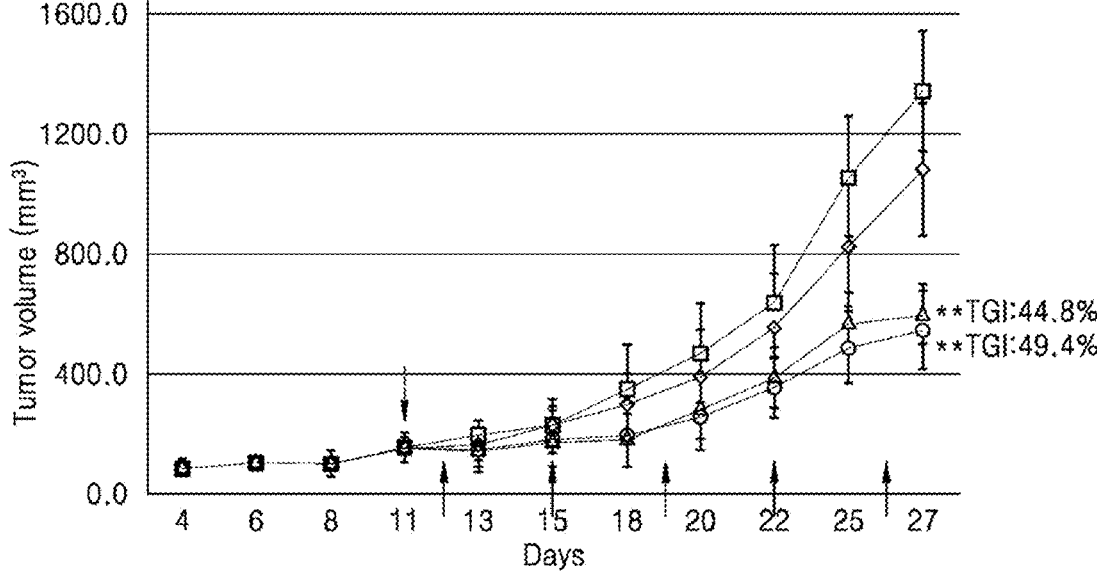
Figure 8C:
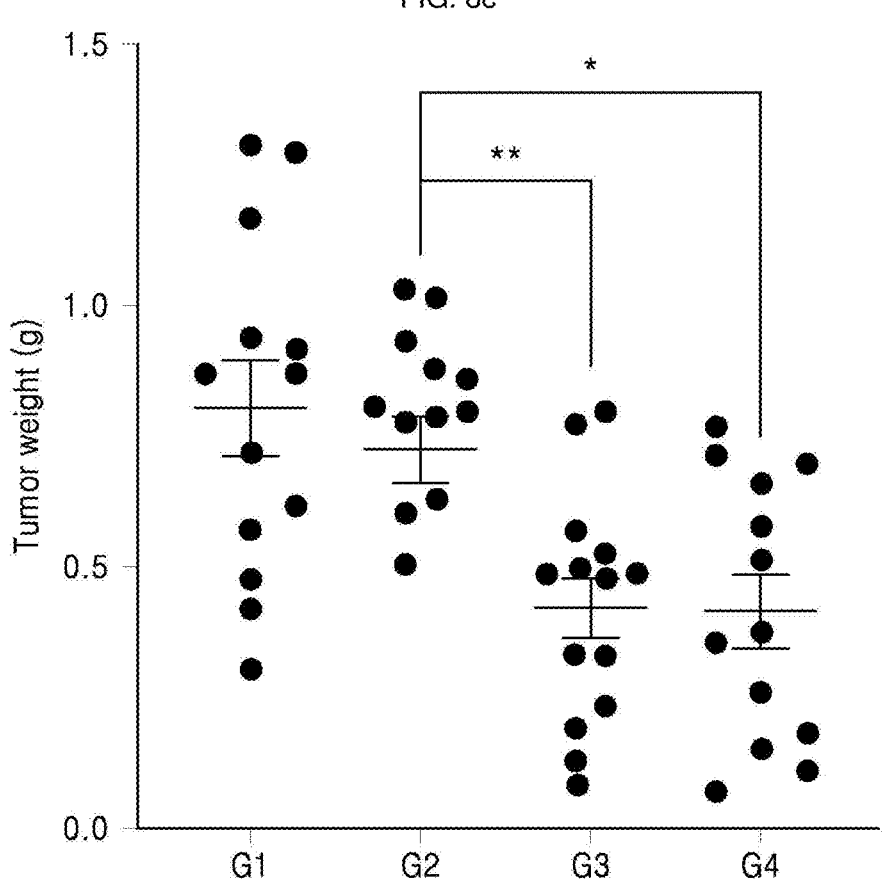

The anti-tumor effect of the anti-BCMA/anti-4-1BB antibody was tested in Humanized NOG mice which were injected with H929 cells. In brief, H929 cell were injected by Subcutaneous injection of NCI-H929 cells ($5 \times 10^6$) into the right flank of 74 non-irradiated female animals. On Day 11, Purified T-Cells ($10 \times 10^6$) from three donors were injected Intraperitoneal injection into mice. When tumors reached a mean volume of 154 mm³ (on day 12), Animals were randomized four groups of 14 mice each. Mouse were intravenously administered Q3D for five times (five time injection of the antibody every three days) with following antibodies: Human IgG type control (7.5 mg/kg_No T-cell injected: Isotype Control_7.5 mpk_No T-ell), Human IgG type control (7.5 mg/kg: Isotype Control_7.5 mpk), Anti-BCMA/anti-4-1BB Bispecific antibody (5D5M4(NA)X41B01 M12, 10 mg/kg) and Anti-BCMA/anti-4-1BB Bispecific antibody (5A6M6(NA)X41B01 M12, 10 mg/kg). Tumor volumes were monitored by caliper measurement twice per week for the duration of the experiment, and the obtained results are shown in FIG. 8a-8c. As shown FIGS. 8a and 8b, 5D5M4(NA)X41B01 M12 and 5A6M6(NA)X41B01 M12 showed significant anti-tumor effect. Tumor growth inhibition rate (TGI %) was 44.8% for 5D5M4(NA)X41B01 M12, 49.4% for 5A6M6(NA)X41B01 M12. Therefore, Efficacy of two bispecific antibodies was similar.

3-10. Analysis of Tumor-Infiltrating Lymphocytes (TIL)

Figure 9A:
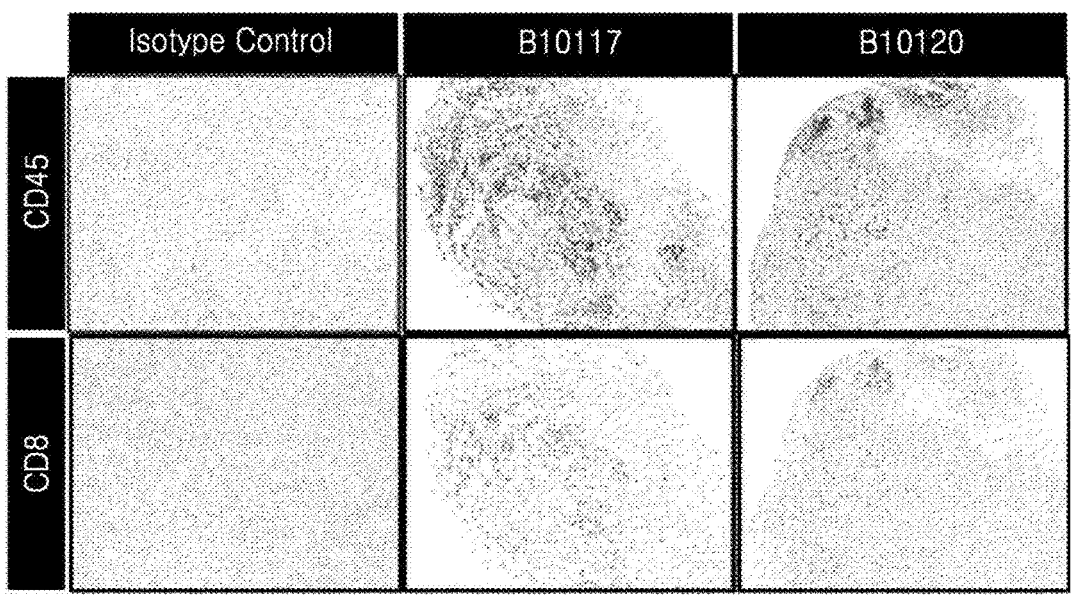
FIG. 9a is images showing tumor-infiltrating lymphocytes (TIL)
Figure 9B:
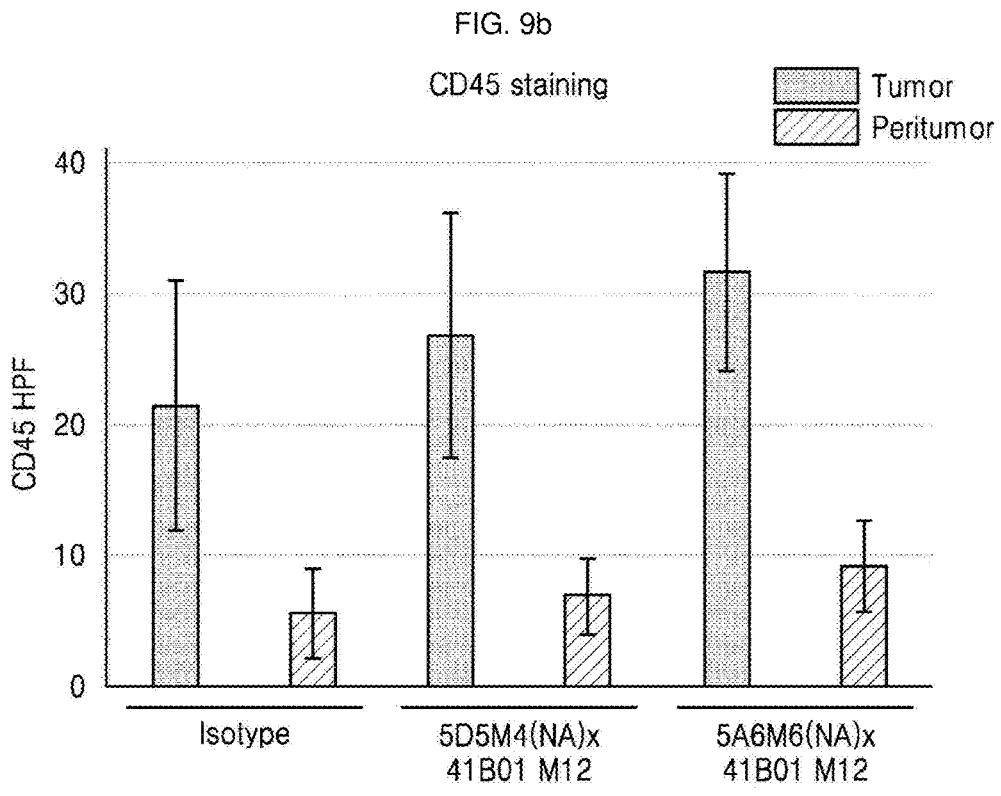
FIG. 9b is graphs showing results of analysis of tumor-infiltrating lymphocytes.
Figure 9B:
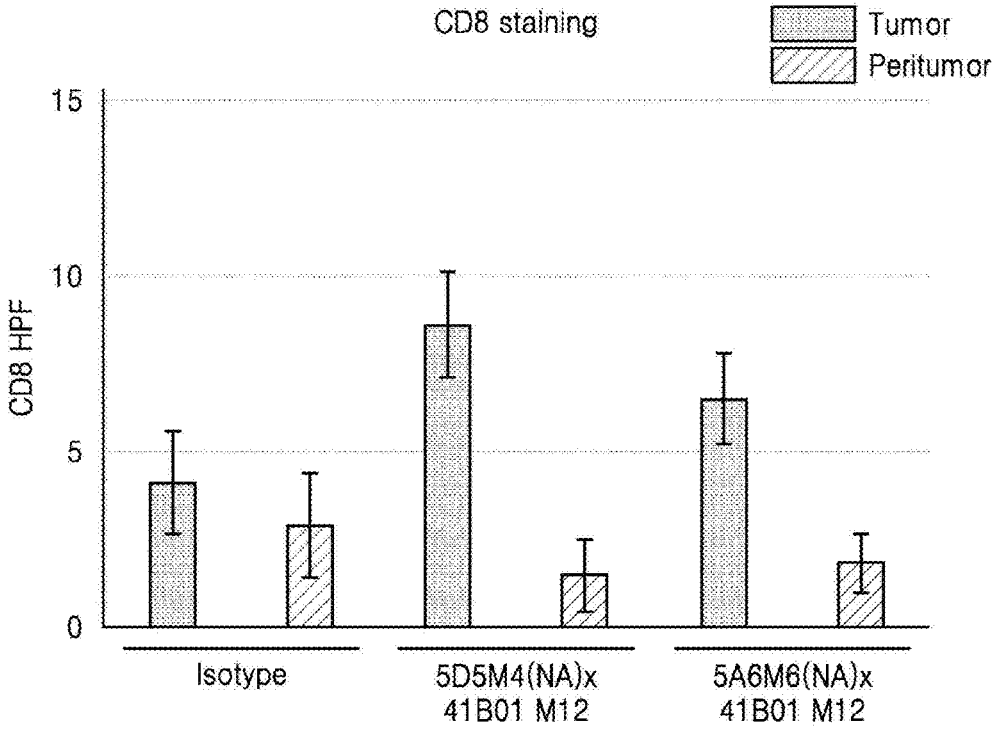

To evaluate TIL, formalin-fixed, paraffin-embedded tumor tissue sections from H929 bearing human T-cell engraft mice were immunostained with anti-CD45 antibody (human leukocyte marker) and anti-CD8 antibody (human cytotoxic T-lymphocyte marker). The immunohistochemical technique was performed by applying the avidin-biotin detection kit. The obtained result is shown in FIGS. 9a and 9b. As shown in FIGS. 9a and 9b, anti-BCMA/anti-4-1BB bispecific antibodies effectively enhanced infiltration of immune cells including CD45+ cells and CD8+ T cells into tumor tissues compared to peritumor. These results shown that CD45+ and CD8+ cells are increased in anti-BCMA/anti-4-1BB bispecific treatment group especially in the tumor compartment.

Figure 10A:
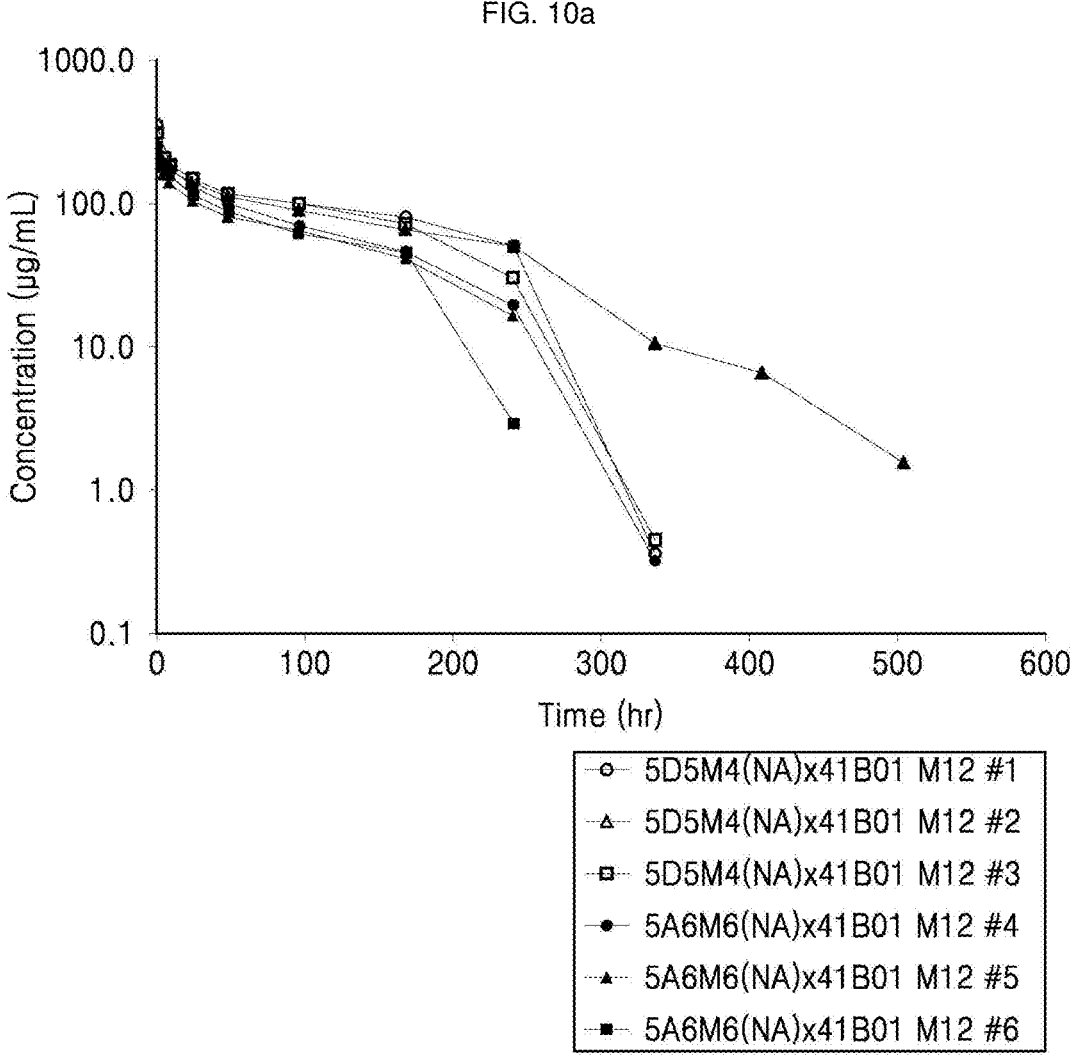
FIG. 10a and FIG. 10b are graphs showing individual results (n=3) and summing results (n=3) for pharmacokinetics of anti-BCMA/anti-4-1BB bispecific antibodies in a cynomolgus monkey, respectively.
Figure 10B:
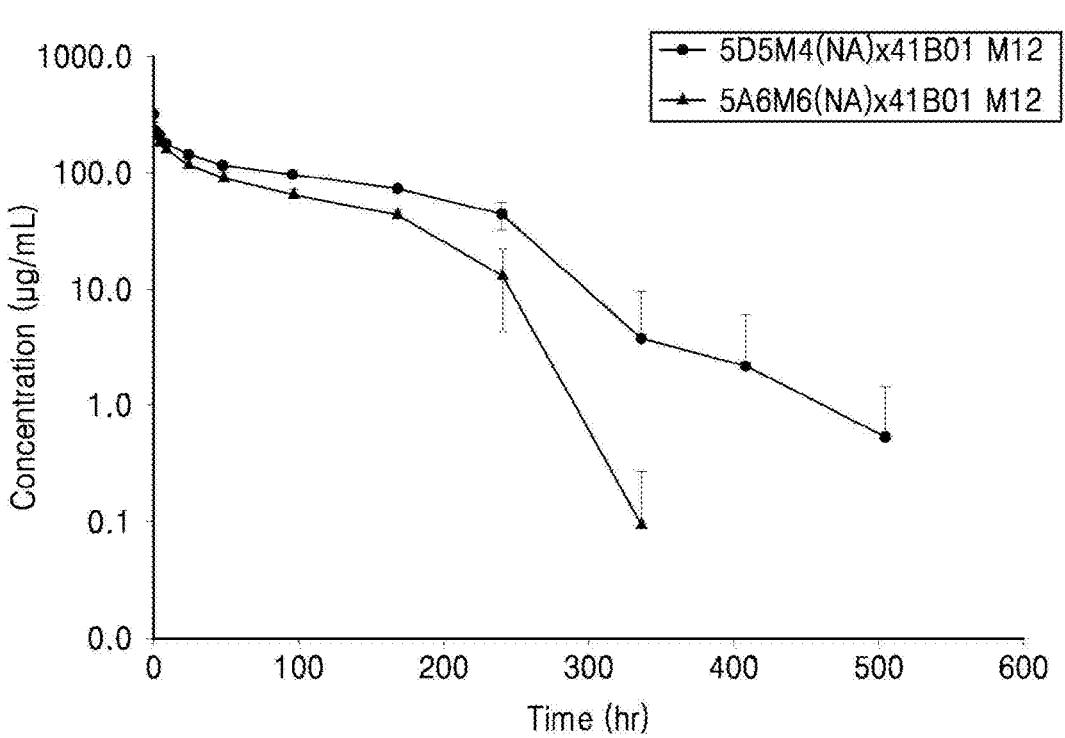

3-11. Pharmacokinetics of Anti-BCMA/Anti-4-1BB Bispecific Antibodies in Cynomolgus Monkey 10 mg/kg of Anti-BCMA/anti-4-1BB bispecific antibodies (5D5M4(NA)X41B01 M12 and 5A6M6(NA)X41B01 M12) were injected via the saphenous vein in Cynomolgus Monkeys. Blood samples were collected from each animal via a femoral vein prior to dosing and at scheduled intervals from 0.05 to 504 hours after administration of the dose. The blood samples were centrifuged to obtain serum. Concentrations of 5D5M4(NA)X41B01 M12 and 5A6M6(NA)X41B01 M12 in cynomolgus monkey serum were measured using enzyme-linked immunosorbent assay (ELISA). 96-well plates were coated with human BCMA-Fc protein, then blocked with blocking buffer. Afterwards, the plates were washed and the standards, quality control samples, and study samples were added to the plates, then incubated for 2 hours at 37° C. The plates were then washed again and incubated with human 4-1BB his protein. After washing, the bound molecules were detected with a horseradish peroxidase conjugated anti-His tagged antibody. The plates were developed with TMB substrate and analyzed by spectrophotometer at OD 450-650 nm. Concentrations from serum samples were determined from a standard curve prepared with known amounts of 5D5M4(NA)X41B01 M12 and 5A6M6(NA)X41B01 M12 in the appropriate cynomolgus monkey serum using a 4-parameter algorithm. The standard curve range for 5D5M4(NA)X41B01 M12 and 5A6M6(NA)X41B01 M12 was from 46 to 300,000 ng/mL, and the lower limit of quantitation (LLOQ) was defined as 300 ng/mL. The pharmacokinetic parameters were estimated by a non-compartment model using WIN-NONLIN® software (Phoenix WINNONLIN® 8.0). The obtained result is shown in FIGS. 10a and 10b. The results of FIGS. 10a and 10b are quantified and summarized in Tables 23 and 24, respectively (WINNONLIN® setting, NCA, Linear Trapezoidal Linear Interpolation, IV Bolus, half-life calculation time: 24 hr to 240 hr). The results showed that 5D5M4(NA)X41B01 M12 has even superior PK property than 5A6M6(NA)X41B01 M12.

TABLE 23

| Subject | N_Samples | Half_Life (hr) | Half_Life (day) | Tmax (hr) | Cmax (ug/mL) | C0 (ug/mL) | AUClast (hr*ug/mL) | AUCINF_obs (hr*ug/mL) | Cl_obs (mL/hr/kg) | Vss_obs (mL/kg) |
|---|---|---|---|---|---|---|---|---|---|---|
| #1 | 9 | 161.6 | 6.7 | 0.1 | 357.6 | 365.6 | 23750.4 | 35845.5 | 0.28 | 62.24 |
| #2 | 9 | 150.8 | 6.3 | 0.1 | 270.1 | 273.4 | 22235.0 | 33335.5 | 0.30 | 64.33 |
| #3 | 9 | 102.7 | 4.3 | 0.1 | 318.3 | 323.3 | 22978.7 | 27517.8 | 0.36 | 50.03 |
| Mean | | 138.4 | 5.8 | 0.1 | 315.3 | 320.8 | 22988.0 | 32232.9 | 0.31 | 58.87 |
| SD | | 31.4 | 1.3 | 0.0 | 43.8 | 46.1 | 757.7 | 4271.9 | 0.04 | 7.73 |

TABLE 24

| Subject | N_Samples | Half_Life (hr) | Half_Life (day) | Tmax (hr) | Cmax (ug/mL) | C0 (ug/mL) | AUClast (hr*ug/mL) | AUCINF_obs (hr*ug/mL) | Cl_obs (mL/hr/kg) | Vss_obs (mL/kg) |
|---|---|---|---|---|---|---|---|---|---|---|
| #4 | 9 | 82.3 | 3.4 | 0.1 | 254.0 | 255.6 | 18066.2 | 20446.6 | 0.49 | 54.39 |
| #5 | 9 | 86.8 | 3.6 | 0.1 | 224.9 | 227.3 | 15369.3 | 17515.9 | 0.57 | 66.52 |
| #6 | 9 | 46.4 | 1.9 | 0.1 | 234.6 | 237.6 | 15671.0 | 15877.5 | 0.63 | 49.92 |
| Mean | | 71.8 | 3.0 | 0.1 | 237.8 | 240.1 | 16368.8 | 17946.7 | 0.56 | 56.94 |
| SD | | 22.1 | 0.9 | 0.0 | 14.8 | 14.3 | 1477.7 | 2314.8 | 0.07 | 8.59 |

3-12. Tumor Growth Inhibition by Anti-BCMA/4-1BB Bispecific Antibody in 4-1 BB Knock-In Mice Bearing BCMA Overexpressed MC38

In vivo anti-tumor efficacy of anti-BCMA/anti-4-1BB bispecific antibody was evaluated with BCMA overexpressed MC38 bearing human 4-1BB knock-in mice system (CRO: Biocytogen). In brief, MC38-hBCMA ($5\times10^6$) cell were inoculated by subcutaneous injection into the right flank of non-irradiated female animals. On Day 7, When the mean tumor volume reached to 110 mm³, mice were randomized to three group (n=8/group). Then, 7.5 mg/kg of Isotype control antibody (hIgG1) and 2 or 0.4 mg/kg of anti-BCMA/anti-4-1BB bispecific antibody (5D5M4(NA) X41B01 M12) were respectively Intravenous administrated total eight times with Q3D (Once every three days) dosing schedule. To obtained the tumor growth results, tumor volumes were monitored by caliper measurement twice per week.

Figure 11:
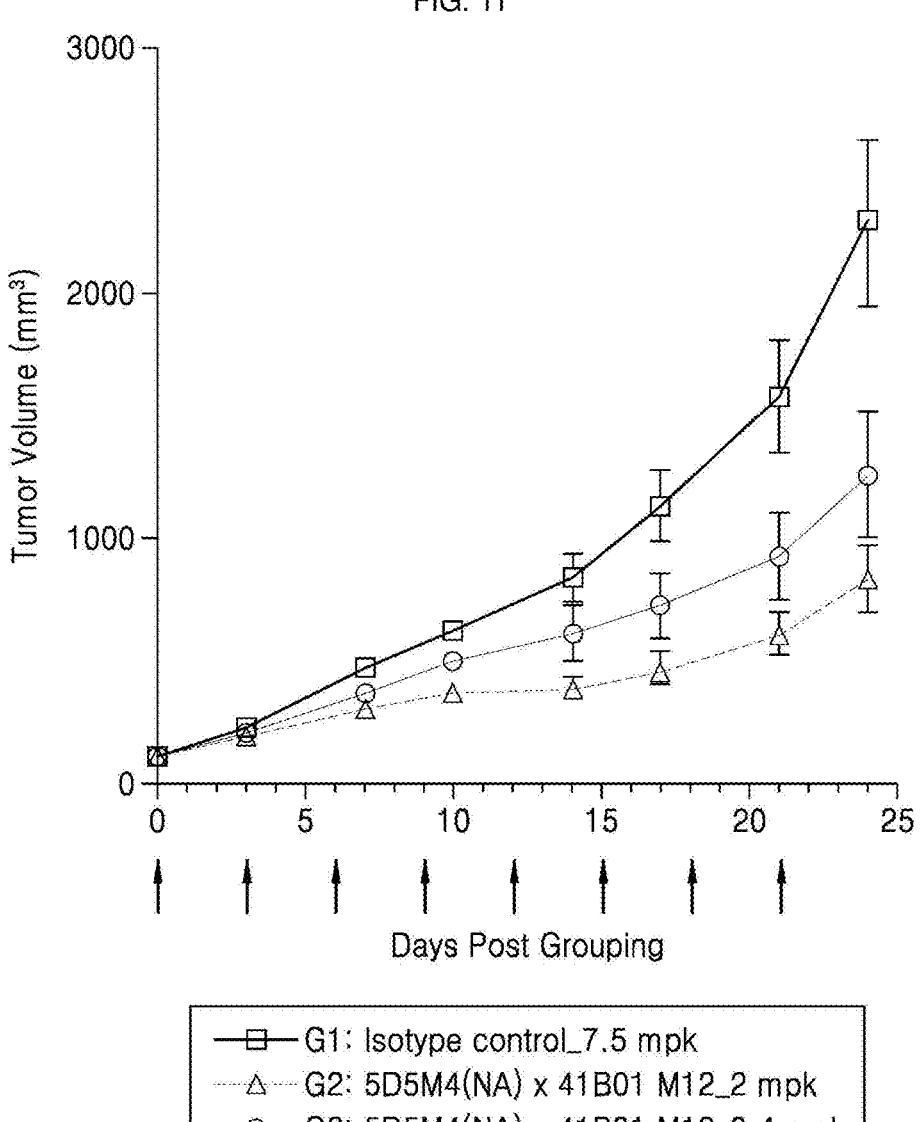
FIG. 11 is a graphs showing tumor growth profile upon administration of anti-BCMA/anti-4-1BB bispecific antibodies (*P<0.05;**P<0.01).

The obtained results are shown in FIG. 11 and Table 25. Table 25 is summary results of tumor growth inhibition for 5D5M4(NA)X41B01 M12 in MC38-hBCMA bearing 4-1BB Knock-in mice (*P<0.05; **P<0.01). In Table 25, Q3D refers to a dosing frequency of once every three day.

TABLE 25

| Group | Dosages | Frequency and time | Tumor volume (mm³) [a] Before treatment | Day 24 post treatment | TGI (%) | P [b] |
|---|---|---|---|---|---|---|
| hIgG1 | 7.5 mg/kg | Q3D, 8 | 106 ± 3 | 2288 ± 964 | — | — |
| 5D5M4(NA)x41B01 | 0.4 mg/kg | Q3D, 8 | 106 ± 3 | 1253 ± 737 | 47.4 | *0.012 |
| M12 | 2 mg/kg | Q3D, 8 | 106 ± 2 | 834 ± 378 | 62.2 | **0.0001 |

As shown in FIG. 11 and Table 25, 5D5M4(NA)X41B01 M12 showed anti-tumor efficacy. Tumor growth inhibition rate (TGI %) was around 62.2% for G2 (5D5M4(NA) X41B01 M12.2 mg/kg) and around 47.4% for G3 (5D5M4 (NA)X41B01 M12, 0.4 mg/kg). In overall, anti-BCMA/anti- 4-1BB bispecific antibodies showed superior anti-tumor efficacy in human BCMA/MC38 tumor.

This application contains references to amino acid sequences and/or nucleic acid sequences which have been submitted concurrently herewith as the sequence listing text file entitled "000010usnp_SequenceListing.TXT", file size 136 kilobytes (KB), created on 20 May 2022. The aforementioned sequence listing is hereby incorporated by reference in its entirety pursuant to 37 C.F.R. § 1.52(e)(5).

---

The invention claimed is:

1. An anti-B-cell maturation antigen (BCMA)/anti-4-1BB bispecific antibody or an antigen-binding fragment thereof, comprising:

an anti-BCMA antibody or an antigen-binding fragment thereof; and an anti-4-1BB antibody or an antigen-binding fragment thereof, wherein anti-B-cell maturation antigen (BCMA)/anti-4-1BB bispecific antibody or an antigen-binding fragment thereof is selected from the group consisting of:

a bispecific antibody comprising an anti BCMA antibody or an antigen-binding fragment thereof comprising a CDR-H1 consisting of the amino acid sequence of SEQ ID NO: 12, a CDR-H2 consisting of the amino acid sequence of SEQ ID NO: 16, and a CDR-H3 consisting of the amino acid sequence of SEQ ID NO: 20, a CDR-L1 consisting of the amino acid sequence of SEQ ID NO: 24, a CDR-L2 consisting of the amino acid sequence of SEQ ID NO: 27, and a CDR-L3 consisting of the amino acid sequence of SEQ ID NO: 31, and an anti-4-1BB antibody or an antigen-binding fragment thereof comprising a CDR-H1 consisting of the amino acid sequence of SEQ ID NO: 81, a CDR-H2 consisting of the amino acid sequence of SEQ ID NO: 84, a CDR-H3 consisting of the amino acid sequence of SEQ ID NO: 88, a CDR-L1 consisting of the amino acid sequence of SEQ ID NO: 92, a CDR-L2 consisting of the amino acid sequence of SEQ ID NO: 94, and a CDR-L3 consisting of the amino acid sequence of SEQ ID NO: 96;

a bispecific antibody comprising an anti BCMA antibody or an antigen-binding fragment thereof comprising a CDR-H1 consisting of the amino acid sequence of SEQ ID NO: 12, a CDR-H2 consisting of the amino acid sequence of SEQ ID NO: 16, a CDR-H3 consisting of the amino acid sequence of SEQ ID NO: 20, a CDR-L1 consisting of the amino acid sequence of SEQ ID NO: 54, a CDR-L2 consisting of the amino acid sequence of SEQ ID NO: 27, and a CDR-L3 consisting of the amino acid sequence of SEQ ID NO: 31, and an anti-4-1BB antibody or an antigen-binding fragment thereof comprising a CDR-H1 consisting of the amino acid sequence of SEQ ID NO: 81, a CDR-H2 consisting of the amino acid sequence of SEQ ID NO: 84, a CDR-H3 consisting of the amino acid sequence of SEQ ID NO: 88, a CDR-L1 consisting of the amino acid sequence of SEQ ID NO: 92, a CDR-L2 consisting of the amino acid sequence of SEQ ID NO: 94, and a CDR-L3 consisting of the amino acid sequence of SEQ ID NO: 96;

a bispecific antibody comprising an anti BCMA antibody or an antigen-binding fragment thereof comprising a CDR-H1 consisting of the amino acid sequence of SEQ ID NO: 12, a CDR-H2 consisting of the amino acid sequence of SEQ ID NO: 16, and a CDR-H3 consisting of the amino acid sequence of SEQ ID NO: 20, a CDR-L1 consisting of the amino acid sequence of SEQ ID NO: 55, a CDR-L2 consisting of the amino acid sequence of SEQ ID NO: 27, and a CDR-L3 consisting of the amino acid sequence of SEQ ID NO: 31, and an anti-4-1BB antibody or an antigen-binding fragment thereof comprising a CDR-H1 consisting of the amino acid sequence of SEQ ID NO: 81, a CDR-H2 consisting of the amino acid sequence of SEQ ID NO: 84, a CDR-H3 consisting of the amino acid sequence of SEQ ID NO: 88, a CDR-L1 consisting of the amino acid sequence of SEQ ID NO: 92, a CDR-L2 consisting of the amino acid sequence of SEQ ID NO: 94, and a CDR-L3 consisting of the amino acid sequence of SEQ ID NO: 96;

a bispecific antibody comprising an anti BCMA antibody or an antigen-binding fragment thereof comprising a CDR-H1 consisting of the amino acid sequence of SEQ ID NO: 12, a CDR-H2 consisting of the amino acid sequence of SEQ ID NO: 16, and a CDR-H3 consisting of the amino acid sequence of SEQ ID NO: 20, a CDR-L1 consisting of the amino acid sequence of SEQ ID NO: 56, a CDR-L2 consisting of the amino acid sequence of SEQ ID NO: 27, and a CDR-L3 consisting of the amino acid sequence of SEQ ID NO: 31, and an anti-4-1BB antibody or an antigen-binding fragment thereof comprising a CDR-H1 consisting of the amino acid sequence of SEQ ID NO: 81, a CDR-H2 consisting of the amino acid sequence of SEQ ID NO: 84, a CDR-H3 consisting of the amino acid sequence of SEQ ID NO: 88, a CDR-L1 consisting of the amino acid sequence of SEQ ID NO: 92, a CDR-L2 consisting of the amino acid sequence of SEQ ID NO: 94, and a CDR-L3 consisting of the amino acid sequence of SEQ ID NO: 96;

a bispecific antibody comprising an anti BCMA antibody or an antigen-binding fragment thereof comprising a CDR-H1 consisting of the amino acid sequence of SEQ ID NO: 12, a CDR-H2 consisting of the amino acid sequence of SEQ ID NO: 16, and a CDR-H3 consisting of the amino acid sequence of SEQ ID NO: 20, a CDR-L1 consisting of the amino acid sequence of SEQ ID NO: 57, a CDR-L2 consisting of the amino acid sequence of SEQ ID NO: 27, and a CDR-L3 consisting of the amino acid sequence of SEQ ID NO: 31, and an anti-4-1BB antibody or an antigen-binding fragment thereof comprising a CDR-H1 consisting of the amino acid sequence of SEQ ID NO: 81, a CDR-H2 consisting of the amino acid sequence of SEQ ID NO: 84, a CDR-H3 consisting of the amino acid sequence of SEQ ID NO: 88, a CDR-L1 consisting of the amino acid sequence of SEQ ID NO: 92, a CDR-L2 consisting of the amino acid sequence of SEQ ID NO: 94, and a CDR-L3 consisting of the amino acid sequence of SEQ ID NO: 96;

a bispecific antibody comprising an anti BCMA antibody or an antigen-binding fragment thereof comprising a CDR-H1 consisting of the amino acid sequence of SEQ ID NO: 12, a CDR-H2 consisting of the amino acid sequence of SEQ ID NO: 16, and a CDR-H3 consisting of the amino acid sequence of SEQ ID NO: 20, a CDR-L1 consisting of the amino acid sequence of SEQ ID NO: 58, a CDR-L2 consisting of the amino acid sequence of SEQ ID NO: 27, and a CDR-L3 consisting of the amino acid sequence of SEQ ID NO: 31, and an anti-4-1BB antibody or an antigen-binding fragment thereof comprising a CDR-H1 consisting of the amino acid sequence of SEQ ID NO: 81, a CDR-H2 consisting of the amino acid sequence of SEQ ID NO: 84, a CDR-H3 consisting of the amino acid sequence of SEQ ID NO: 88, a CDR-L1 consisting of the amino acid sequence of SEQ ID NO: 92, a CDR-L2 consisting of the amino acid sequence of SEQ ID NO: 94, and a CDR-L3 consisting of the amino acid sequence of SEQ ID NO: 96;

a bispecific antibody comprising an anti BCMA antibody or an antigen-binding fragment thereof comprising a CDR-H1 consisting of the amino acid sequence of SEQ ID NO: 13, a CDR-H2 consisting of the amino acid sequence of SEQ ID NO: 17, and a CDR-H3 consisting of the amino acid sequence of SEQ ID NO: 21, a CDR-L1 consisting of the amino acid sequence of SEQ ID NO: 25, a CDR-L2 consisting of the amino acid sequence of SEQ ID NO: 28, and a CDR-L3 consisting of the amino acid sequence of SEQ ID NO: 32, and an anti-4-1BB antibody or an antigen-binding fragment thereof comprising a CDR-H1 consisting of the amino acid sequence of SEQ ID NO: 81, a CDR-H2 consisting of the amino acid sequence of SEQ ID NO: 84, a CDR-H3 consisting of the amino acid sequence of SEQ ID NO: 88, a CDR-L1 consisting of the amino acid sequence of SEQ ID NO: 92, a CDR-L2 consisting of the amino acid sequence of SEQ ID NO: 94, and a CDR-L3 consisting of the amino acid sequence of SEQ ID NO: 96;

a bispecific antibody comprising an anti BCMA antibody or an antigen-binding fragment thereof comprising a CDR-H1 consisting of the amino acid sequence of SEQ ID NO: 13, a CDR-H2 consisting of the amino acid sequence of SEQ ID NO: 17, and a CDR-H3 consisting of the amino acid sequence of SEQ ID NO: 21, a CDR-L1 consisting of the amino acid sequence of SEQ ID NO: 59, a CDR-L2 consisting of the amino acid sequence of SEQ ID NO: 28, and a CDR-L3 consisting of the amino acid sequence of SEQ ID NO: 32, and an anti-4-1BB antibody or an antigen-binding fragment thereof comprising a CDR-H1 consisting of the amino acid sequence of SEQ ID NO: 81, a CDR-H2 consisting of the amino acid sequence of SEQ ID NO: 84, a CDR-H3 consisting of the amino acid sequence of SEQ ID NO: 88, a CDR-L1 consisting of the amino acid sequence of SEQ ID NO: 92, a CDR-L2 consisting of the amino acid sequence of SEQ ID NO: 94, and a CDR-L3 consisting of the amino acid sequence of SEQ ID NO: 96;

a bispecific antibody comprising an anti BCMA antibody or an antigen-binding fragment thereof comprising a CDR-H1 consisting of the amino acid sequence of SEQ ID NO: 13, a CDR-H2 consisting of the amino acid sequence of SEQ ID NO: 17, and a CDR-H3 consisting of the amino acid sequence of SEQ ID NO: 21, a CDR-L1 consisting of the amino acid sequence of SEQ ID NO: 60, a CDR-L2 consisting of the amino acid sequence of SEQ ID NO: 28, and a CDR-L3 consisting of the amino acid sequence of SEQ ID NO: 32, and an anti-4-1BB antibody or an antigen-binding fragment thereof comprising a CDR-H1 consisting of the amino acid sequence of SEQ ID NO: 81, a CDR-H2 consisting of the amino acid sequence of SEQ ID NO: 84, a CDR-H3 consisting of the amino acid sequence of SEQ ID NO: 88, a CDR-L1 consisting of the amino acid sequence of SEQ ID NO: 92, a CDR-L2 consisting of the amino acid sequence of SEQ ID NO: 94, and a CDR-L3 consisting of the amino acid sequence of SEQ ID NO: 96;

a bispecific antibody comprising an anti BCMA antibody or an antigen-binding fragment thereof comprising a CDR-H1 consisting of the amino acid sequence of SEQ ID NO: 13, a CDR-H2 consisting of the amino acid sequence of SEQ ID NO: 17, and a CDR-H3 consisting of the amino acid sequence of SEQ ID NO: 21, a CDR-L1 consisting of the amino acid sequence of SEQ ID NO: 25, a CDR-L2 consisting of the amino acid sequence of SEQ ID NO: 28, and a CDR-L3 consisting of the amino acid sequence of SEQ ID NO: 63, and an anti-4-1BB antibody or an antigen-binding fragment thereof comprising a CDR-H1 consisting of the amino acid sequence of SEQ ID NO: 81, a CDR-H2 consisting of the amino acid sequence of SEQ ID NO: 84, a CDR-H3 consisting of the amino acid sequence of SEQ ID NO: 88, a CDR-L1 consisting of the amino acid sequence of SEQ ID NO: 92, a CDR-L2 consisting of the amino acid sequence of SEQ ID NO: 94, and a CDR-L3 consisting of the amino acid sequence of SEQ ID NO: 96;

a bispecific antibody comprising an anti BCMA antibody or an antigen-binding fragment thereof comprising a CDR-H1 consisting of the amino acid sequence of SEQ ID NO: 13, a CDR-H2 consisting of the amino acid sequence of SEQ ID NO: 17, and a CDR-H3 consisting of the amino acid sequence of SEQ ID NO: 21, a CDR-L1 consisting of the amino acid sequence of SEQ ID NO: 25, a CDR-L2 consisting of the amino acid sequence of SEQ ID NO: 28, and a CDR-L3 consisting of the amino acid sequence of SEQ ID NO: 64, and an anti-4-1BB antibody or an antigen-binding fragment thereof comprising a CDR-H1 consisting of the amino acid sequence of SEQ ID NO: 81, a CDR-H2 consisting of the amino acid sequence of SEQ ID NO: 84, a CDR-H3 consisting of the amino acid sequence of SEQ ID NO: 88, a CDR-L1 consisting of the amino acid sequence of SEQ ID NO: 92, a CDR-L2 consisting of the amino acid sequence of SEQ ID NO: 94, and a CDR-L3 consisting of the amino acid sequence of SEQ ID NO: 96;

a bispecific antibody comprising an anti BCMA antibody or an antigen-binding fragment thereof comprising a CDR-H1 consisting of the amino acid sequence of SEQ ID NO: 13, a CDR-H2 consisting of the amino acid sequence of SEQ ID NO: 17, and a CDR-H3 consisting of the amino acid sequence of SEQ ID NO: 21, a CDR-L1 consisting of the amino acid sequence of SEQ ID NO: 61, a CDR-L2 consisting of the amino acid sequence of SEQ ID NO: 28, and a CDR-L3 consisting of the amino acid sequence of SEQ ID NO: 63, and an anti-4-1BB antibody or an antigen-binding fragment thereof comprising a CDR-H1 consisting of the amino acid sequence of SEQ ID NO: 81, a CDR-H2 consisting of the amino acid sequence of SEQ ID NO: 84, a CDR-H3 consisting of the amino acid sequence of SEQ ID NO: 88, a CDR-L1 consisting of the amino acid sequence of SEQ ID NO: 92, a CDR-L2 consisting of the amino acid sequence of SEQ ID NO: 94, and a CDR-L3 consisting of the amino acid sequence of SEQ ID NO: 96;

a bispecific antibody comprising an anti BCMA antibody or an antigen-binding fragment thereof comprising a CDR-H1 consisting of the amino acid sequence of SEQ ID NO: 13, a CDR-H2 consisting of the amino acid sequence of SEQ ID NO: 17, and a CDR-H3 consisting of the amino acid sequence of SEQ ID NO: 21, a CDR-L1 consisting of the amino acid sequence of SEQ ID NO: 61, a CDR-L2 consisting of the amino acid sequence of SEQ ID NO: 28, and a CDR-L3 consisting of the amino acid sequence of SEQ ID NO: 64, and an anti-4-1BB antibody or an antigen-binding fragment thereof comprising a CDR-H1 consisting of the amino acid sequence of SEQ ID NO: 81, a CDR-H2 consisting of the amino acid sequence of SEQ ID NO: 84, a CDR-H3 consisting of the amino acid sequence of SEQ ID NO: 88, a CDR-L1 consisting of the amino acid sequence of SEQ ID NO: 92, a CDR-L2 consisting of the amino acid sequence of SEQ ID NO: 94, and a CDR-L3 consisting of the amino acid sequence of SEQ ID NO: 96;

a bispecific antibody comprising an anti BCMA antibody or an antigen-binding fragment thereof comprising a CDR-H1 consisting of the amino acid sequence of SEQ ID NO: 13, a CDR-H2 consisting of the amino acid sequence of SEQ ID NO: 17, and a CDR-H3 consisting of the amino acid sequence of SEQ ID NO: 21, a CDR-L1 consisting of the amino acid sequence of SEQ ID NO: 62, a CDR-L2 consisting of the amino acid sequence of SEQ ID NO: 28, and a CDR-L3 consisting of the amino acid sequence of SEQ ID NO: 63, and an anti-4-1BB antibody or an antigen-binding fragment thereof comprising a CDR-H1 consisting of the amino acid sequence of SEQ ID NO: 81, a CDR-H2 consisting of the amino acid sequence of SEQ ID NO: 84, a CDR-H3 consisting of the amino acid sequence of SEQ ID NO: 88, a CDR-L1 consisting of the amino acid sequence of SEQ ID NO: 92, a CDR-L2 consisting of the amino acid sequence of SEQ ID NO: 94, and a CDR-L3 consisting of the amino acid sequence of SEQ ID NO: 96; and a bispecific antibody comprising an anti BCMA antibody or an antigen-binding fragment thereof comprising a CDR-H1 consisting of the amino acid sequence of SEQ ID NO: 13, a CDR-H2 consisting of the amino acid sequence of SEQ ID NO: 17, and a CDR-H3 consisting of the amino acid sequence of SEQ ID NO: 21, a CDR-L1 consisting of the amino acid sequence of SEQ ID NO: 62, a CDR-L2 consisting of the amino acid sequence of SEQ ID NO: 28, and a CDR-L3 consisting of the amino acid sequence of SEQ ID NO: 64, and an anti-4-1BB antibody or an antigen-binding fragment thereof comprising a CDR-H1 consisting of the amino acid sequence of SEQ ID NO: 81, a CDR-H2 consisting of the amino acid sequence of SEQ ID NO: 84, a CDR-H3 consisting of the amino acid sequence of SEQ ID NO: 88, a CDR-L1 consisting of the amino acid sequence of SEQ ID NO: 92, a CDR-L2 consisting of the amino acid sequence of SEQ ID NO: 94, and a CDR-L3 consisting of the amino acid sequence of SEQ ID NO: 96.

2. The bispecific antibody or the antigen-binding fragment thereof of claim 1, wherein the anti-BCMA antibody or the antigen-binding fragment thereof comprises a heavy chain variable region comprising an amino acid sequence selected from the group consisting of SEQ ID NOs: 4 and 5 and a light chain variable region comprising an amino acid sequence selected from the group consisting of SEQ ID NOs: 8, 9, and 41 to 53.

3. The bispecific antibody or the antigen-binding fragment thereof of claim 1, wherein the anti-4-11BB antibody or the antigen-binding fragment thereof comprises a heavy chain variable region comprising an amino acid sequence of SEQ ID NO: 68 and a light chain variable region comprising an amino acid sequence of SEQ ID NO: 76.

4. The bispecific antibody or the antigen-binding fragment thereof of claim 1, further comprising at least one peptide linker.

5. The bispecific antibody or the antigen-binding fragment thereof of claim 4, wherein the peptide linker comprises a peptide having an amino acid sequence selected from the group consisting of SEQ ID NO: 98 and SEQ ID NO: 99.

6. The bispecific antibody or the antigen-binding fragment thereof of claim 1, wherein the antibody is IgA, IgD, IgE, IgG, or IgM;

wherein the antibody is a monoclonal antibody or a polyclonal antibody;

wherein the antigen-binding fragment thereof is scFv, (scFv)2, Fv, Fab, Fab', F(ab')2, or a combination thereof; or wherein the antibody or the antigen-binding fragment thereof is modified by conjugation.

7. The bispecific antibody or the antigen-binding fragment thereof of claim 1, wherein each of the anti-BCMA antibody or the antigen-binding fragment thereof and the anti-4-1BB antibody or the antigen-binding fragment thereof is independently a chimeric antibody, a humanized antibody, or a human antibody.

8. The bispecific antibody or the antigen-binding fragment thereof of claim 1, wherein the bispecific antibody or the antigen-binding fragment thereof is in the form of IgG-scFv, triomab, knobs into holes (KiH) IgG with common light chains, crossmab, ortho-Fab IgG, dual variable domain immunoglobulin, 2 in 1-IgG, scFv2-Fc fusion, a bispecific T cell engager, tandAbs, dual affinity retargeting antibody, dual affinity retargeting antibody-Fc fusion, scFv-human serum albumin (HSA)-scFv, dock-and-lock (DNL)-Fab3, a minibody, scFv-Fc fusion, scFv-zipper, scFv, Fab, Fab2, Fab3, scFab, Bis-B scFv, a tetrabody, a triabody, a diabody, a bispecific construct comprising a knobs B into holes (KiH) IgG, a tetravalent multispecific antibody, a tetravalent dual variable domain (DVD) construct, a tetravalent IgGScv construct, or a composite antibody, or a combination thereof.

9. A pharmaceutical composition for treatment of a disease related to BCMA, 4-1BB, or both, the composition comprising the anti-BCMA/anti-4-1BB bispecific antibody or the antigen-binding fragment thereof of claim 1, and a pharmaceutically acceptable carrier, wherein the disease is cancer.

10. A method of treatment of a disease related to BCMA, 4-1 BB, or both in an individual in need thereof, the method comprising: administering the anti-BCMA/anti-4-1BB bispecific antibody or the antigen-binding fragment thereof of claim 1 to the individual, wherein the disease is cancer.

11. The method of claim 10, wherein the cancer is multiple myeloma.

\* \* \* \* \*